(12) United States Patent
Voegele et al.

(10) Patent No.: US 8,545,450 B2
(45) Date of Patent: Oct. 1, 2013

(54) MULTI-PORT LAPAROSCOPIC ACCESS DEVICE

(75) Inventors: James W. Voegele, Cincinnati, OH (US); Robert P. Gill, Mason, OH (US); Aaron C. Voegele, Loveland, OH (US); William B. Weisenburgh, II, Maineville, OH (US); Christopher J. Hess, Cincinnati, OH (US); William P. Geis, Baltimore, MD (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1262 days.

(21) Appl. No.: 11/398,985

(22) Filed: Apr. 5, 2006

(65) Prior Publication Data
US 2006/0247673 A1 Nov. 2, 2006

Related U.S. Application Data

(60) Provisional application No. 60/669,514, filed on Apr. 8, 2005, provisional application No. 60/700,176, filed on Jul. 18, 2005.

(51) Int. Cl.
*A61M 5/32* (2006.01)

(52) U.S. Cl.
USPC .................................................. 604/175

(58) Field of Classification Search
USPC .......... 604/93.01, 99.03, 264, 27, 34, 167.02, 604/167.03, 236, 247, 284, 174, 175; 606/167, 606/170, 1
See application file for complete search history.

(56) References Cited

U.S. PATENT DOCUMENTS

| 2,129,391 A | 9/1938 | Wapplir |
| 3,299,883 A | 1/1967 | Rubens |
| 3,402,710 A | 9/1968 | Paleschnek |
| 3,503,396 A | 3/1970 | Pierie et al. |
| 3,654,965 A | 4/1972 | Gramain |
| 4,041,931 A | 8/1977 | Elliott et al. |
| 4,048,987 A | 9/1977 | Hurson |
| 4,112,932 A | 9/1978 | Chiulli |
| 4,120,302 A | 10/1978 | Ziegler |

(Continued)

FOREIGN PATENT DOCUMENTS

| CA | 2095064 | 11/1993 |
| EP | 0646358 | 4/1995 |

(Continued)

OTHER PUBLICATIONS

"Adult Cardiac Surgical Instruments," from the website of Genesee BioMedical, Inc. (date of first publication unknown) Applicants admit the status of this publication as prior art for the limited purpose of examination of this application, but otherwise reserve the right to challenge the status of this publication as prior art.

(Continued)

*Primary Examiner* — Manuel Mendez

(57) ABSTRACT

A surgical access device includes a base having two or more ports or apertures that provide for the insertion of surgical instruments. The multi-port insert may be used with a laparoscopic access device. The multi-port insert may also include one or more instrument supports that are attached to the base to fix the position of one or more surgical instruments inserted through the multi-port insert.

17 Claims, 78 Drawing Sheets

(56) References Cited

U.S. PATENT DOCUMENTS

| | | |
|---|---|---|
| 4,306,545 A | 12/1981 | Ivan et al. |
| 4,373,532 A | 2/1983 | Hill et al. |
| 4,402,683 A | 9/1983 | Kopman |
| 4,417,888 A | 11/1983 | Cosentino et al. |
| 4,559,947 A | 12/1985 | Renger et al. |
| 4,669,473 A | 6/1987 | Richards et al. |
| 4,821,719 A | 4/1989 | Fogarty |
| 4,831,070 A | 5/1989 | McInally et al. |
| 5,027,800 A | 7/1991 | Rowland |
| 5,082,111 A | 1/1992 | Corbitt, Jr. et al. |
| 5,183,471 A | 2/1993 | Wilk |
| 5,197,955 A | 3/1993 | Stephens et al. |
| 5,207,213 A | 5/1993 | Auhll et al. |
| 5,209,741 A | 5/1993 | Spaeth |
| 5,269,772 A | 12/1993 | Wilk |
| 5,308,336 A | 5/1994 | Hart et al. |
| 5,342,315 A | 8/1994 | Rowe et al. |
| 5,345,927 A | 9/1994 | Bonutti |
| 5,362,294 A | 11/1994 | Seitzinger |
| 5,366,478 A | 11/1994 | Brinkerhoff et al. |
| 5,368,597 A | 11/1994 | Pagedas |
| 5,385,553 A | 1/1995 | Hart et al. |
| 5,385,560 A | 1/1995 | Wulf |
| 5,391,154 A | 2/1995 | Young |
| 5,398,671 A | 3/1995 | Ortiz et al. |
| 5,443,452 A | 8/1995 | Hart et al. |
| 5,443,484 A | 8/1995 | Kirsch et al. |
| 5,480,410 A | 1/1996 | Cuschieri et al. |
| 5,501,653 A | 3/1996 | Chin |
| 5,545,123 A | 8/1996 | Ortiz et al. |
| 5,545,179 A | 8/1996 | Williamson, IV |
| 5,547,458 A | 8/1996 | Ortiz et al. |
| 5,569,205 A | 10/1996 | Hart et al. |
| 5,569,254 A | 10/1996 | Carlson et al. |
| 5,582,577 A | 12/1996 | Lund et al. |
| 5,586,977 A | 12/1996 | Dorsey, III |
| 5,591,182 A | 1/1997 | Johnson |
| 5,595,193 A | 1/1997 | Walus et al. |
| 5,603,702 A * | 2/1997 | Smith et al. ............ 604/256 |
| 5,624,381 A | 4/1997 | Kieturakis |
| 5,630,831 A | 5/1997 | Lahr |
| 5,634,882 A | 6/1997 | Gagner |
| 5,634,911 A | 6/1997 | Hermann et al. |
| 5,634,937 A | 6/1997 | Mollenauer et al. |
| 5,636,645 A | 6/1997 | Ou |
| 5,640,977 A | 6/1997 | Leahy et al. |
| 5,643,283 A | 7/1997 | Younker |
| 5,643,301 A | 7/1997 | Mollenauer |
| 5,647,372 A | 7/1997 | Tovey et al. |
| 5,653,705 A | 8/1997 | de la Torre et al. |
| 5,665,093 A | 9/1997 | Atkins et al. |
| 5,672,168 A * | 9/1997 | de la Torre et al. ............ 606/1 |
| 5,676,146 A | 10/1997 | Scarborough |
| 5,676,657 A | 10/1997 | Yoon |
| 5,681,324 A | 10/1997 | Kammerer et al. |
| 5,695,448 A | 12/1997 | Kimura et al. |
| 5,716,327 A | 2/1998 | Warner et al. |
| 5,716,407 A | 2/1998 | Knapp et al. |
| 5,728,121 A | 3/1998 | Bimbo et al. |
| 5,735,289 A | 4/1998 | Pfeffer et al. |
| 5,743,851 A | 4/1998 | Moll et al. |
| 5,772,654 A | 6/1998 | Leyva |
| 5,793,113 A | 8/1998 | Oda |
| 5,813,409 A | 9/1998 | Leahy et al. |
| 5,814,058 A | 9/1998 | Carlson et al. |
| 5,816,257 A | 10/1998 | Chin |
| 5,827,319 A | 10/1998 | Carlson et al. |
| 5,840,078 A | 11/1998 | Yerys |
| 5,842,971 A | 12/1998 | Yoon |
| 5,853,395 A | 12/1998 | Crook et al. |
| 5,865,807 A | 2/1999 | Blake, III |
| 5,876,447 A | 3/1999 | Arnett |
| 5,891,013 A | 4/1999 | Thompson |
| 5,893,878 A | 4/1999 | Pierce |
| 5,906,577 A | 5/1999 | Beane et al. |
| 5,941,890 A | 8/1999 | Voegele et al. |
| 5,947,922 A | 9/1999 | MacLeod |
| 5,957,913 A | 9/1999 | de la Torre et al. |
| 5,971,995 A | 10/1999 | Rousseau |
| 5,977,431 A | 11/1999 | Knapp |
| 5,990,382 A | 11/1999 | Fox |
| 6,007,561 A | 12/1999 | Bourque et al. |
| 6,024,736 A | 2/2000 | de la Torre et al. |
| 6,033,428 A | 3/2000 | Sardella |
| RE36,702 E | 5/2000 | Green et al. |
| 6,074,419 A | 6/2000 | Healy et al. |
| 6,077,288 A | 6/2000 | Shimomura et al. |
| 6,086,603 A * | 7/2000 | Termin et al. ............ 606/191 |
| 6,093,141 A | 7/2000 | Mosseri et al. |
| 6,110,154 A * | 8/2000 | Shimomura et al. ........ 604/256 |
| 6,120,513 A | 9/2000 | Bailey et al. |
| 6,123,689 A | 9/2000 | To et al. |
| 6,126,671 A | 10/2000 | Richards et al. |
| 6,132,385 A | 10/2000 | Vain |
| 6,149,642 A | 11/2000 | Gerhart et al. |
| 6,159,200 A | 12/2000 | Verdura et al. |
| 6,165,184 A | 12/2000 | Verdura et al. |
| 6,197,034 B1 | 3/2001 | Gvozdic et al. |
| 6,217,555 B1 | 4/2001 | Hart et al. |
| 6,220,248 B1 | 4/2001 | Voegele et al. |
| 6,228,055 B1 | 5/2001 | Foerster et al. |
| 6,245,052 B1 | 6/2001 | Orth et al. |
| 6,258,069 B1 | 7/2001 | Carpentier et al. |
| 6,258,102 B1 | 7/2001 | Pagedas |
| 6,261,302 B1 | 7/2001 | Voegele et al. |
| 6,262,196 B1 | 7/2001 | Mecking |
| 6,264,599 B1 | 7/2001 | Slater et al. |
| 6,290,705 B1 | 9/2001 | Chan et al. |
| 6,293,966 B1 | 9/2001 | Frantzen |
| 6,315,770 B1 | 11/2001 | de la Torre et al. |
| 6,319,246 B1 | 11/2001 | de la Torre et al. |
| 6,347,940 B1 | 2/2002 | Gordils et al. |
| 6,348,034 B1 | 2/2002 | Thompson |
| 6,352,503 B1 | 3/2002 | Matsui et al. |
| 6,425,903 B1 | 7/2002 | Voegele |
| 6,447,443 B1 | 9/2002 | Keogh et al. |
| 6,447,489 B1 | 9/2002 | Peterson |
| 6,454,783 B1 | 9/2002 | Piskun |
| 6,458,077 B1 | 10/2002 | Boebel et al. |
| 6,471,714 B1 | 10/2002 | Kim |
| 6,485,467 B1 | 11/2002 | Crook et al. |
| 6,551,270 B1 * | 4/2003 | Bimbo et al. ............ 604/93.01 |
| 6,551,282 B1 | 4/2003 | Exline et al. |
| 6,578,577 B2 | 6/2003 | Bonadio et al. |
| 6,579,304 B1 | 6/2003 | Hart et al. |
| 6,589,167 B1 | 7/2003 | Shimomura et al. |
| 6,605,063 B2 | 8/2003 | Bousquet |
| 6,623,426 B2 | 9/2003 | Bonadio et al. |
| 6,634,883 B2 | 10/2003 | Ranalli |
| 6,669,674 B1 | 12/2003 | Macoviak et al. |
| 6,702,787 B2 | 3/2004 | Racenet et al. |
| 6,706,033 B1 | 3/2004 | Martinez et al. |
| 6,706,050 B1 | 3/2004 | Giannadakis |
| 6,725,083 B1 | 4/2004 | Burbank et al. |
| 6,764,473 B2 | 7/2004 | Morton |
| 6,766,186 B1 | 7/2004 | Hoyns et al. |
| 6,810,880 B1 | 11/2004 | Jennings, Jr. et al. |
| 6,821,247 B2 | 11/2004 | Vierra et al. |
| 6,846,287 B2 | 1/2005 | Bonadio et al. |
| 6,908,430 B2 | 6/2005 | Caldwell et al. |
| 6,939,296 B2 | 9/2005 | Ewers et al. |
| 6,945,932 B1 | 9/2005 | Caldwell et al. |
| 6,972,026 B1 | 12/2005 | Caldwell et al. |
| 6,994,712 B1 | 2/2006 | Fisher et al. |
| 7,008,377 B2 * | 3/2006 | Beane et al. ............ 600/207 |
| 7,014,628 B2 | 3/2006 | Bousquet |
| 7,052,454 B2 | 5/2006 | Taylor |
| 7,083,576 B2 | 8/2006 | Zarins et al. |
| 7,118,528 B1 | 10/2006 | Piskun |
| 7,163,510 B2 | 1/2007 | Kahle et al. |
| 7,214,185 B1 | 5/2007 | Rosney et al. |
| 7,311,661 B2 | 12/2007 | Heinrich |
| 7,338,473 B2 | 3/2008 | Campbell et al. |
| 7,344,547 B2 | 3/2008 | Piskun |

| | | |
|---|---|---|
| 7,393,322 B2 | 7/2008 | Wenchell |
| 7,416,533 B2 | 8/2008 | Gellman et al. |
| 7,438,702 B2 | 10/2008 | Hart et al. |
| 7,585,288 B2 | 9/2009 | Haberland et al. |
| 2001/0034528 A1 | 10/2001 | Foerster et al. |
| 2001/0053510 A1 | 12/2001 | Ranalli |
| 2002/0007112 A1 | 1/2002 | Rupp et al. |
| 2002/0026201 A1 | 2/2002 | Foerester et al. |
| 2002/0038179 A1 | 3/2002 | Tschernoster et al. |
| 2002/0103434 A1 | 8/2002 | Swanbom |
| 2002/0193815 A1 | 12/2002 | Foerster et al. |
| 2003/0113540 A1 | 6/2003 | Anderson et al. |
| 2003/0139756 A1 | 7/2003 | Brustad |
| 2003/0206860 A1 | 11/2003 | Bleyer et al. |
| 2003/0225420 A1 | 12/2003 | Wardle |
| 2004/0015185 A1 | 1/2004 | Ewers et al. |
| 2004/0024304 A1 | 2/2004 | Foerster |
| 2004/0049100 A1 | 3/2004 | Butler et al. |
| 2004/0106942 A1 | 6/2004 | Taylor et al. |
| 2004/0106986 A1 | 6/2004 | Andersson et al. |
| 2004/0138528 A1 | 7/2004 | Richter et al. |
| 2004/0147933 A1 | 7/2004 | McGovern |
| 2004/0154624 A1 | 8/2004 | Bonadio et al. |
| 2004/0215063 A1 | 10/2004 | Bonadio et al. |
| 2004/0230160 A1 | 11/2004 | Blanco |
| 2004/0230161 A1 | 11/2004 | Zeiner |
| 2004/0254426 A1 | 12/2004 | Wenchell |
| 2004/0267213 A1 | 12/2004 | Knapp |
| 2005/0020884 A1 | 1/2005 | Hart et al. |
| 2005/0033342 A1 | 2/2005 | Hart et al. |
| 2005/0085842 A1 | 4/2005 | Eversull et al. |
| 2005/0137609 A1 | 6/2005 | Guiraudon |
| 2005/0148823 A1 | 7/2005 | Vaugh et al. |
| 2005/0155611 A1 | 7/2005 | Vaugh et al. |
| 2005/0192483 A1 | 9/2005 | Bonadio et al. |
| 2005/0209608 A1 | 9/2005 | O'Heeron |
| 2005/0222582 A1 | 10/2005 | Wenchell |
| 2005/0267419 A1 | 12/2005 | Smith |
| 2005/0273132 A1 | 12/2005 | Shluzas et al. |
| 2005/0277946 A1 | 12/2005 | Greenhalgh |
| 2006/0020214 A1 | 1/2006 | Mori et al. |
| 2006/0020241 A1 | 1/2006 | Piskun et al. |
| 2006/0020281 A1 | 1/2006 | Smith |
| 2006/0071432 A1 | 4/2006 | Staudner |
| 2006/0212062 A1 | 9/2006 | Farascioni |
| 2006/0224129 A1 | 10/2006 | Beasley et al. |
| 2006/0224164 A1 | 10/2006 | Hart et al. |
| 2006/0229501 A1 | 10/2006 | Jensen et al. |
| 2006/0241651 A1 | 10/2006 | Wilk |
| 2006/0241671 A1 | 10/2006 | Greenhalgh |
| 2006/0254706 A1 | 11/2006 | Swisher et al. |
| 2007/0049966 A1 | 3/2007 | Bonadio et al. |
| 2007/0060939 A1 | 3/2007 | Lancial et al. |
| 2007/0085232 A1 | 4/2007 | Brustad et al. |
| 2007/0088202 A1 | 4/2007 | Albrecht et al. |
| 2007/0088277 A1 | 4/2007 | McGinley et al. |
| 2007/0118021 A1 | 5/2007 | Pokorney |
| 2007/0151566 A1 | 7/2007 | Kahle et al. |
| 2007/0208312 A1 | 9/2007 | Norton et al. |
| 2007/0255219 A1 | 11/2007 | Vaugh et al. |
| 2008/0027476 A1 | 1/2008 | Piskun |
| 2008/0051739 A1 | 2/2008 | McFarlane |
| 2008/0065021 A1 | 3/2008 | Jenkins et al. |
| 2008/0119821 A1 | 5/2008 | Agnihotri et al. |
| 2008/0255519 A1 | 10/2008 | Piskun et al. |
| 2009/0012477 A1 | 1/2009 | Norton et al. |
| 2009/0036738 A1 | 2/2009 | Cuschieri et al. |
| 2009/0062618 A1 | 3/2009 | Drew et al. |

FOREIGN PATENT DOCUMENTS

| | | |
|---|---|---|
| EP | 0966925 | 4/2003 |
| EP | 0966924 | 8/2003 |
| EP | 1350476 | 10/2003 |
| JP | 2000-033089 | 2/2000 |
| JP | 2000/511788 A | 9/2000 |
| JP | 2003/126105 A | 5/2003 |
| JP | 06320750 | 11/2006 |
| WO | 98/10712 | 3/1993 |
| WO | 96/08208 | 3/1996 |
| WO | 97/35521 | 10/1997 |
| WO | 99/03536 | 1/1999 |
| WO | 00/30592 | 6/2000 |
| WO | 00/32253 | 6/2000 |
| WO | 02/39890 | 5/2002 |
| WO | 02/39918 | 5/2002 |
| WO | 02/058543 | 8/2002 |
| WO | 02/094133 | 11/2002 |
| WO | 03/005890 | 1/2003 |
| WO | 03/28525 A2 | 4/2003 |
| WO | 03/061738 A1 | 7/2003 |
| WO | 03/077730 | 9/2003 |
| WO | 97/29709 | 12/2003 |
| WO | 2004/049902 A2 | 6/2004 |
| WO | 2005094432 | 10/2005 |
| WO | 2007119232 | 10/2007 |
| WO | 2008024502 | 2/2008 |

OTHER PUBLICATIONS

"Bard® Bi-Directional and Kelly-Wick Tunnelers—Instructions for Use," by Bard Peripheral Vascular (Apr. 2006).

"Hand Instruments," from the website of Olympus Surgical America (date of first publication unknown) Applicants admit the status of this publication as prior art for the limited purpose of examination of this application, but otherwise reserve the right to challenge the status of this publication as prior art.

Ashida, R. et al., "Indocyanine Green is an Ideal Dye for Endoscopic Ultrasound-Guided Fine-Needle Tattooing of Pancreatic Tumors" *Endoscopy*, 38, pp. 190-192 (2006).

*Twentieth Edition—Illustrations of Surgical Instruments*, by The Kny-Scheerer Company, New York. USA, pp. 1003, 1026, 1028-1029, 1133, 2034, 2068-2069, 2097-2099, 2132, 2137, 2144, 2155-2156, 2162, 2167-2171, 2173, 2175, 2244, 2255, 2281-2282, 2327, 2333, 2338-2348, 2352, 2355, 2359, 2371, 3017, 3039-3073, 3132, 3165, 3168-3169, 3208-3209, 3219 (Jul. 1915).

"Pen Competitors".

Lee, D.I. et al., "Novel Approach to Minimizing Trocar Sites during Challenging Hand-Assisted Laparoscopic Surgery Utilizing the Gelport: Trans-Gel Instrument Insertion and Utilization," *Journal of Endourology*, vol. 17, No. 2, pp. 69-71 (Mar. 2003).

"Applied GelPort System" by Applied Medical Resources Corporation (2004).

"Applied GelPort Advanced Access Device," by Applied Medical Resources Corporation (Nov. 2002).

"1 Lap Disc Hand Access Device—Ref. LD111," by Ethicon Endo-Surgery, Inc. (date unknown).

"Intrack XT—Low Profile Atraumatic Clamps," by Novare Surgical Systems, Inc. (2002).

Webpage of Novare Surgical, Inc. featuring clamps (date of first publication unknown). Applicants admit the status of this publication as prior art for the limited purpose of examination of this application, but otherwise reserve the right to challenge the status of this publication as prior art.

Co-pending application filed Apr. 5, 2006, U.S. Appl. No. 11/398,985.

Co-pending application filed Apr. 5, 2006, U.S. Appl. No. 11/399,172.

Co-pending application filed Apr. 5, 2006, U.S. Appl. No. 11/399,045.

Co-pending application filed Apr. 5, 2006, U.S. Appl. No. 11/399,044.

Co-pending application filed Apr. 5, 2006, U.S. Appl. No. 11/399,181.

Co-pending application filed Oct. 15, 2009, U.S. Appl. No. 12/579,625.

Co-pending application filed U.S. Appl. No. 12/781,996, U.S. Appl. No. 12/781,996.

International Search Report dated Apr. 30, 2010, International Application No. PCT/US06/13456.

European Search Report dated Mar. 27, 2012, for Application No. 06749740.4.

\* cited by examiner

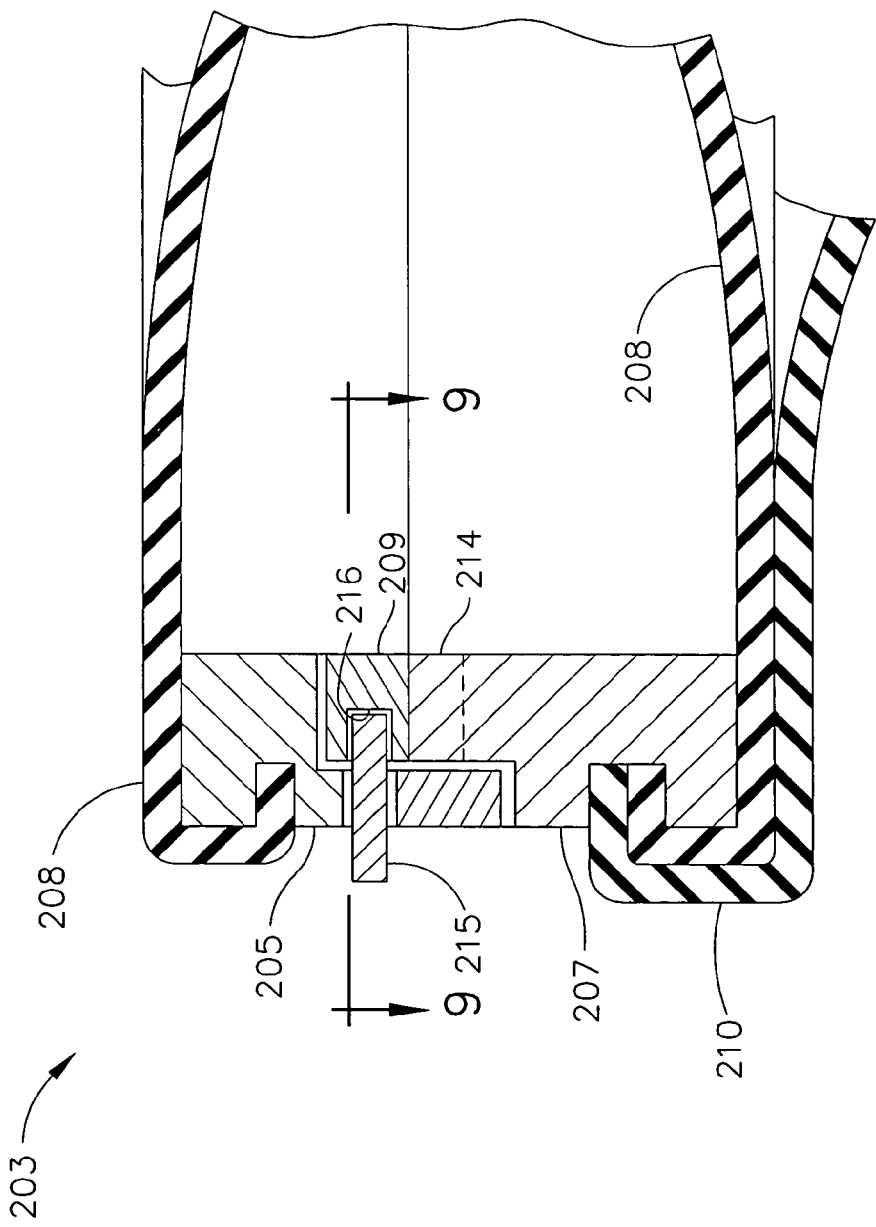

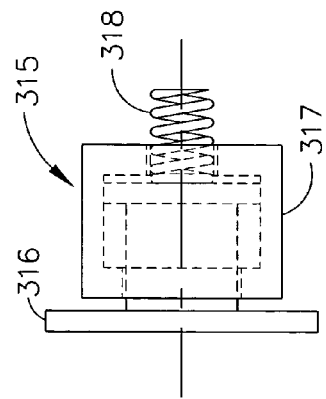
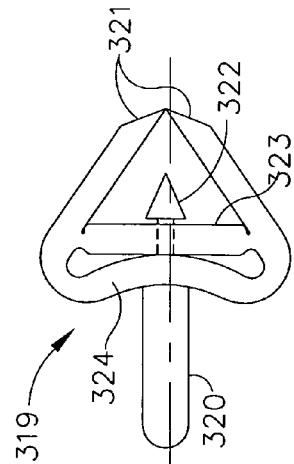
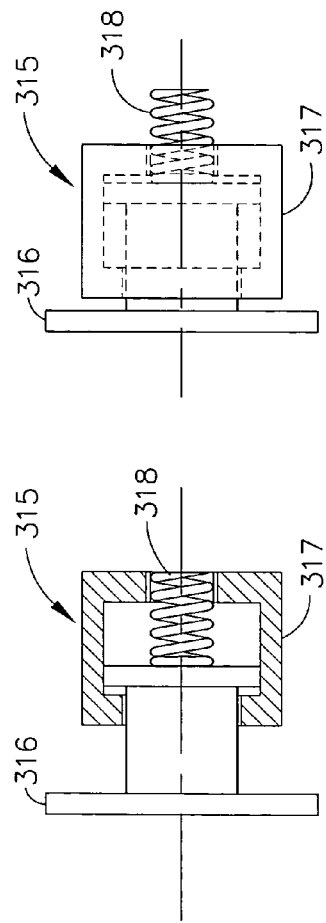
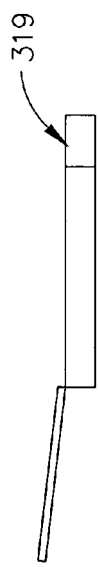
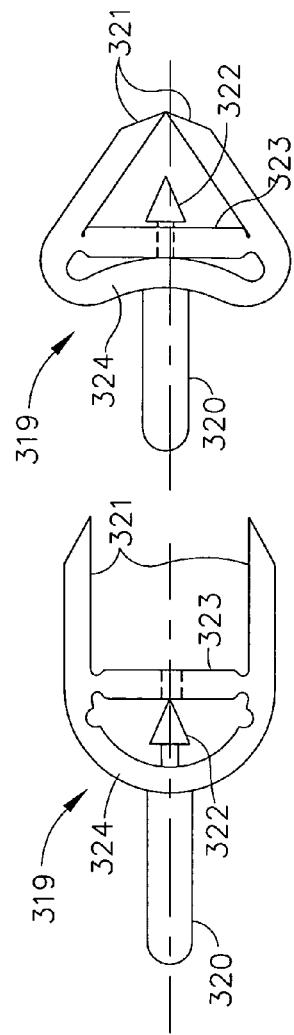
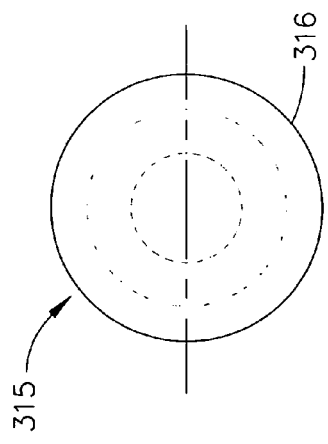
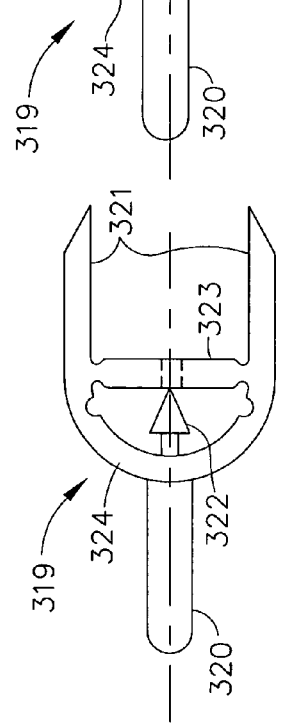

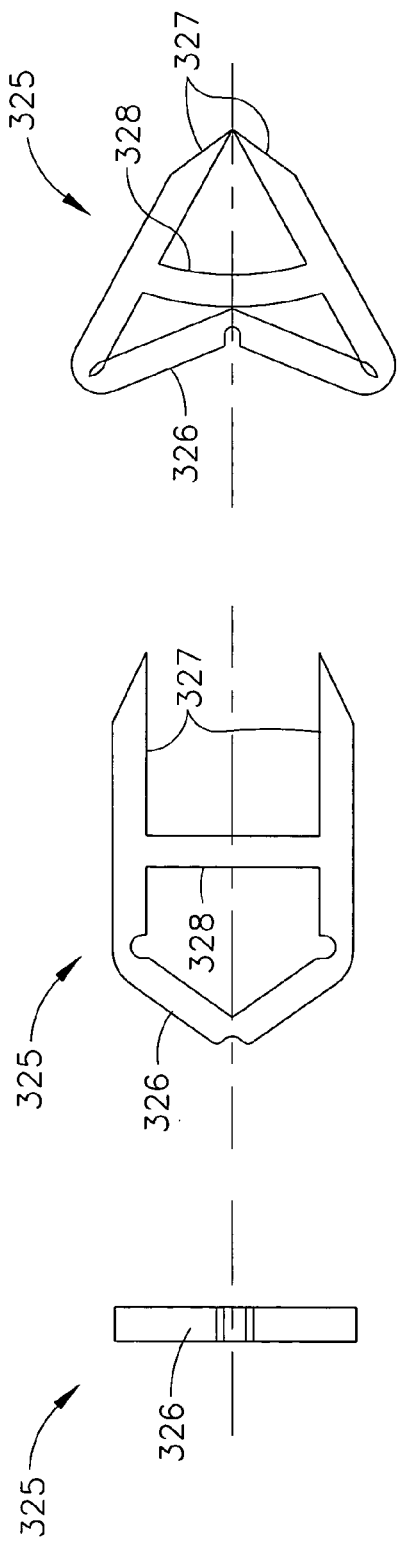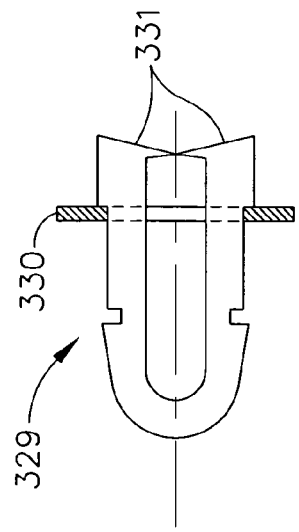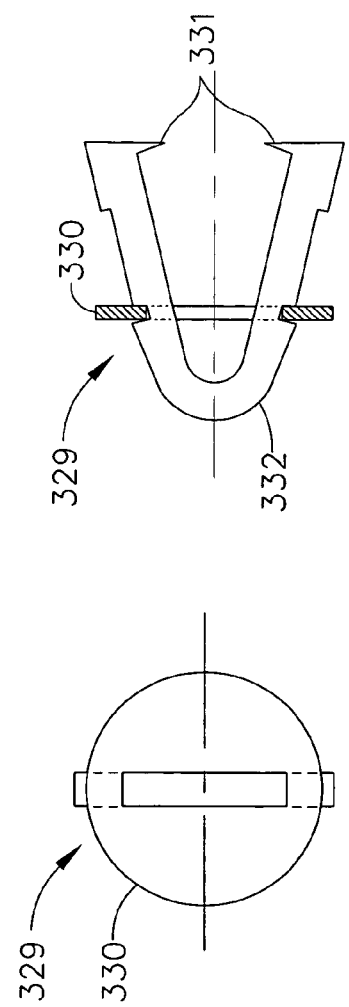
FIG. 3-19
FIG. 3-20
FIG. 3-21
FIG. 3-22
FIG. 3-23
FIG. 3-24

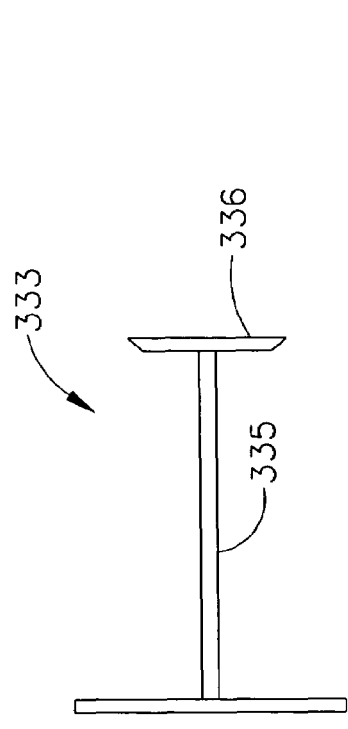
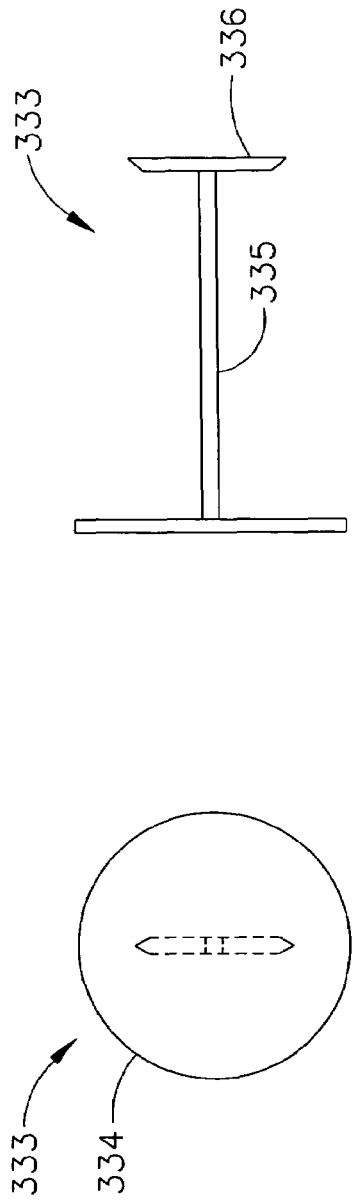
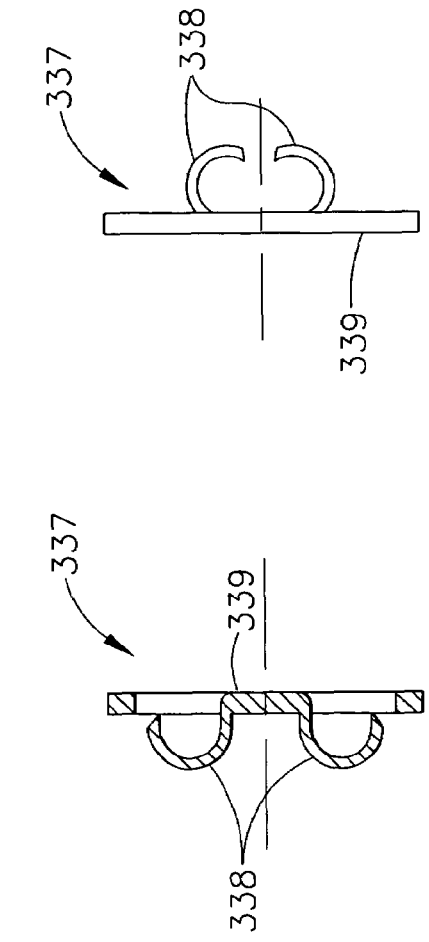
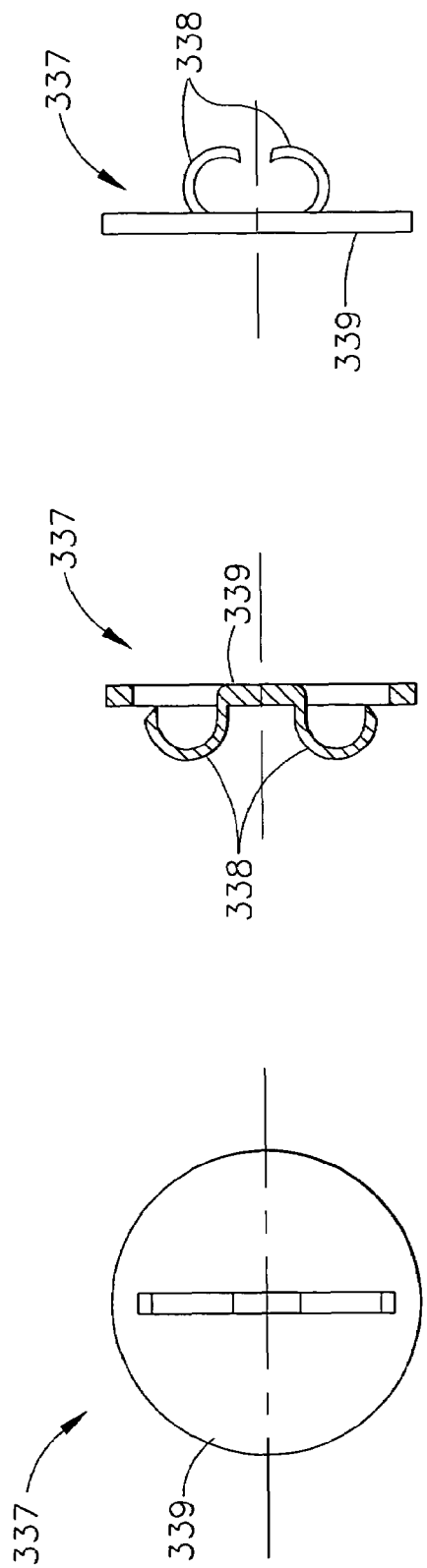

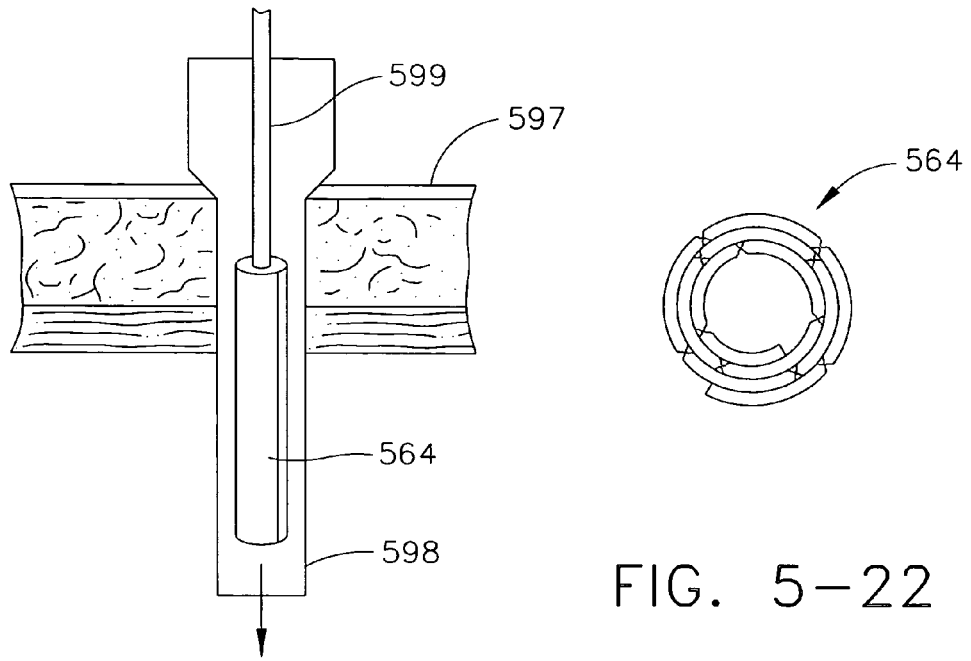
FIG. 5-21
FIG. 5-22
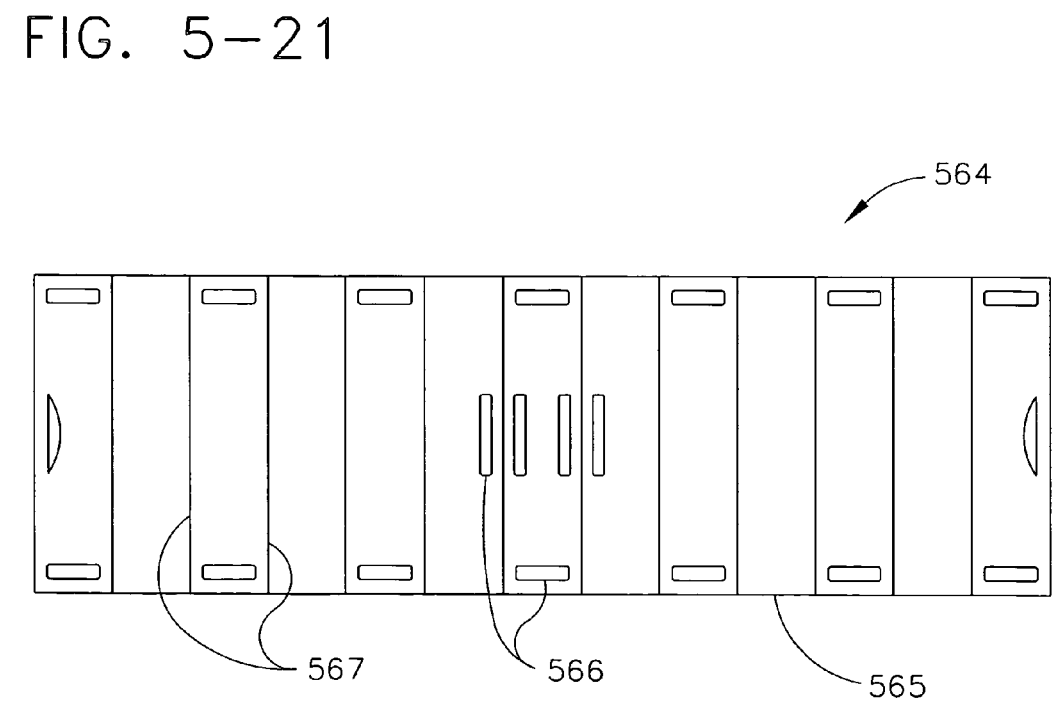
FIG. 5-23

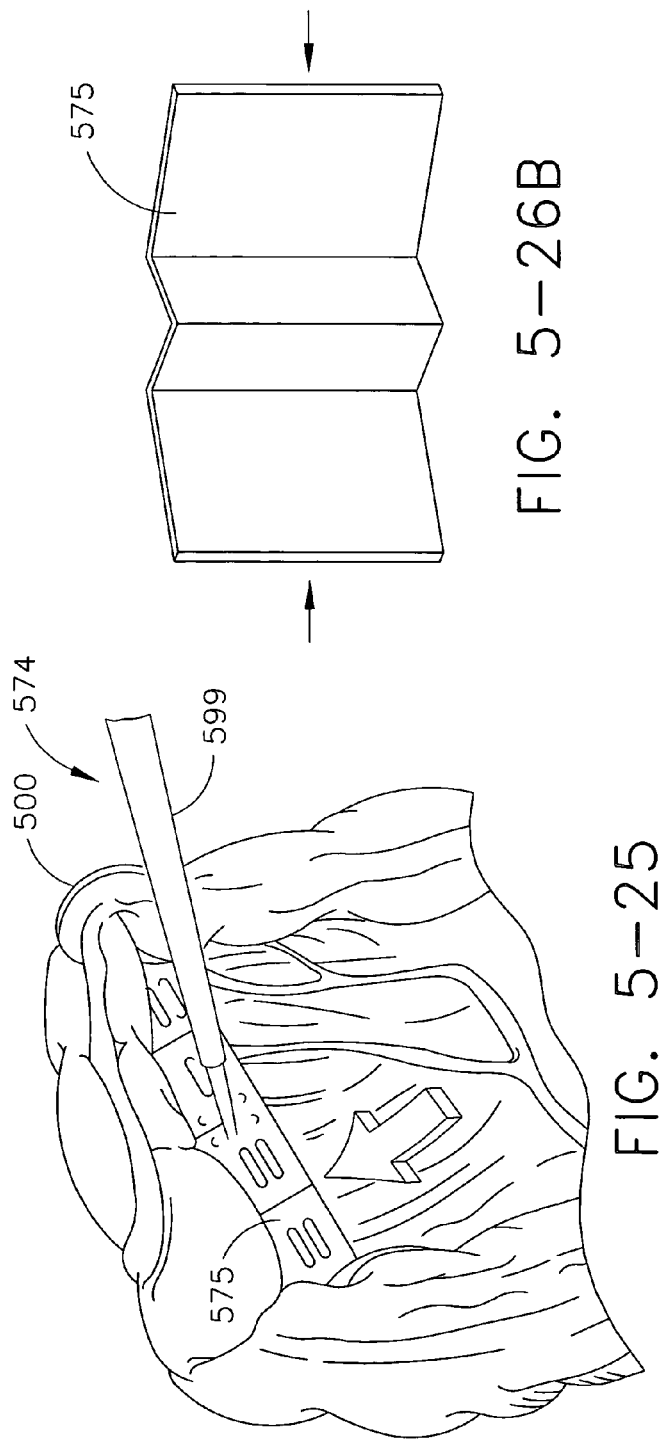

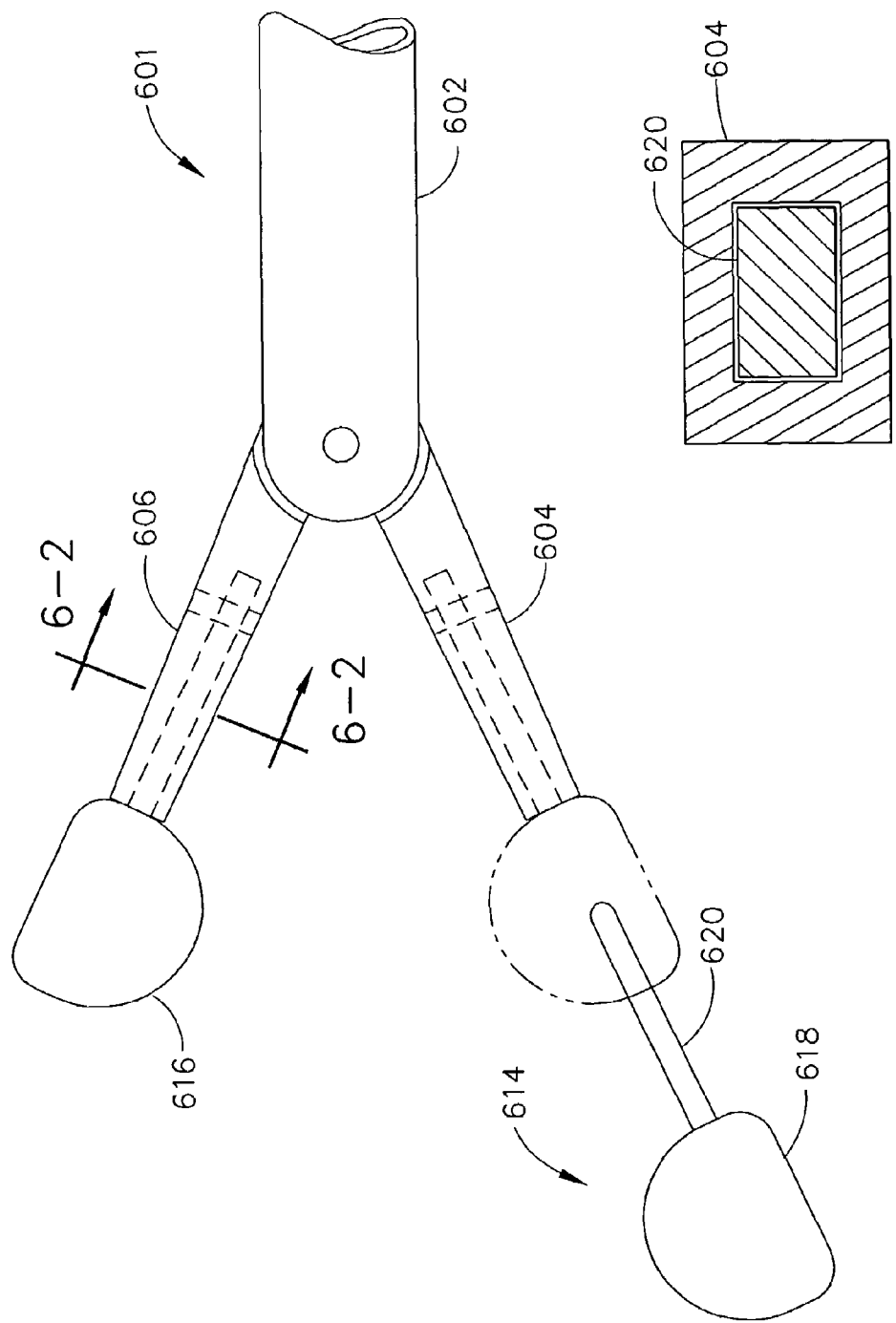

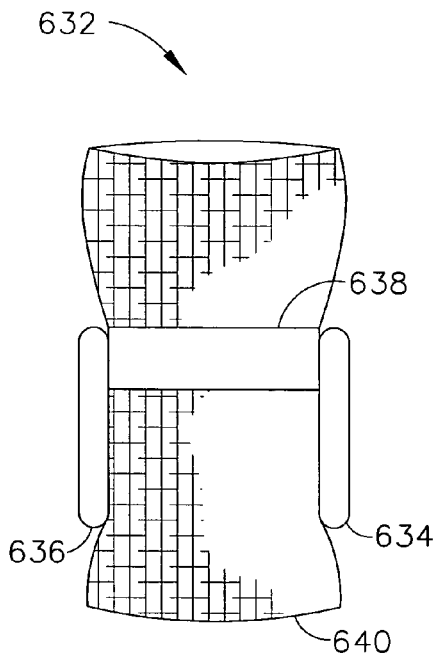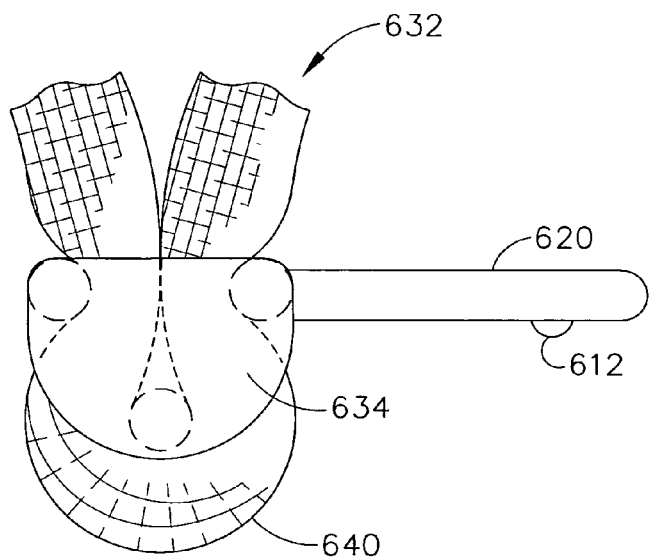
FIG. 6-5  FIG. 6-6
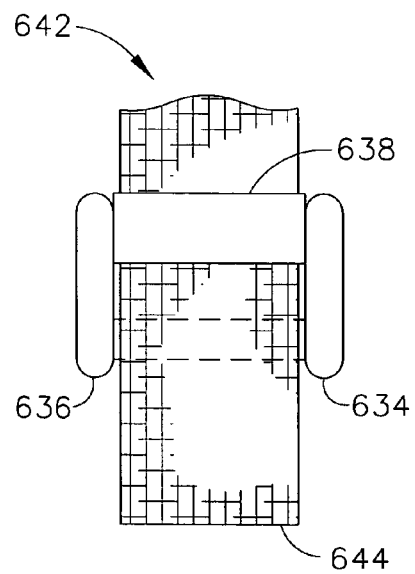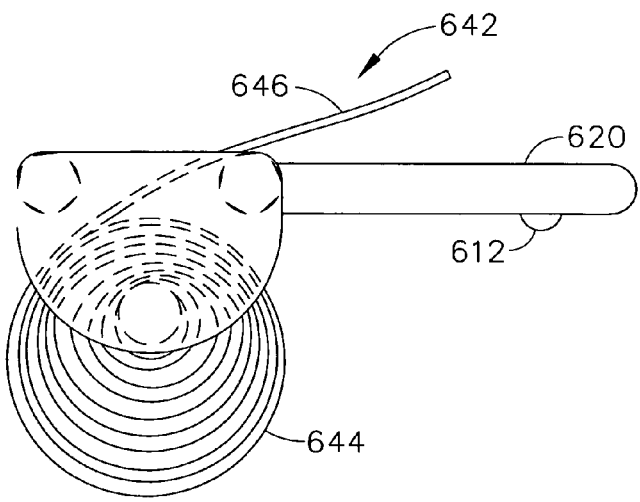
FIG. 6-7  FIG. 6-8

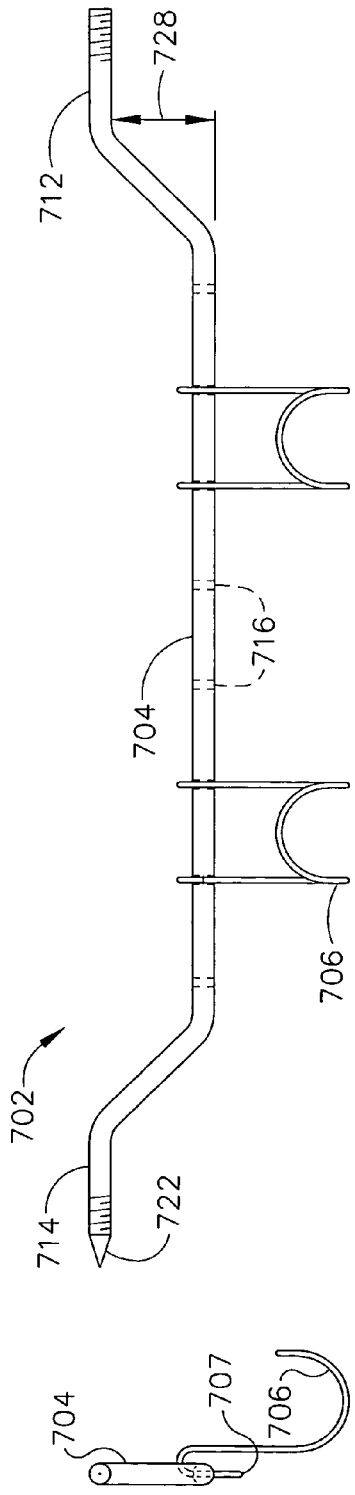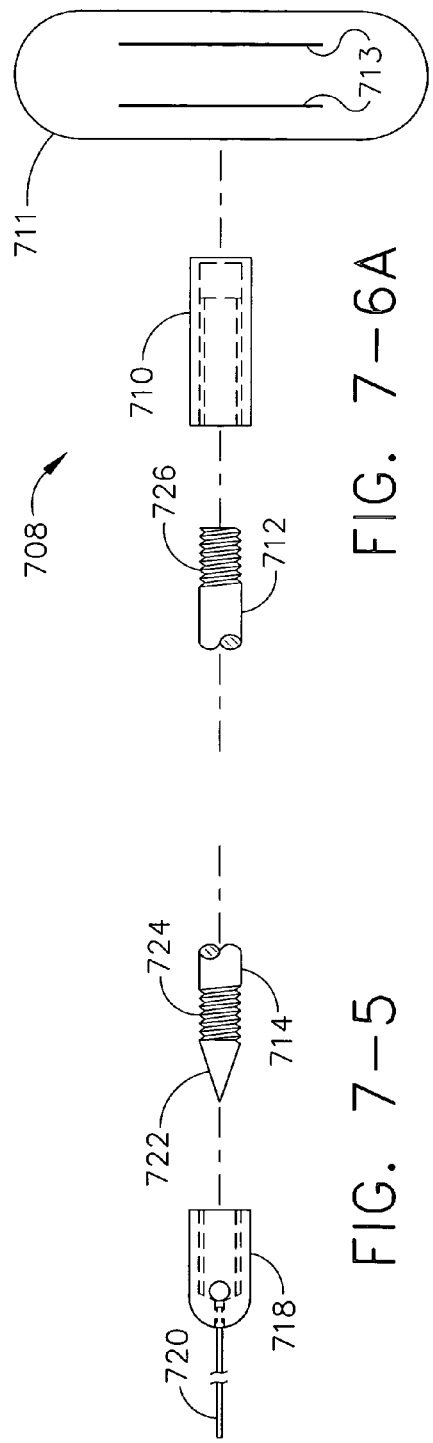
FIG. 7-4
FIG. 7-3
FIG. 7-6A
FIG. 7-5

MULTI-PORT LAPAROSCOPIC ACCESS DEVICE

REFERENCE TO RELATED APPLICATIONS

The present application claims the priority benefit of U.S. provisional patent application Ser. Nos. 60/669,514, filed on Apr. 8, 2005, and 60/700,176, filed on Jul. 18, 2005, both of which are incorporated herein by reference.

This application contains subject matter that relates to and incorporates by reference in their entirety, for any and all purposes, the following non-provisional applications:

SURGICAL ACCESS DEVICE, Ser. No. 11/399,172, filed Apr. 5, 2006;

TISSUE MARKER AND METHOD FOR USE, Ser. No. 11/399,045, filed Apr. 5, 2006;

INTRA-ABDOMINAL STORAGE DEVICE, Ser. No. 11/399,044, filed Apr. 5, 2006;

TISSUE RETRACTION DEVICE, Ser. No. 11/399,149, filed Apr. 5, 2006;

SURGICAL INSTRUMENT SYSTEM, Ser. No. 11/399,145, filed Apr. 5, 2006; and

TISSUE SUSPENSION DEVICE, Ser. No. 11/399,181, filed Apr. 5, 2006.

FIELD OF THE INVENTION

The present application relates to methods and devices for laparoscopic surgical procedures and, more particularly, to hand-assisted, laparoscopic procedures.

BACKGROUND

In a minimally invasive, laparoscopic surgical procedure, a surgeon may place a number of small ports into the abdomen to gain access into the abdominal cavity of the patient. A surgeon may use, for example, a port for insufflating the abdominal cavity to create space, a port for introducing a laparoscope for viewing, and a number of other ports for introducing surgical instruments for operating on tissue. The benefits of minimally invasive procedures compared to open surgery procedures for treating certain types of wounds and diseases are now well-known to include faster recovery time and less pain for the patient, better outcomes, and lower overall costs.

In traditional, open surgery, surgeons may use their hands, together with surgical instrumentation, to manipulate tissues, to perform particular steps of the procedure and to obtain tactile feedback through their fingertips to verify the nature of particular tissues. Also in open surgery, the size and shape of instruments that a surgeon may place into the abdominal cavity, as well as the size and shape of tissues that a surgeon may remove, obviously is not nearly as limited as in laparoscopic surgery.

Hand-assisted, laparoscopic surgery ("HALS") combines some of the benefits of both the open and the laparoscopic methods. In a HALS procedure, a surgeon still places small ports into the abdomen to insufflate, to view and to introduce instruments into the abdominal cavity. In a HALS procedure, however, a surgeon also creates an incision into the abdominal wall large enough to accommodate the surgeon's hand. The incision may be retracted and draped to provide a suitably sized and protected opening. A surgeon may also place a laparoscopic access device, also referred to as a lap disc, into the incision to maintain insufflation in the abdominal cavity while the surgeon's hand is either inserted into the cavity though the device or removed from the cavity. The advent of HALS and the lap disc creates numerous opportunities for creating and/or improving surgical devices and methods.

SUMMARY

A surgical access device is provided for surgical access through an incision in the body wall to the inside of a body cavity of a patient. A multi-port insert is provided for use with a laparoscopic access device. The multi-port insert includes a base having two or more ports or apertures that provide for the insertion of surgical instruments. The multi-port insert 100 may be used with a laparoscopic access device, such as a Lap Disc Hand Access Device model #LD111, commercially available from Ethicon Endo-Surgery, Inc. of Cincinnati, Ohio. The multi-port insert provides for the insertion of one or more surgical instruments through the laparoscopic access device. Each port or aperture in the base includes its own seal assembly to provide a seal and prevent the escape of insufflation gases.

In one embodiment the multi-port insert may also include one or more instrument supports that are attached to the base to fix the position of one or more surgical instruments inserted through the multi-port insert.

A method is also provided for accessing a body cavity of a patient during a surgical procedure. The method includes providing an access device that includes a subassembly having a multi-port insert. The access device is positionable in the incision and defines a passageway through the body wall between the opening in the subassembly and the body cavity. The surgical access device further includes at least two access channels for insertion of one or more surgical instruments through the access device. The method further includes providing at least one instrument support on the access device for supporting one or more surgical instruments inserted through the multi-port insert.

BRIEF DESCRIPTION OF THE DRAWINGS

The novel features of the invention are set forth with particularity in the appended claims. The invention itself, however, both as to organization and methods of operation, may best be understood by reference to the following description, taken in conjunction with the accompanying drawings in which:

FIG. 1-2 is a top view of the base of FIG. 1-1;

FIG. 1-3 is a sectional side view of a first aspect of a seal assembly for use with the base of FIG. 1-1;

FIG. 1-4 is a top view of the seal assembly of FIG. 1-3;

FIG. 1-5 is a sectional side view of a first embodiment of the base of FIG. 1-1;

FIG. 1-6 is a sectional side view of an alternate embodiment of the base of FIG. 1-5;

FIG. 1-7 is a sectional side view of a laparoscopic access device including the base of FIG. 1-5;

FIG. 1-8 is an expanded cross-sectional view of an instrument support;

FIG. 1-9 is a view of the instrument support of FIG. 1-8 in an assembled state;

FIG. 1-10 is a sectional view of an alternate embodiment of an instrument support;

FIG. 1-11 is a sectional view of a third embodiment of an instrument support;

FIG. 1-12 is a sectional view of a fourth embodiment of an instrument support;

FIG. 2-1 is a partially sectioned front view of an access device of the prior art;

FIG. 2-2 is a partially sectioned front view of a first aspect of an access device;

FIG. 2-3 is a top view of the access device shown in FIG. 2-2;

FIG. 2-4 is a sectional view of a port of the access device shown in FIG. 2-3;

FIG. 2-5 is a partially sectioned front view of a second aspect of an access device;

FIG. 2-6 is a top view of the access device shown in FIG. 2-5;

FIG. 2-7 is schematic representation of a third aspect of an access device;

FIG. 2-8 is a partial side view of a fourth aspect of an access device;

FIG. 2-9 is a partial top view, taken at line 9-9 of FIG. 2-10, of the access device shown in FIG. 2-8;

FIG. 2-10 is a partial front, sectional view taken at line 10-10 of FIG. 2-9, of the access device shown in FIG. 2-8;

FIG. 3-1 is a top view of a first aspect of a tissue marker;

FIG. 3-2 is a side view of the tissue marker shown in FIG. 3-1, while in a flat configuration;

FIG. 3-3 is a side view of the tissue marker shown in FIG. 3-1, while in a deployed configuration;

FIG. 3-4 is a sectional view of the tissue marker shown in FIG. 3-1 being attached to tissue;

FIG. 3-5A is a perspective view of two tissue markers of FIG. 3-1, each including a flag and attached to tissue;

FIG. 3-5B is a perspective view of the tissue marker shown in FIG. 3-1, but with an alternate embodiment of a flag, shown in a non-extended position;

FIG. 3-5C is a perspective view of the tissue marker shown in FIG. 3-5B, with the flag shown in an extended position;

FIG. 3-6 is a top view of a second aspect of a tissue marker;

FIG. 3-7 is a side view of the tissue marker shown in FIG. 3-6, shown before deployment;

FIG. 3-8 is a side sectional view of the tissue marker shown in FIG. 3-6, shown after deployment;

FIG. 3-9 is a top view of a third aspect of a tissue marker;

FIG. 3-10 is a side sectional view of the tissue marker shown in FIG. 3-9; shown before deployment;

FIG. 3-11 is a side view of the tissue marker shown in FIG. 3-9, shown after deployment;

FIG. 3-12 is a top view of a fourth aspect of a tissue marker;

FIG. 3-13 is a side sectional view of the tissue marker shown in FIG. 3-12, shown before deployment;

FIG. 3-14 is a side view of the tissue marker shown in FIG. 3-12, shown after deployment;

FIG. 3-15 is a side view of a fifth aspect of a tissue marker;

FIG. 3-16 is an end view of the tissue marker shown in FIG. 3-15;

FIG. 3-17 is a front view of the tissue marker shown in FIG. 3-15, shown before deployment;

FIG. 3-18 is a front view of the tissue marker shown in FIG. 3-15, shown after deployment;

FIG. 3-19 is an end view of a sixth aspect of a tissue marker;

FIG. 3-20 is a front view of the tissue marker shown in FIG. 3-19, shown before deployment;

FIG. 3-21 is a front view of the tissue marker shown in FIG. 3-19, shown after deployment;

FIG. 3-22 is a top view of a seventh aspect of a tissue marker;

FIG. 3-23 is a front view of the tissue marker shown in FIG. 3-22, shown before deployment;

FIG. 3-24 is a front view of the tissue marker shown in FIG. 3-22, shown after deployment;

FIG. 3-25 is a top view of an eighth aspect of a tissue marker;

FIG. 3-26 is a side view of the tissue marker shown in FIG. 3-25;

FIG. 3-27 is a top view of a ninth aspect of a tissue marker;

FIG. 3-28 is a side view of the tissue marker shown in FIG. 3-27, shown before deployment;

FIG. 3-29 is a side view of the tissue marker shown in FIG. 3-27, shown after deployment;

FIG. 3-30 is a top view of a tenth aspect of a tissue marker;

FIG. 3-31 is a side view of the tissue marker shown in FIG. 3-30, shown before deployment;

FIG. 3-32 is a side view of the tissue marker shown in FIG. 3-30, shown after deployment;

FIG. 3-33 is a side view of a first embodiment of a marking fluid applier;

FIG. 3-34 is a partial side view of a second embodiment of a marking fluid applier;

FIG. 3-35 is a partial top view of the marking fluid applier shown in FIG. 3-34;

FIG. 3-36 is an enlarged view of a tissue interfacing surface of the marking fluid applier shown in FIG. 3-34;

FIG. 3-37 is an illustration of a plurality of tissue markings on the colon of a surgical patient;

FIG. 3-38 is an illustration of a tissue marker being deployed onto tissue with a surgical instrument;

FIG. 3-39 is an illustration of a marking fluid being applied to tissue;

FIG. 3-40 is an illustration of a colon of a surgical patient prior to resection;

FIG. 3-41 is an illustration of a colon of a surgical patient during resection;

FIG. 3-42 is an illustration of a colon of a surgical patient after resection;

FIG. 4-1 is a perspective view of a first aspect of a storage device;

FIG. 4-2 is a perspective view of a second aspect of a storage device;

FIG. 4-3 is a perspective view of a third aspect of a storage device;

FIG. 4-4 is a perspective view of a fourth aspect of a storage device;

FIG. 4-5 is a perspective view of a storage device, including a first embodiment of an attaching element;

FIG. 4-6 is a perspective view of a storage device, including a second embodiment of an attaching element;

FIG. 4-7 is a perspective view of a storage device, including a third embodiment of an attaching element;

FIG. 4-8 is a perspective view of a storage device, including a fourth embodiment of an attaching element;

FIG. 4-9 illustrates a storage device positioned against the inside of the body wall of the patient;

FIG. 4-10 illustrates a storage device removably attached to a trocar cannula, which is positioned through the body wall of the patient;

FIG. 4-11 illustrates a storage device in a closed configuration and removably attached to the trocar cannula, which is positioned through the body wall of the patient;

FIG. 4-12 illustrates a storage device in an open configuration and positioned inside the body cavity, and prior to the removable attachment of a cap onto an attaching rod;

FIG. 4-13 illustrates a storage device in a closed configuration and positioned inside the body cavity, and after the removable attachment of the cap onto the attaching rod;

FIG. 5-1 illustrates a first aspect of a surgical retraction device retracting the colon of a surgical patient;

FIG. 5-2 is a perspective view of a second aspect of a retraction device;

FIG. 5-3 is a perspective view of a third aspect of a retraction device;

FIG. 5-4 is a perspective view of a fourth aspect of a retraction device, while in a closed configuration;

FIG. 5-5 is a perspective view of the retraction device shown in FIG. 5-4, while in an opened configuration;

FIG. 5-6 is a perspective view of a fifth aspect of a retraction device; while in a closed configuration;

FIG. 5-7 is a perspective view of the retraction device shown in FIG. 5-6, while in an opened configuration;

FIG. 5-8 is a perspective view of a sixth aspect of a retraction device;

FIG. 5-9 is a perspective view of an seventh aspect of a retraction device;

FIG. 5-10 illustrates an eighth aspect of a retraction device retracting the colon of a surgical patient;

FIG. 5-11 illustrates a ninth aspect of a retraction device retracting the colon of a surgical patient;

FIG. 5-12 is a perspective view a tenth aspect of a retraction device in a closed configuration;

FIG. 5-13A is a perspective view the retraction device shown in FIG. 5-12, while in a partially open configuration;

FIG. 5-13B is a perspective view the retraction device shown in FIG. 5-12, while in an open configuration;

FIG. 5-14 is a perspective view of an eleventh aspect of a retraction device;

FIG. 5-15 is a perspective view of a twelfth aspect of a retraction device;

FIG. 5-16 is a side view of a thirteenth aspect of a retraction device while in an opened configuration;

FIG. 5-17 is a side view of the retraction device shown in FIG. 5-16, while in a partially opened configuration;

FIG. 5-18 is a side view of the retraction device shown in FIG. 5-1,6 while in a closed configuration;

FIG. 5-19 illustrates a fourteenth aspect of a retraction device retracting the colon of a surgical patient;

FIG. 5-20 is a perspective view of an arm of the retraction device shown in FIG. 5-19;

FIG. 5-21 is a sectional view of a fifteenth aspect of a retraction device, while in a closed configuration and being passed through a laparoscopic port;

FIG. 5-22 is an end view of the retraction device shown in FIG. 5-21, while in the closed configuration;

FIG. 5-23 is a front view of the retraction device shown in FIG. 5-21, while in the closed configuration;

FIG. 5-24 is a front view of a sixteenth aspect of a retraction device;

FIG. 5-25 illustrates an seventeenth aspect of a retraction device retracting the colon of a surgical patient;

FIG. 5-26A is a front view of the retraction device shown in FIG. 5-25, while in an open configuration;

FIG. 5-26B is a front view of the retraction device shown in FIG. 5-25, while in a partially closed configuration;

FIG. 5-27 illustrates an eighteenth aspect of a retraction device retracting the colon of a surgical patient;

FIG. 5-28 illustrates a nineteenth aspect of a retraction device retracting the colon of a surgical patient;

FIG. 5-29 is a perspective view of a twentieth aspect of a retraction device;

FIG. 5-30 is a front view of a twenty-first aspect of a retraction device, while in a first, partially closed configuration;

FIG. 5-31 is a front view of the retraction device shown in FIG. 5-30, while in a second, partially closed configuration;

FIG. 5-32 is a front view of the retraction device shown in FIG. 5-30, while in an opened configuration;

FIG. 5-33 is a top view of a twenty-second aspect of a retraction device;

FIG. 5-34 is a front view of the retraction device shown in FIG. 5-33;

FIG. 5-35 is a top view of a twenty-third aspect of a retraction device;

FIG. 5-36 is a front view of the retraction device shown in FIG. 5-35;

FIG. 5-37A is a top view of a twenty-fourth aspect of a retraction device;

FIG. 5-37B is a detailed, top view of the retraction device shown in FIG. 5-37A, while being rolled up into a closed configuration;

FIG. 5-38 is a front view of the retraction device shown in FIG. 5-37;

FIG. 5-39 is a top view of a twenty-fifth aspect of a retraction device;

FIG. 5-40 is a front view of the retraction device shown in FIG. 5-39;

FIG. 5-41 is an end view of the retraction device shown in FIG. 5-39;

FIG. 5-42 is a front view of a twenty-sixth aspect of a retraction device;

FIG. 5-43 is a front view of the retraction device shown in FIG. 5-42, while in a twisted configuration;

FIG. 5-44 is a top view of a twenty-seventh aspect of a retraction device;

FIG. 5-45 is a front view of the retraction device shown in FIG. 5-44;

FIG. 5-46 is a top view of a twenty-eighth aspect of a retraction device;

FIG. 5-47 is a front view of the retraction device shown in FIG. 5-46;

FIG. 5-48 is a top view of a twenty-ninth aspect of a retraction device;

Figure 1:
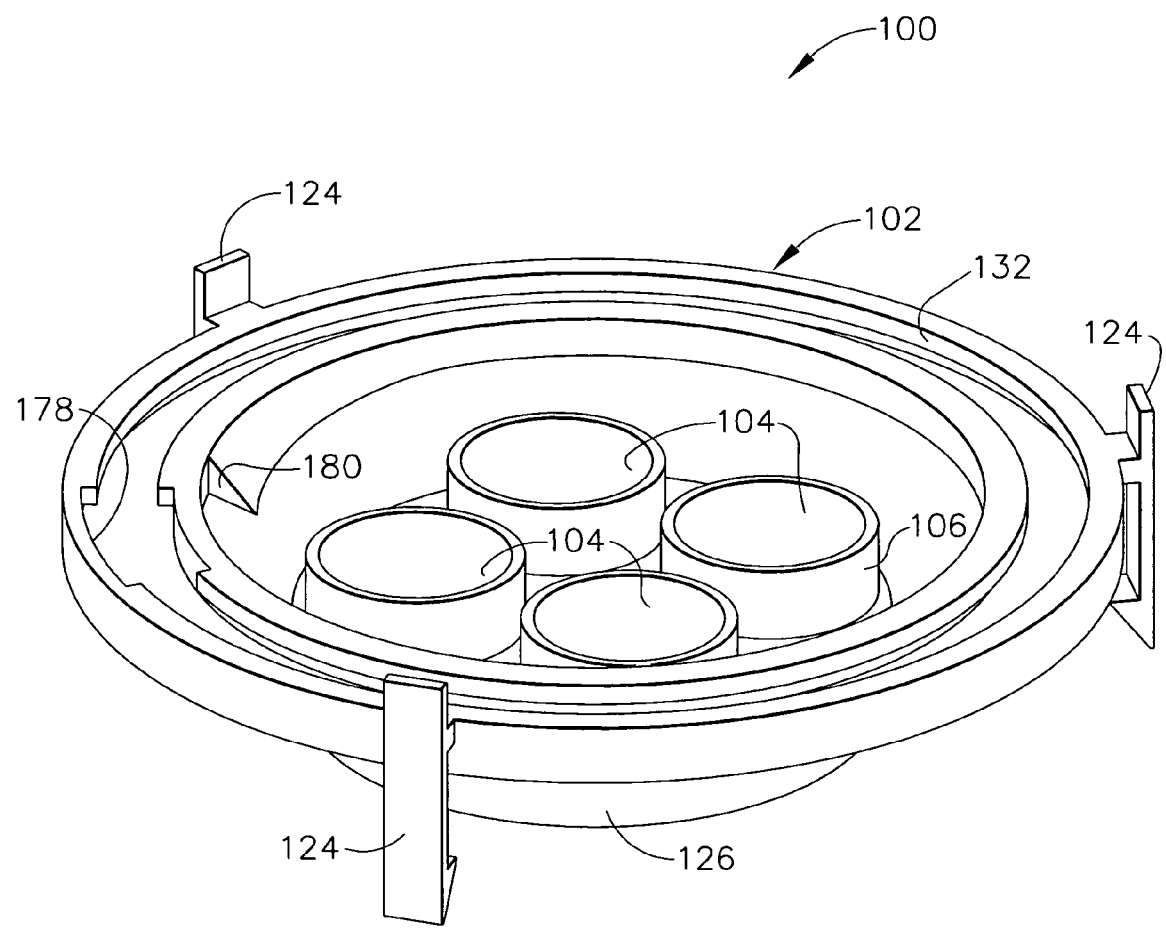
FIG. 1-1 is a perspective view of a first aspect of a base.
Figures 1, 2:
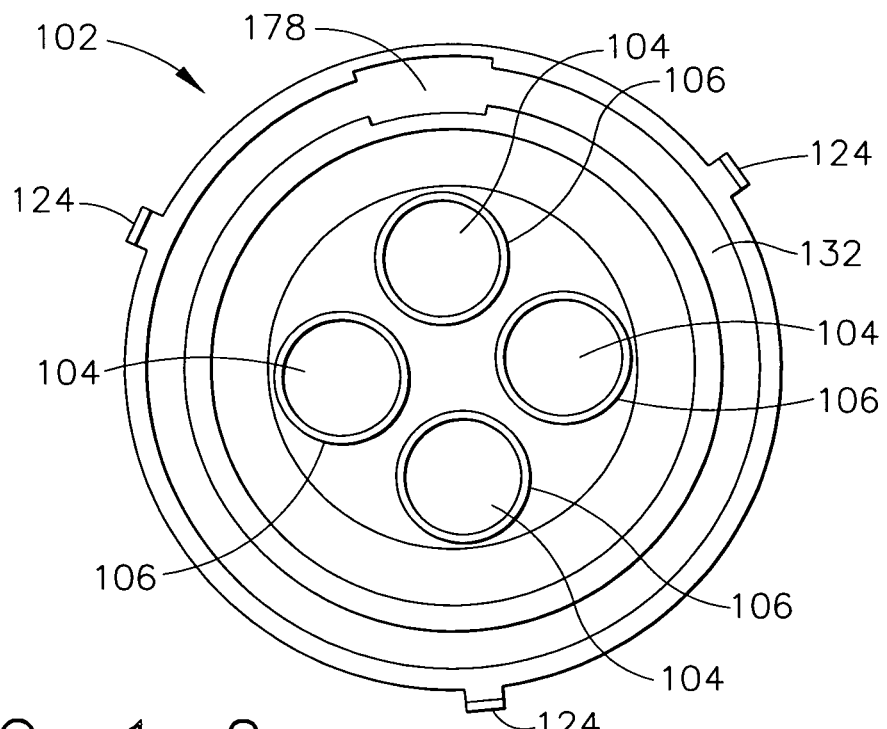
Figures 1, 2, 3:
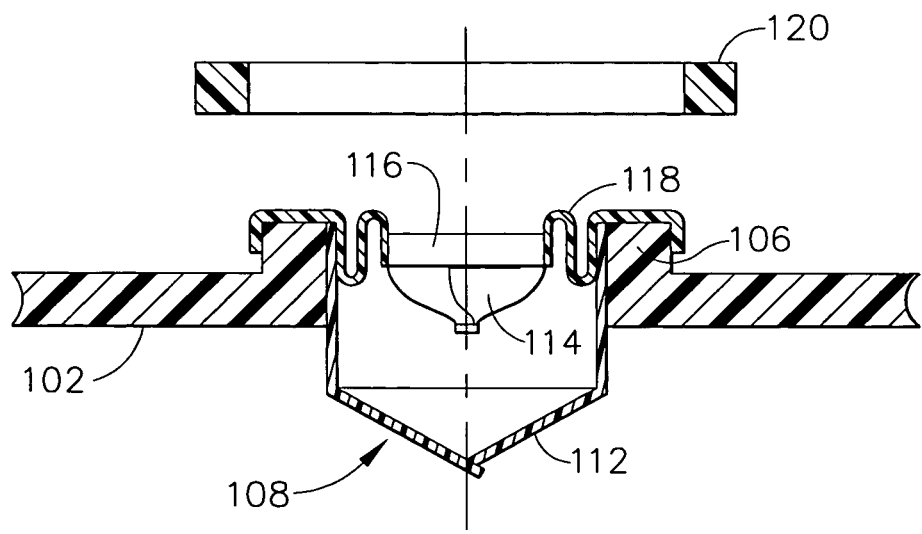
Figures 1, 2, 3, 4:
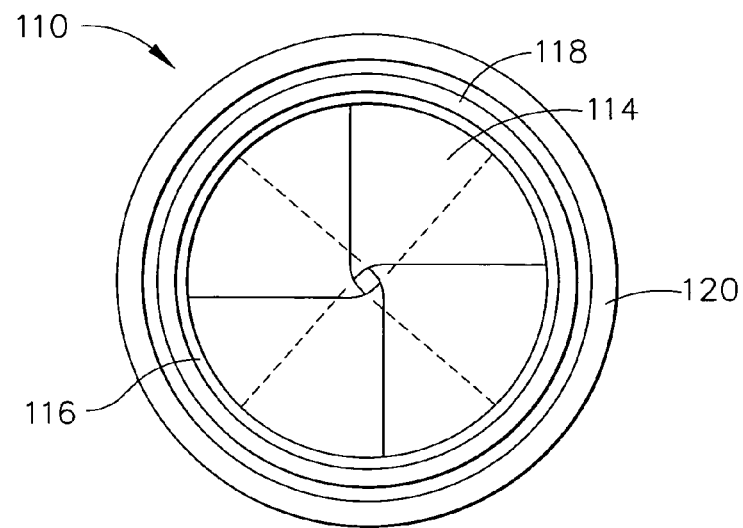
Figures 1, 2, 3, 4, 5:
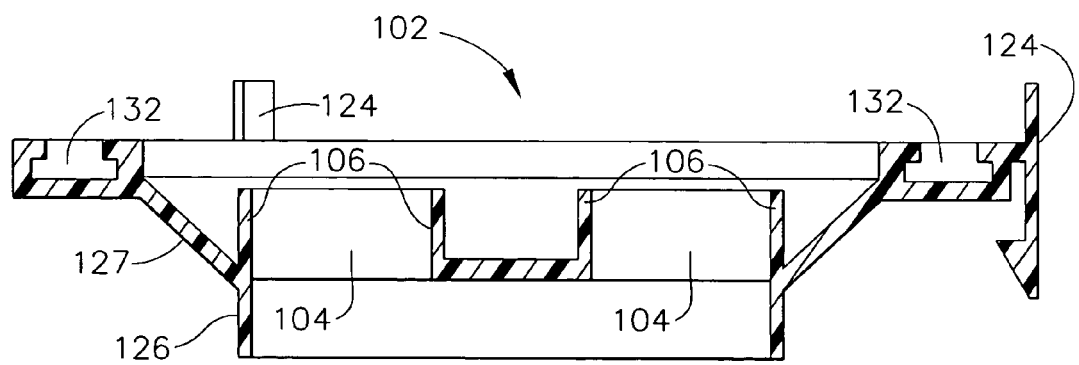
Figures 1, 2, 3, 4, 5, 6:
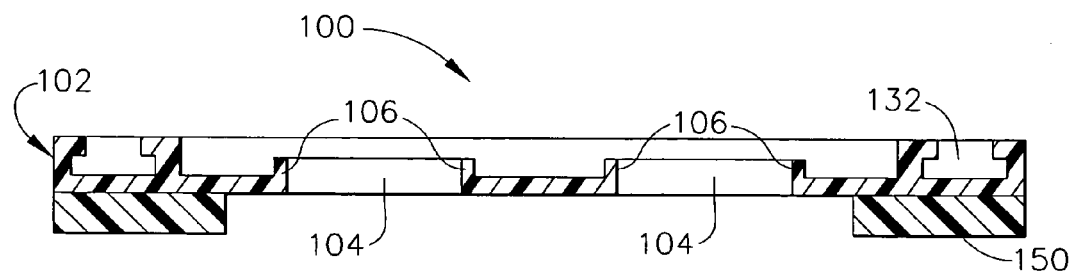
Figures 1, 2, 3, 4, 5, 6, 7:
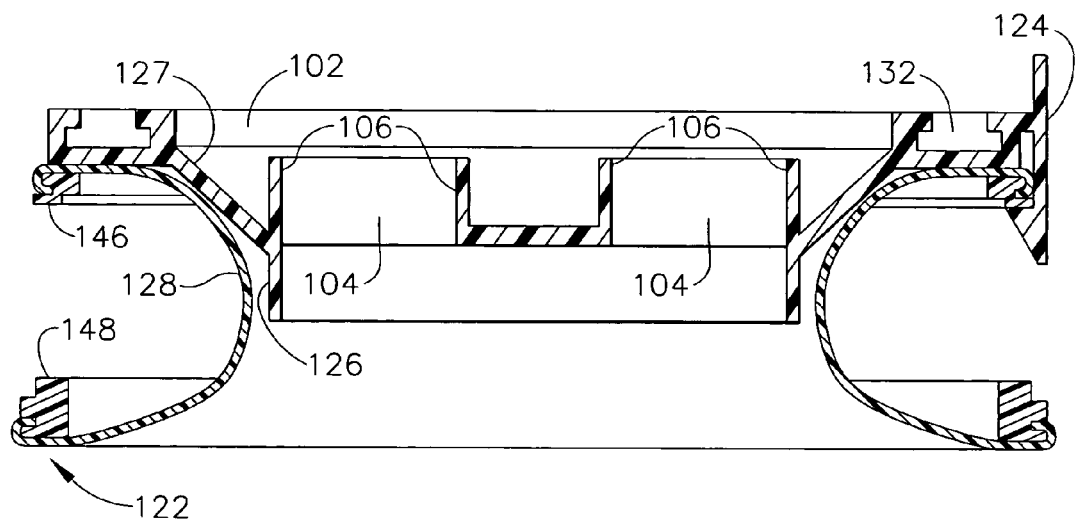
Figures 1, 2, 3, 4, 5, 6, 7, 8:
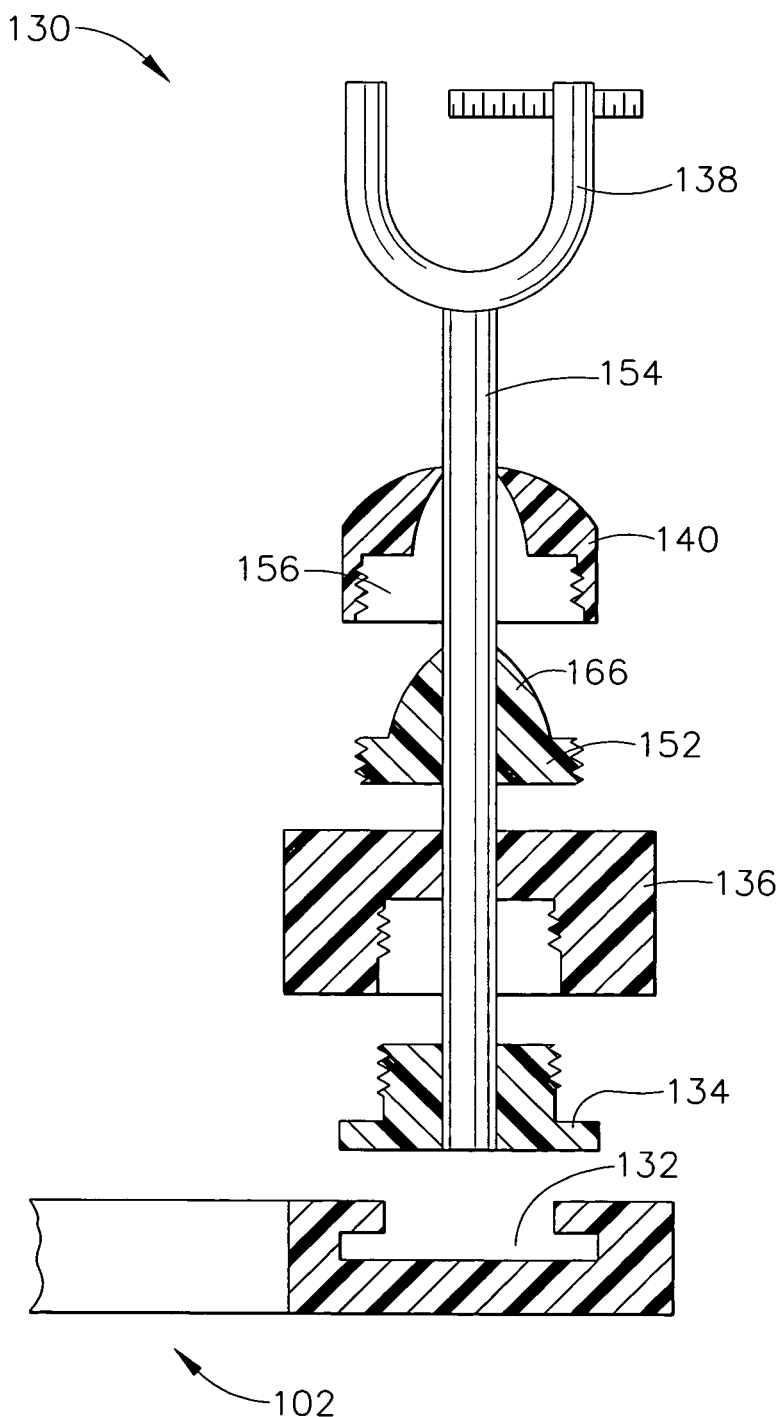
Figures 1, 2, 3, 4, 5, 6, 7, 8, 9:
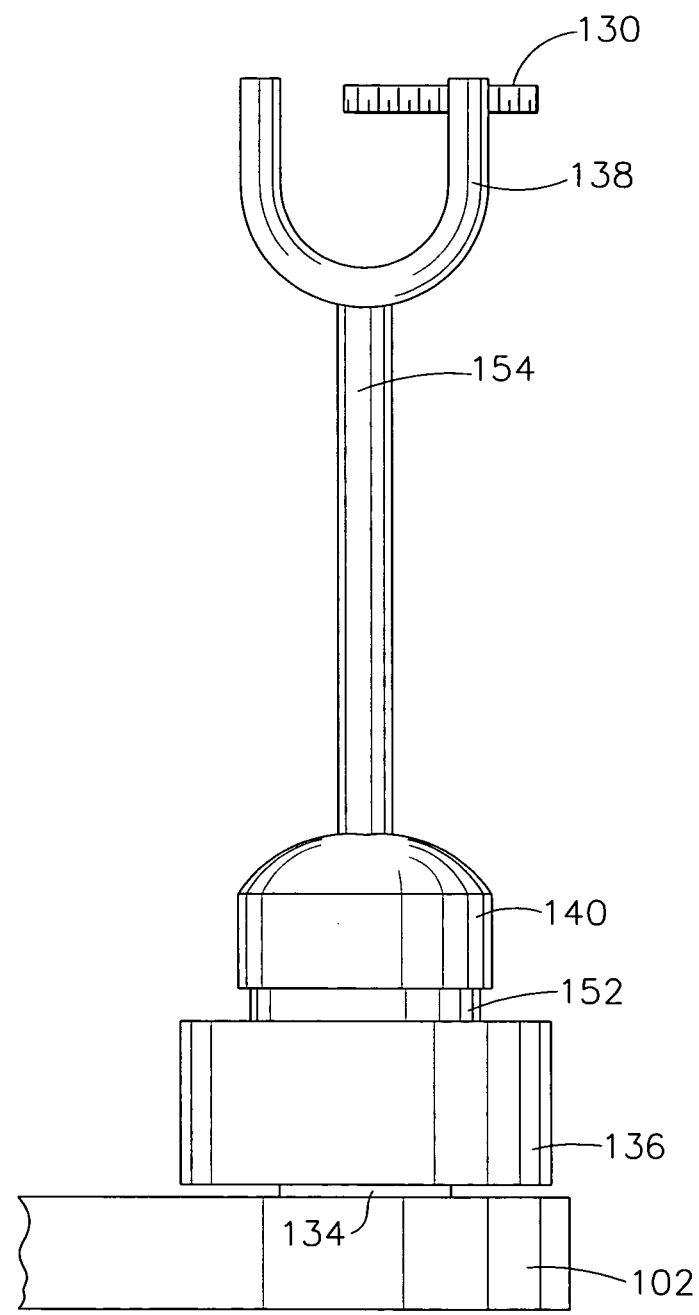
Figures 1, 2, 3, 4, 5, 6, 7, 8, 9, 10:
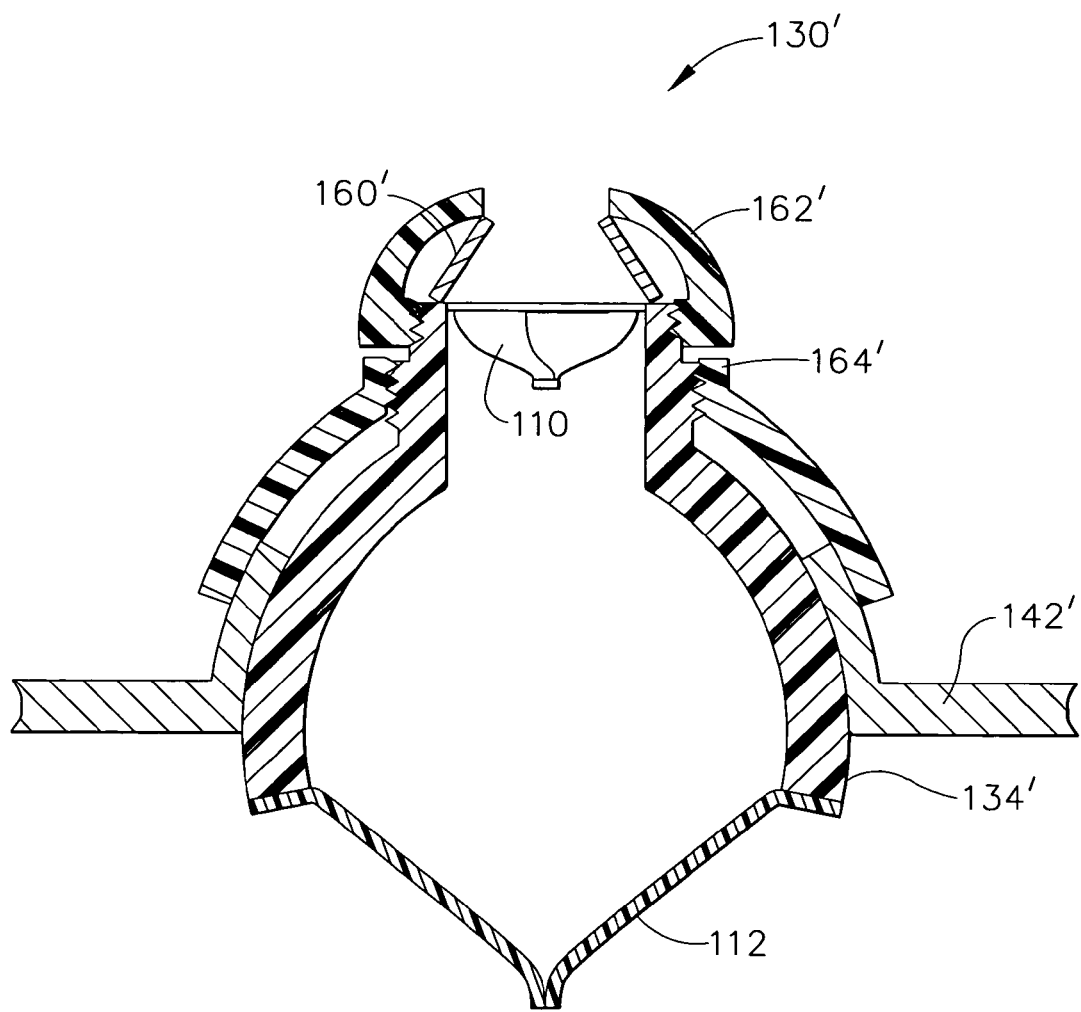
Figures 1, 2, 3, 4, 5, 6, 7, 8, 9, 10, 11:
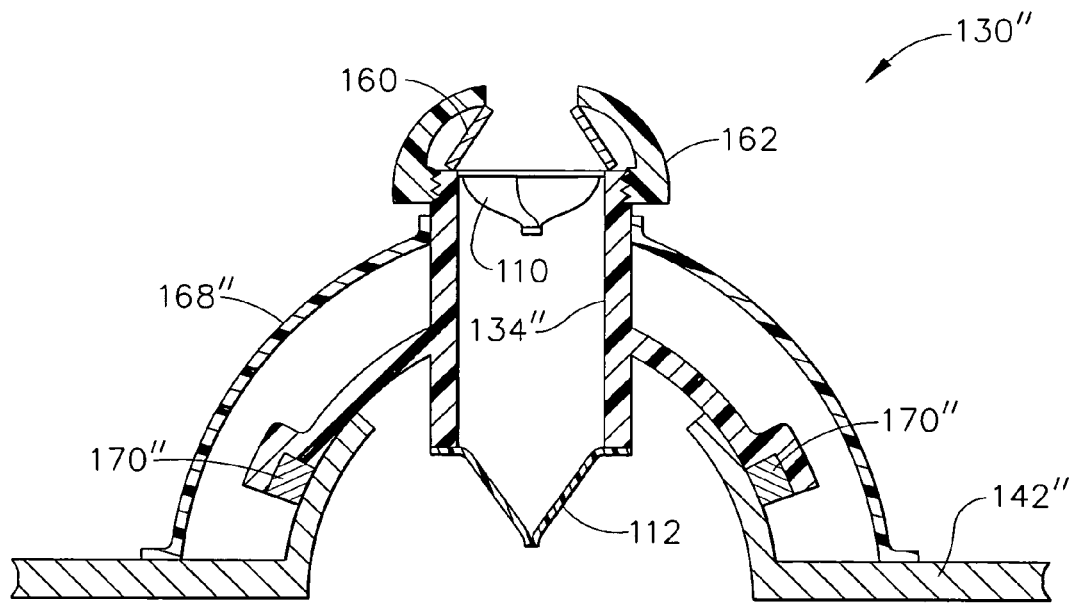
Figures 1, 2, 3, 4, 5, 6, 7, 8, 9, 10, 11, 12:
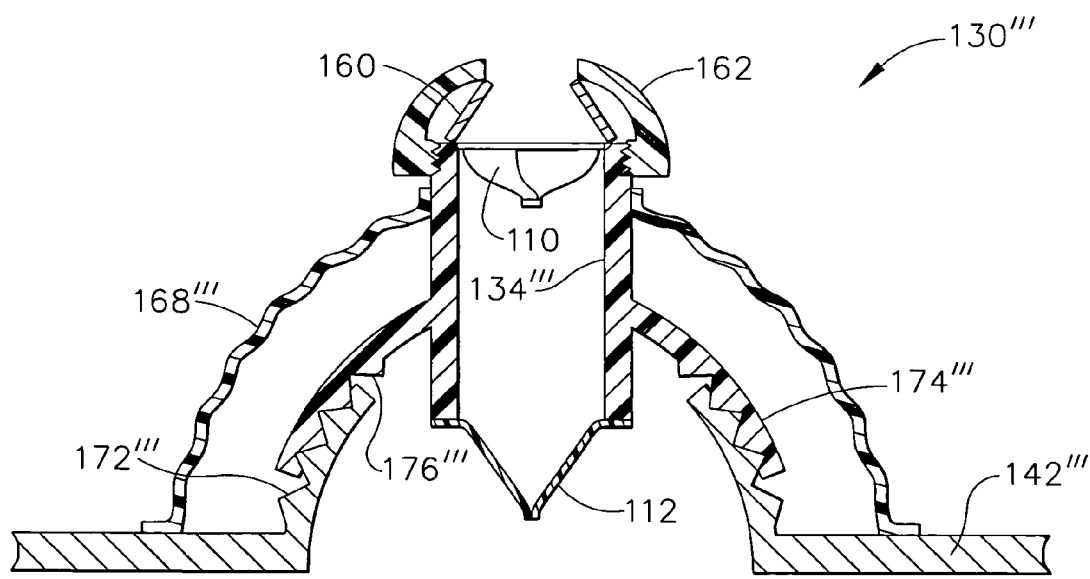
Figures 1, 2:
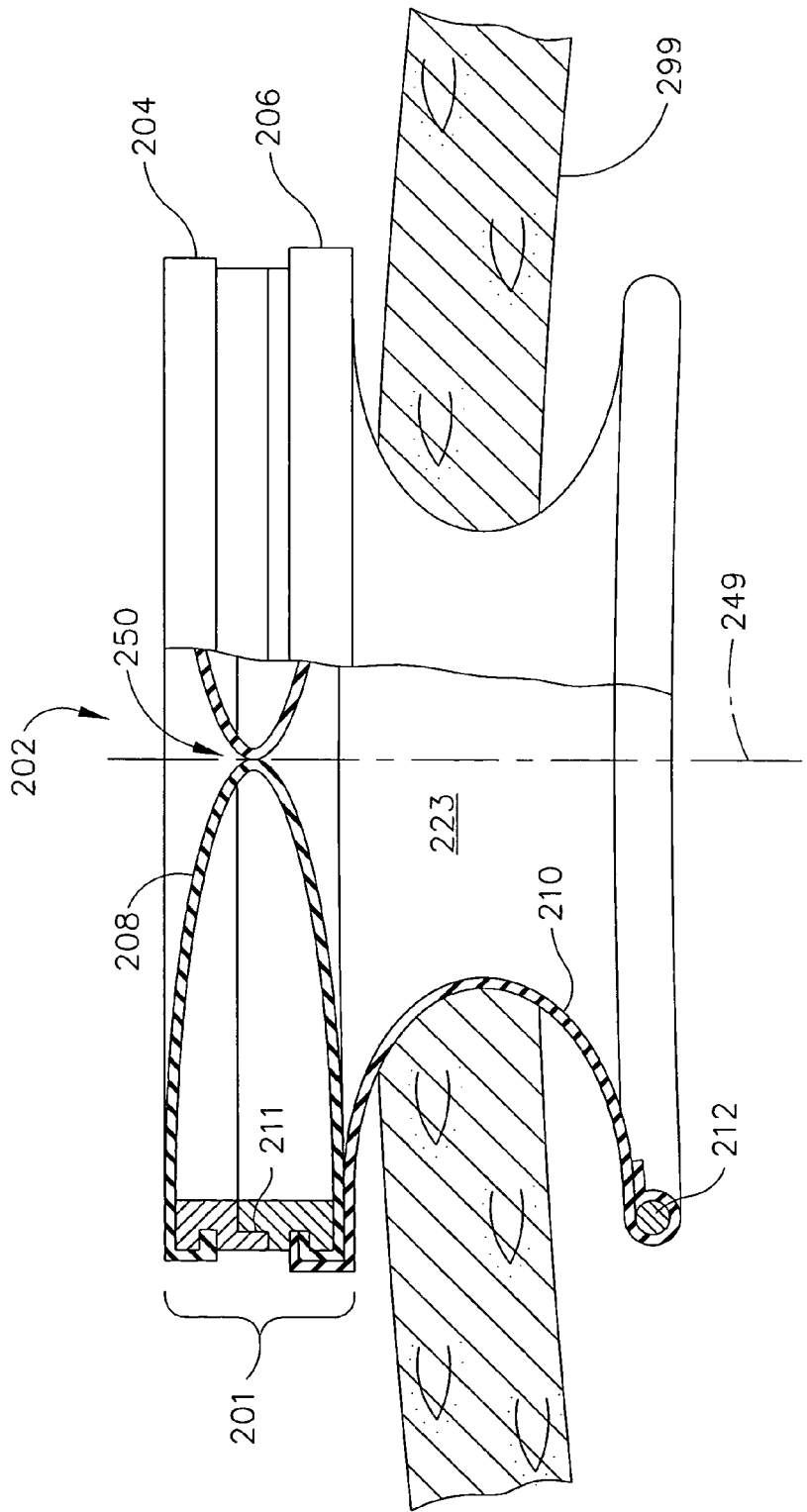
Figure 2:
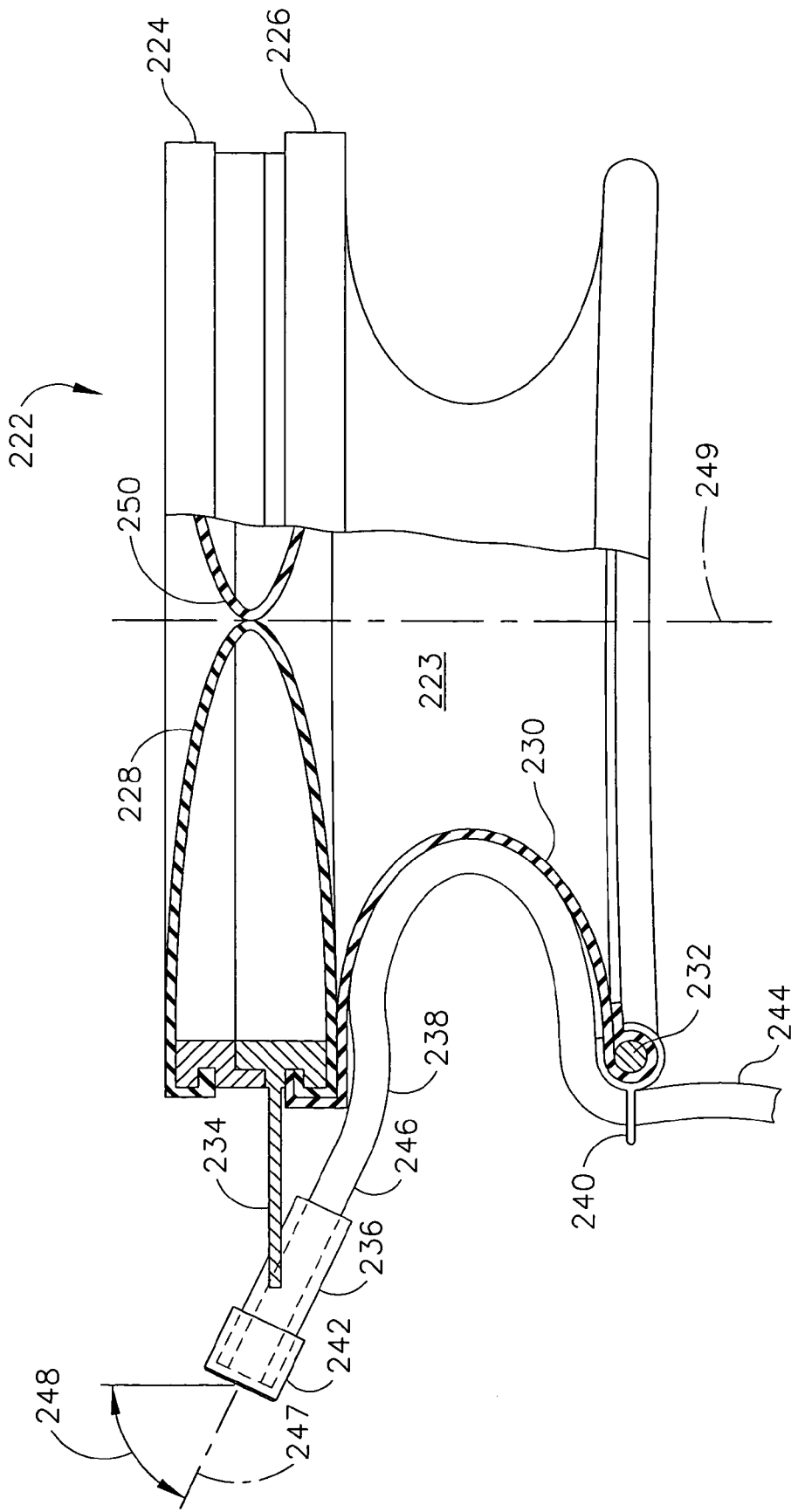
Figures 2, 3:
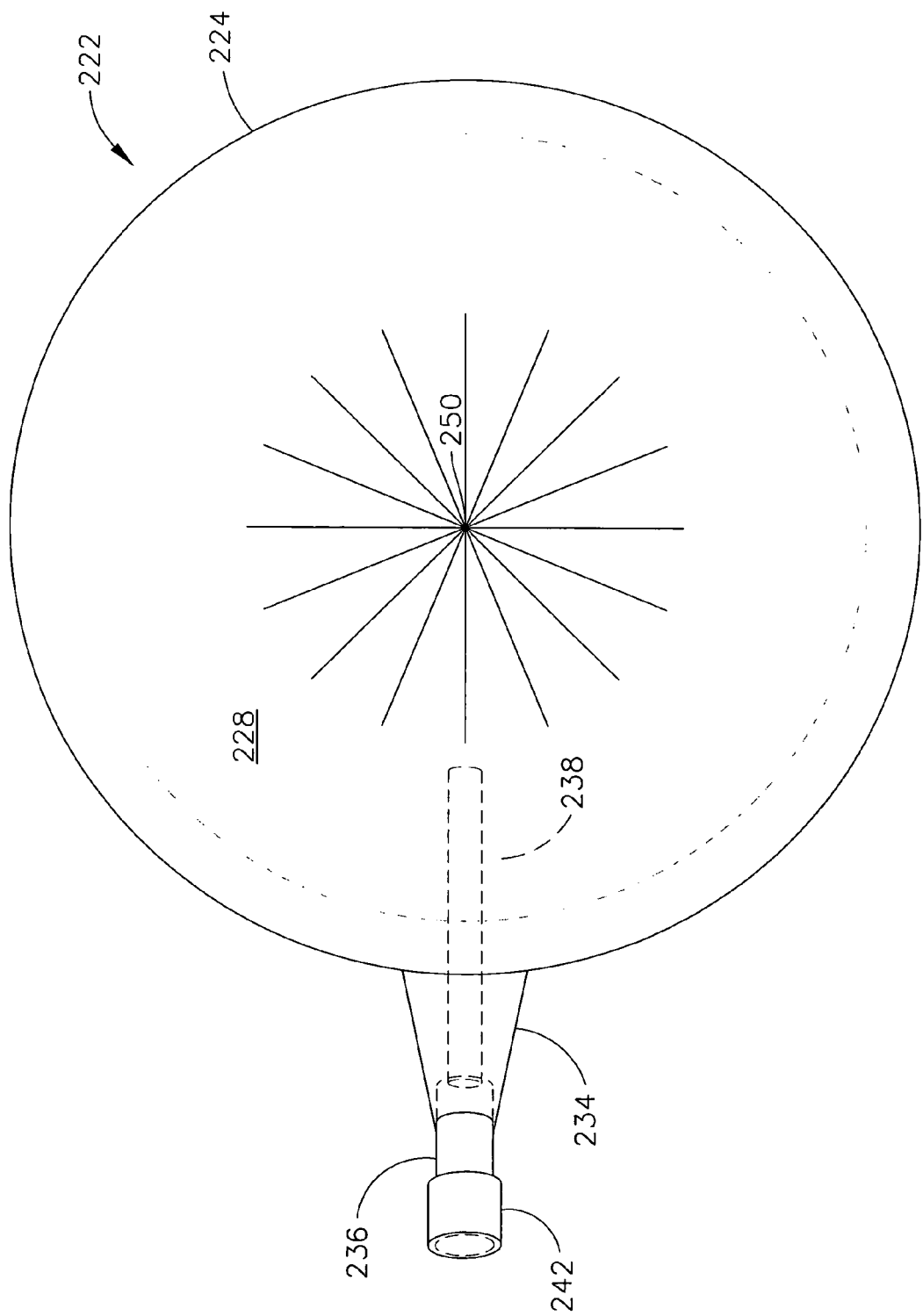
Figures 2, 3, 4:
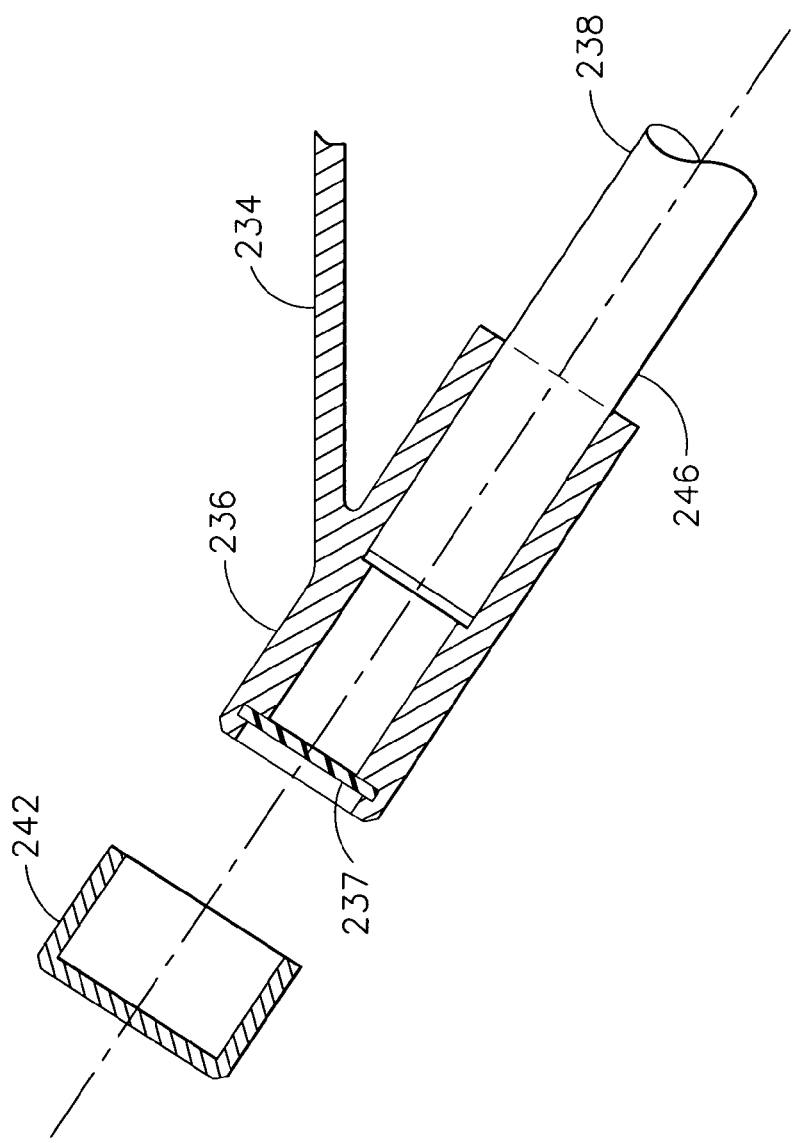
Figures 2, 3, 4, 5:
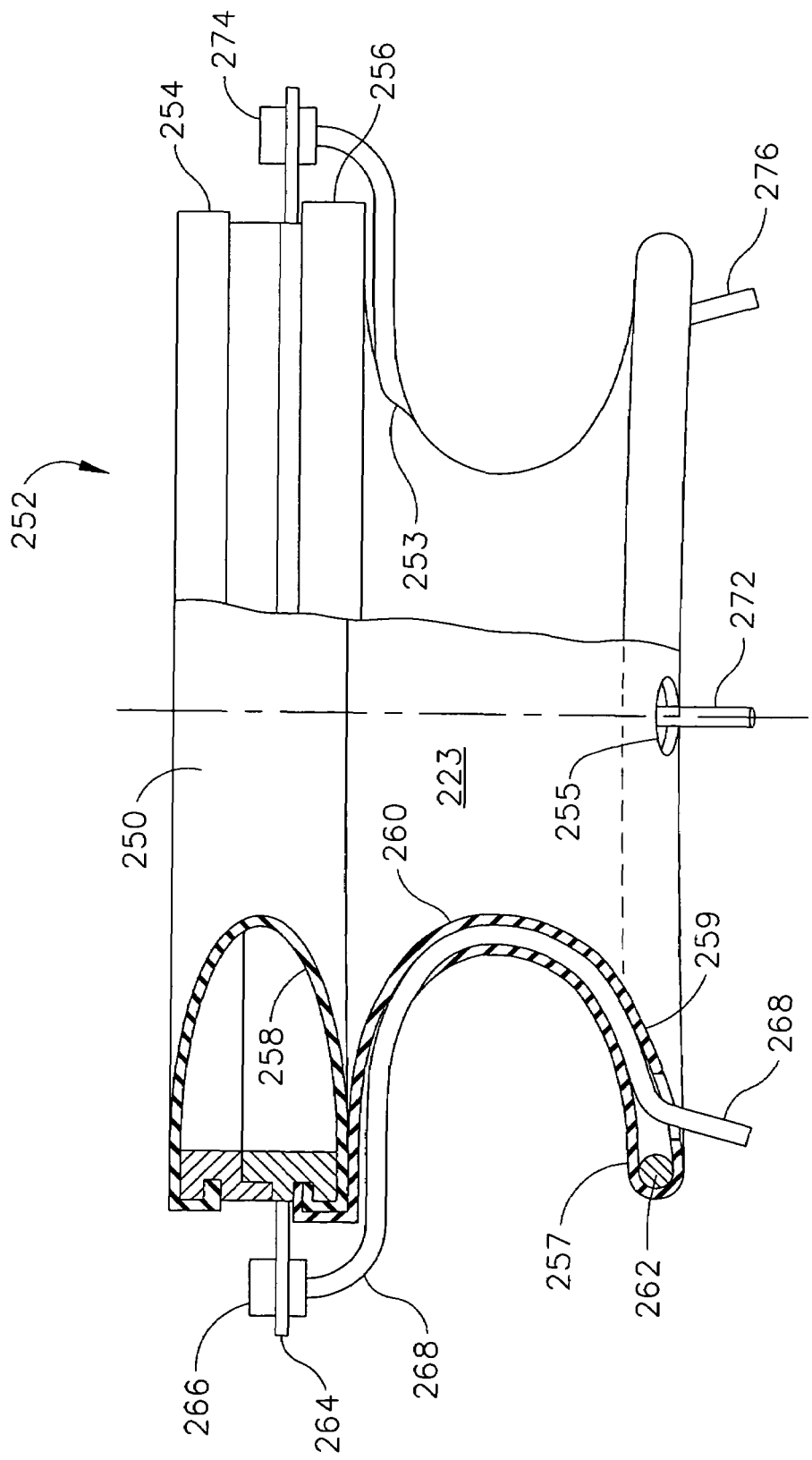
Figures 2, 3, 4, 5, 6:
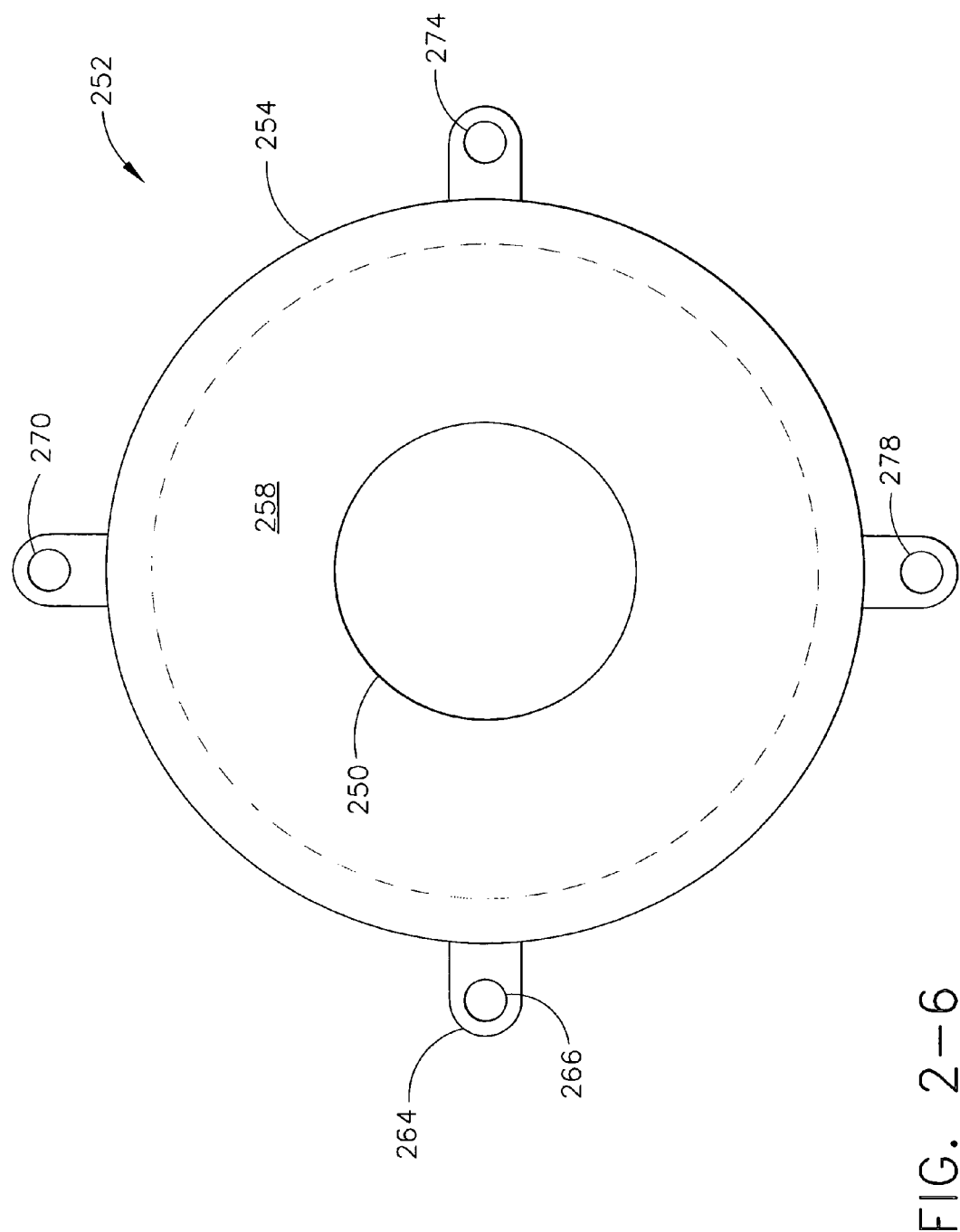
Figures 2, 3, 4, 5, 6, 7:
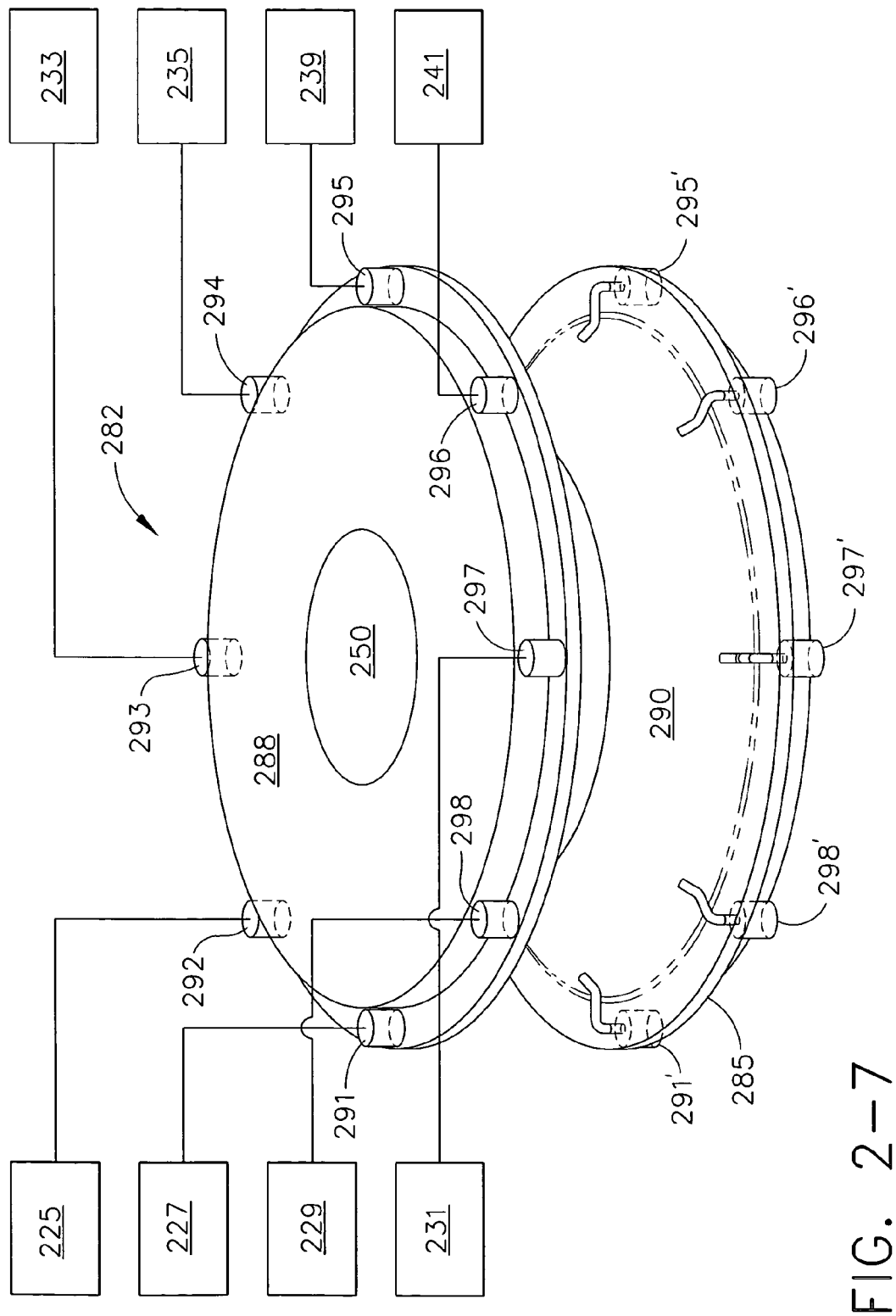
Figures 2, 3, 4, 5, 6, 7, 8, 9:
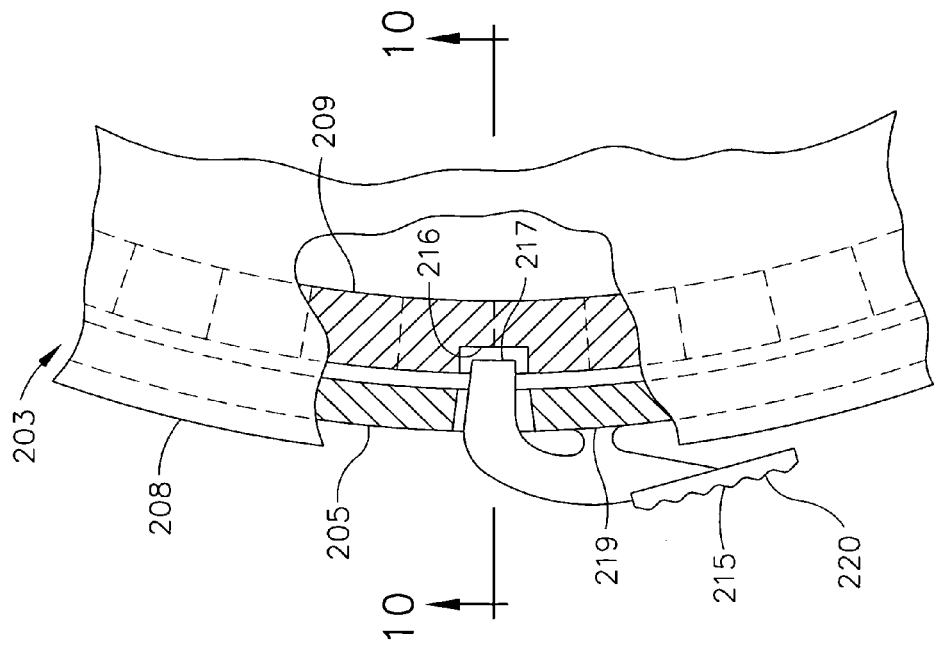
Figures 2, 3, 4, 5, 6, 7, 8:
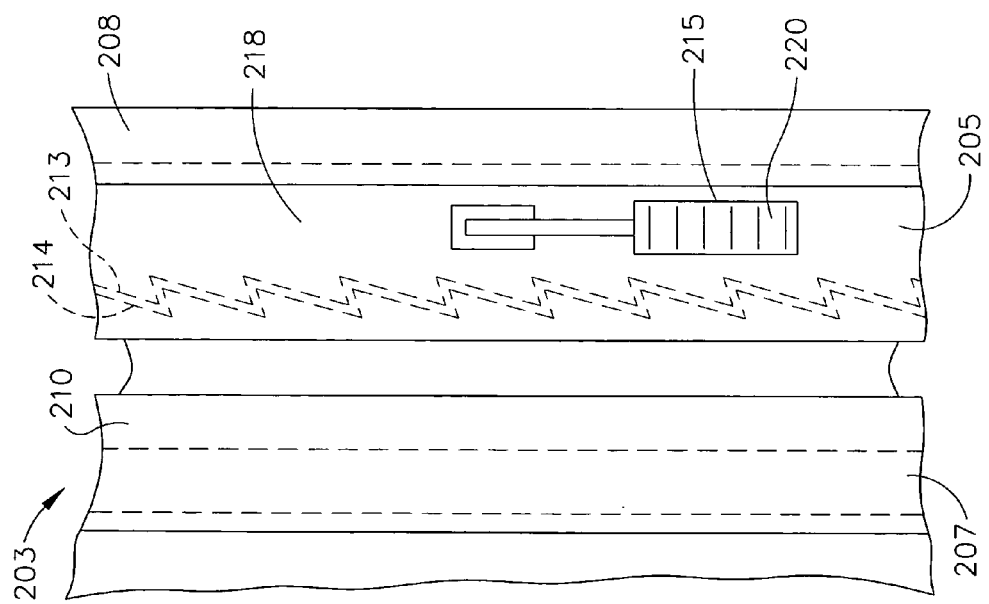
Figures 1, 3:
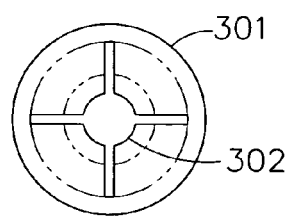
Figures 2, 3:
Figure 3:
Figures 3, 4:
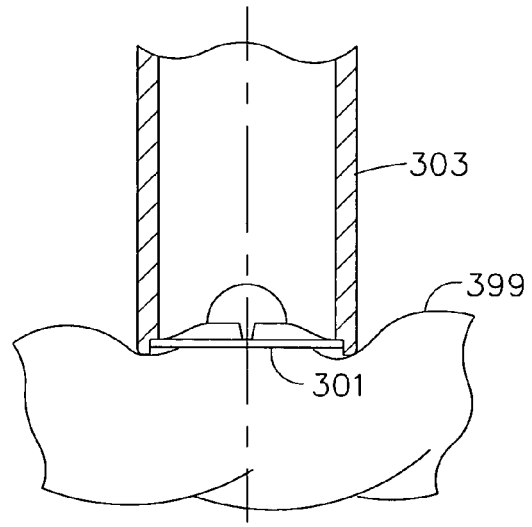
Figures 3, 4, 5, 5A:
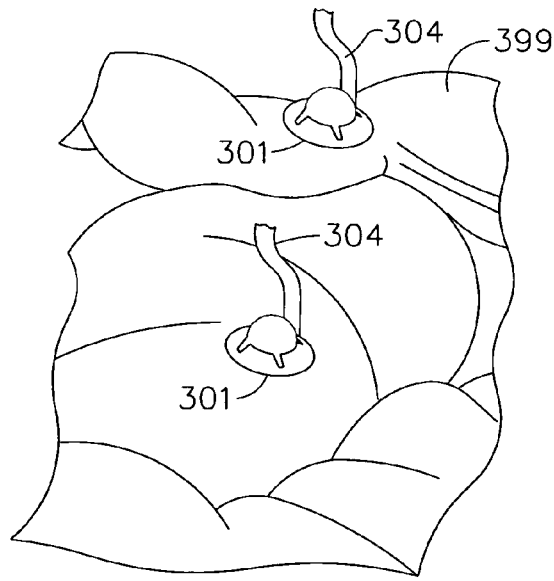
Figures 3, 4, 5, 5B:
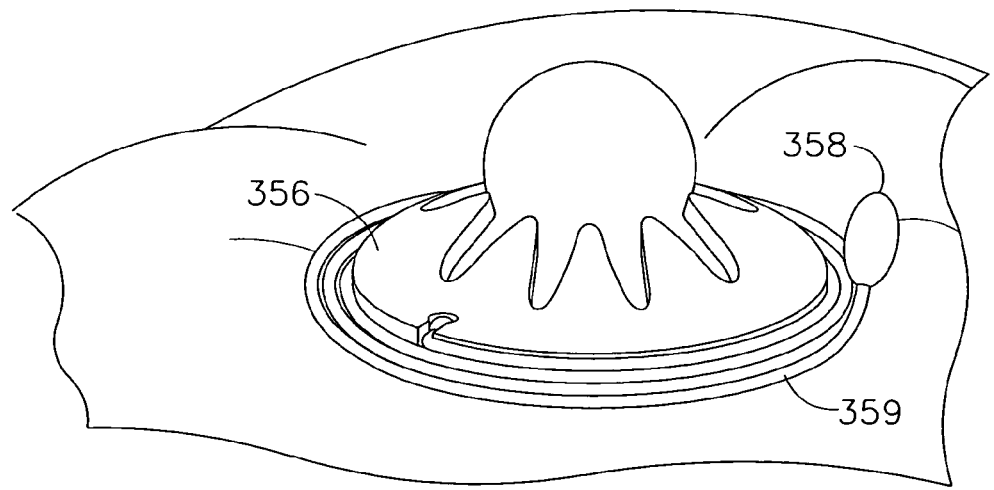
Figures 3, 4, 5, 5C:
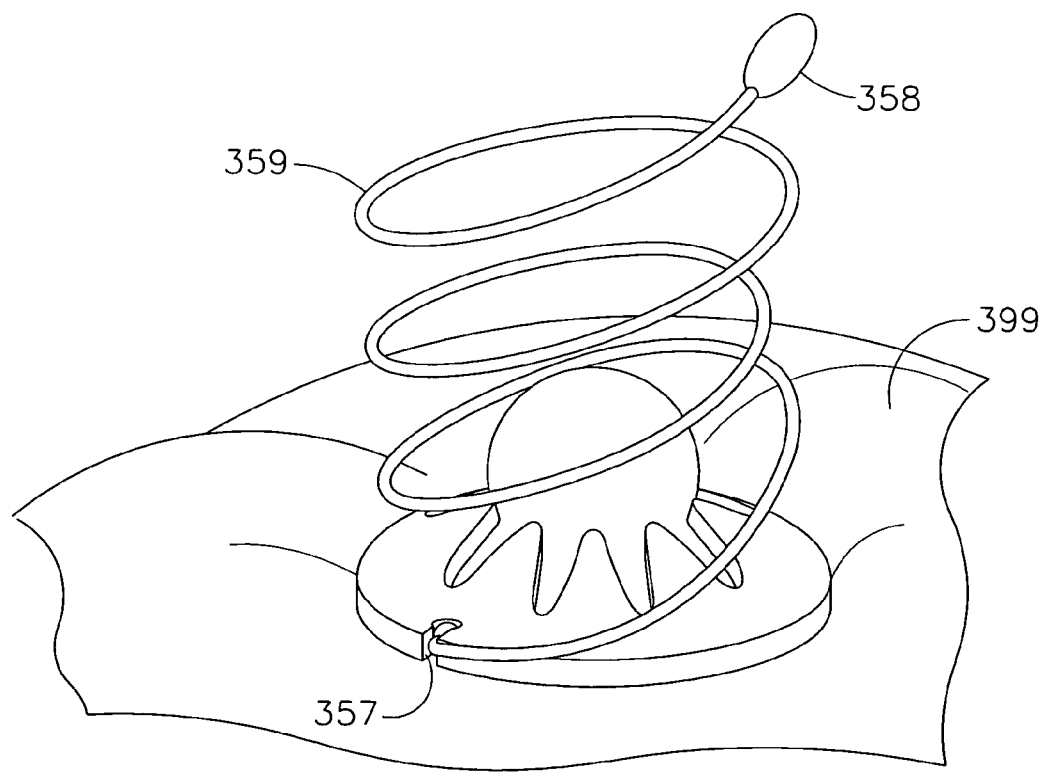
Figures 3, 4, 5, 6:
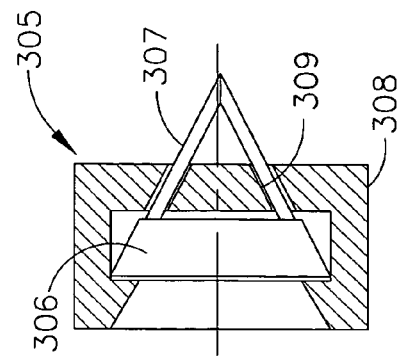
Figures 3, 4, 5, 6, 7:
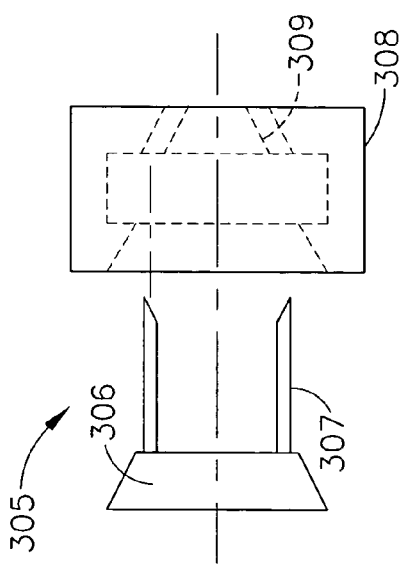
Figures 3, 4, 5, 6, 7, 8:
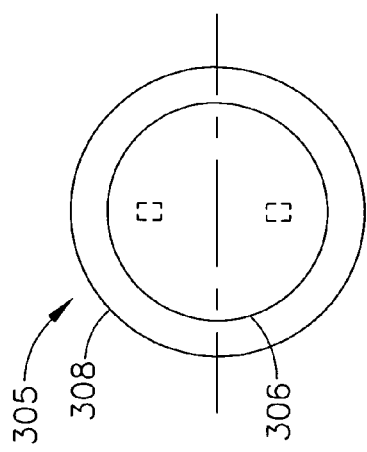
Figures 3, 4, 5, 6, 7, 8, 9:
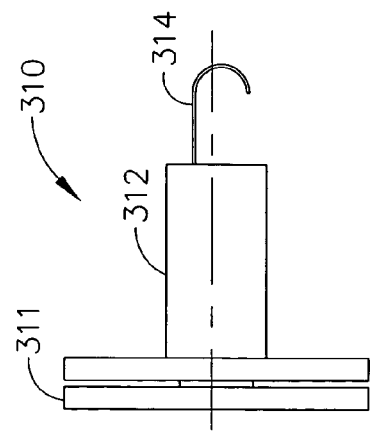
Figures 3, 4, 5, 6, 7, 8, 9, 10:
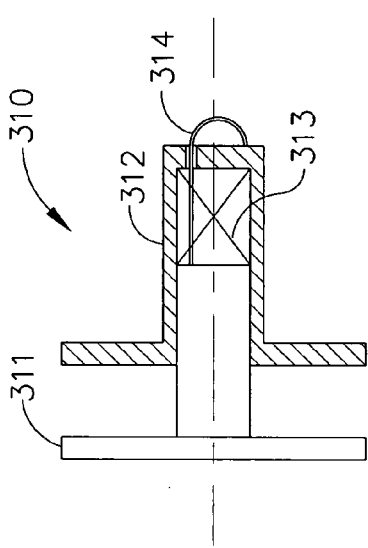
Figures 3, 4, 5, 6, 7, 8, 9, 10, 11:
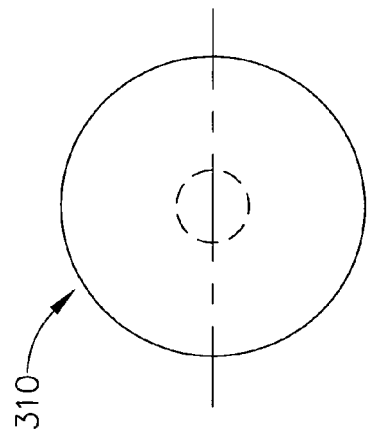
Figures 3, 4, 5, 6, 7, 8, 9, 10, 11, 12, 13, 14, 15, 16, 17, 18, 19, 20, 21, 22, 23, 24, 25, 26, 27, 28, 29, 30:
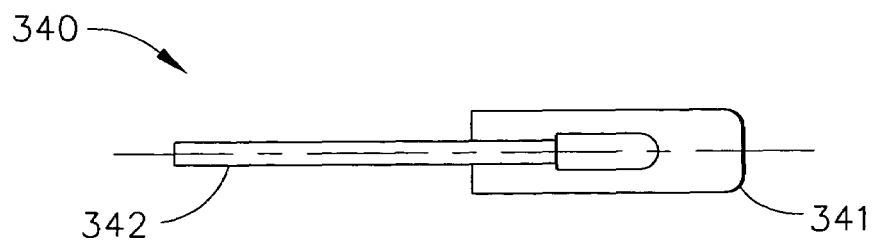
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31:
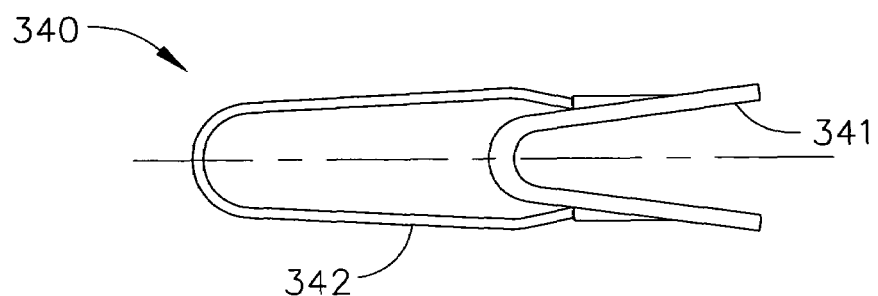
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32:
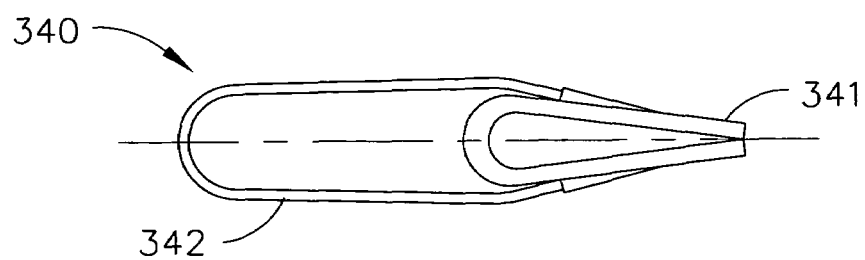
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33:
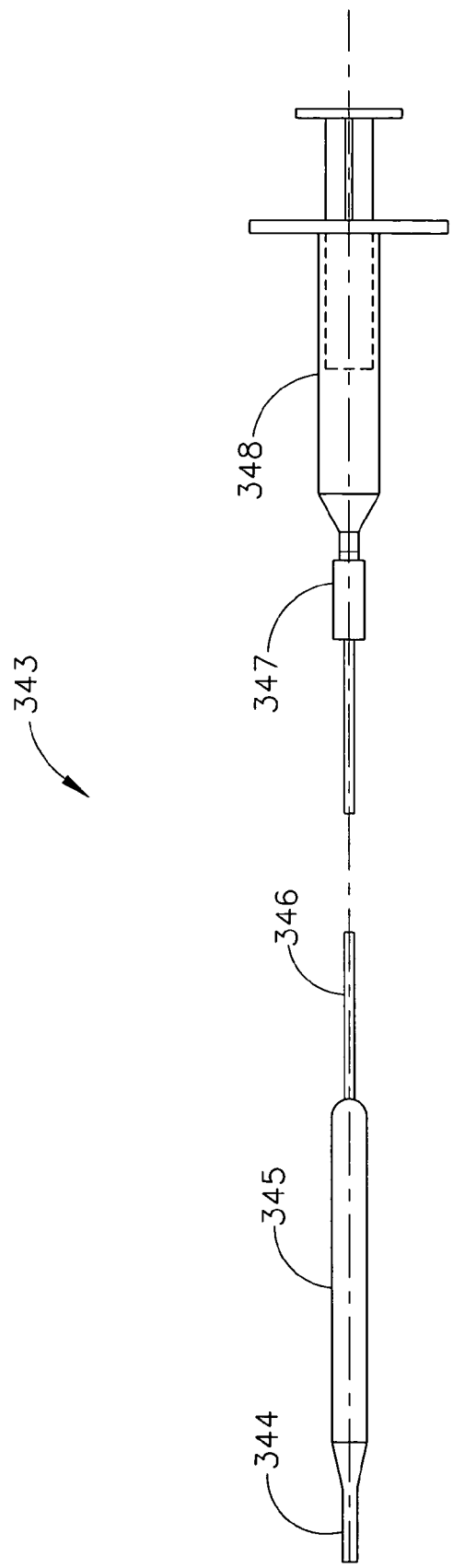
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34:
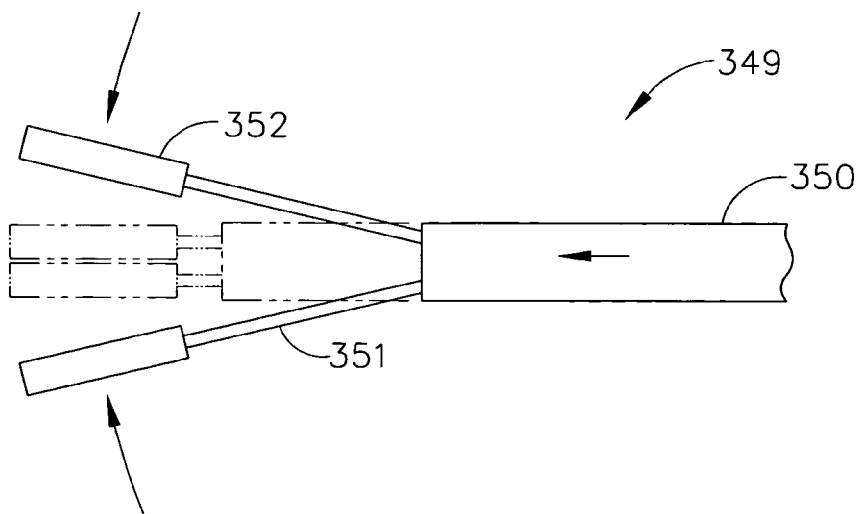
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35:
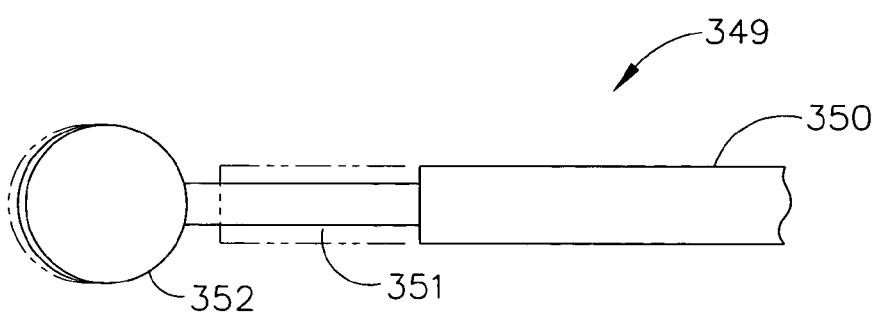
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36:
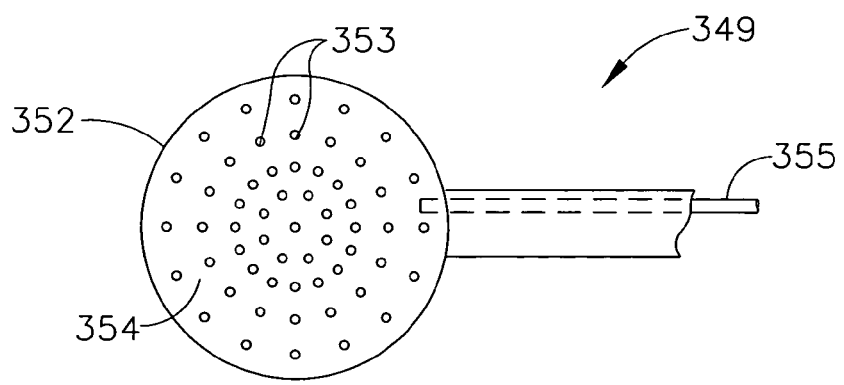
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37:
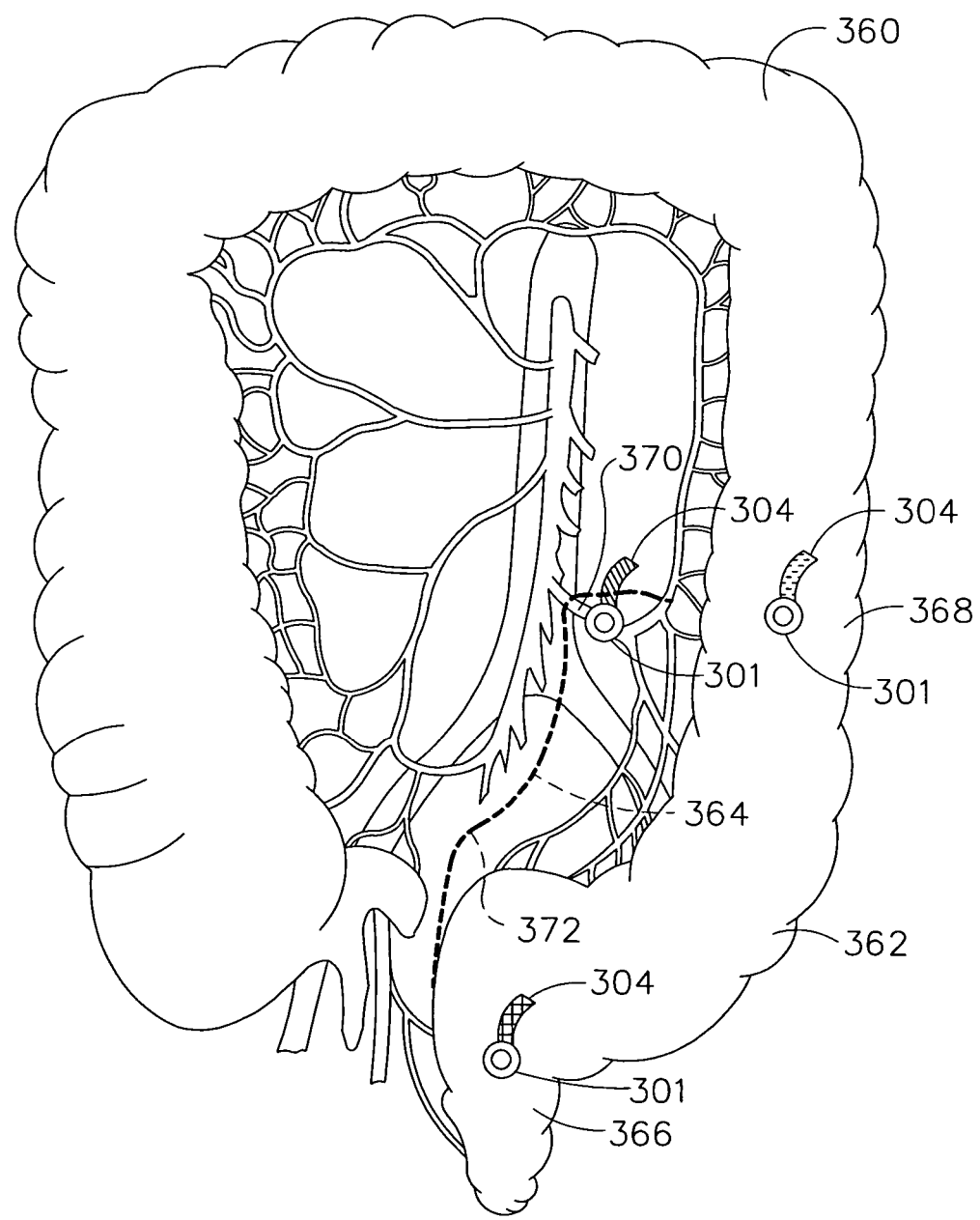
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38:
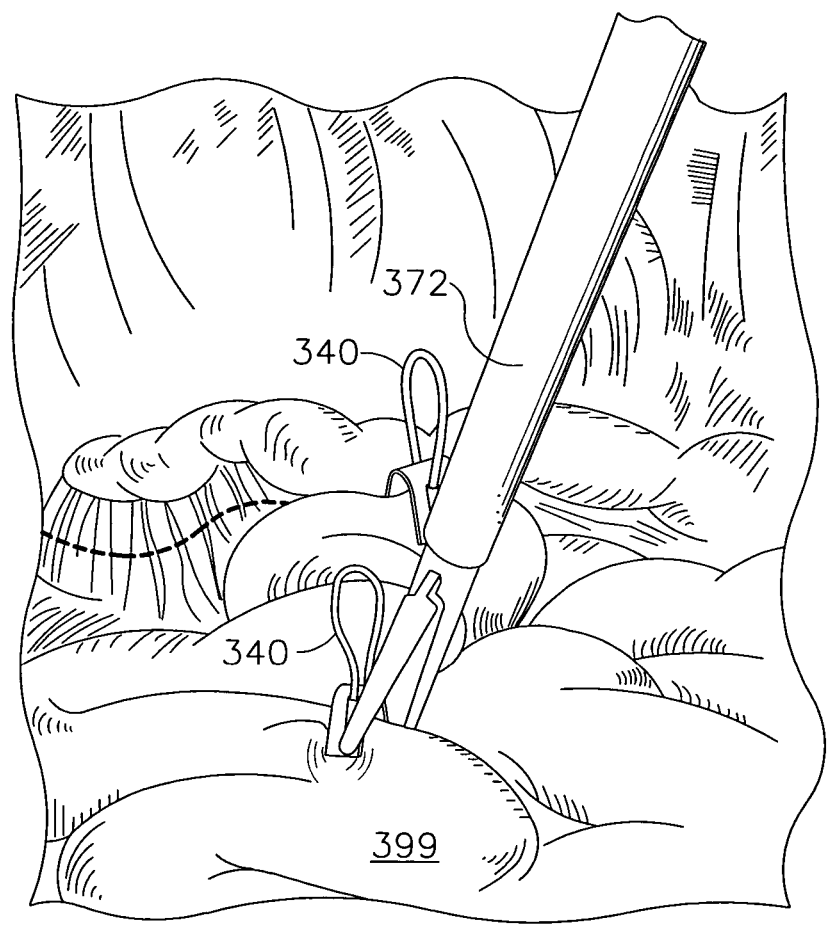
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39:
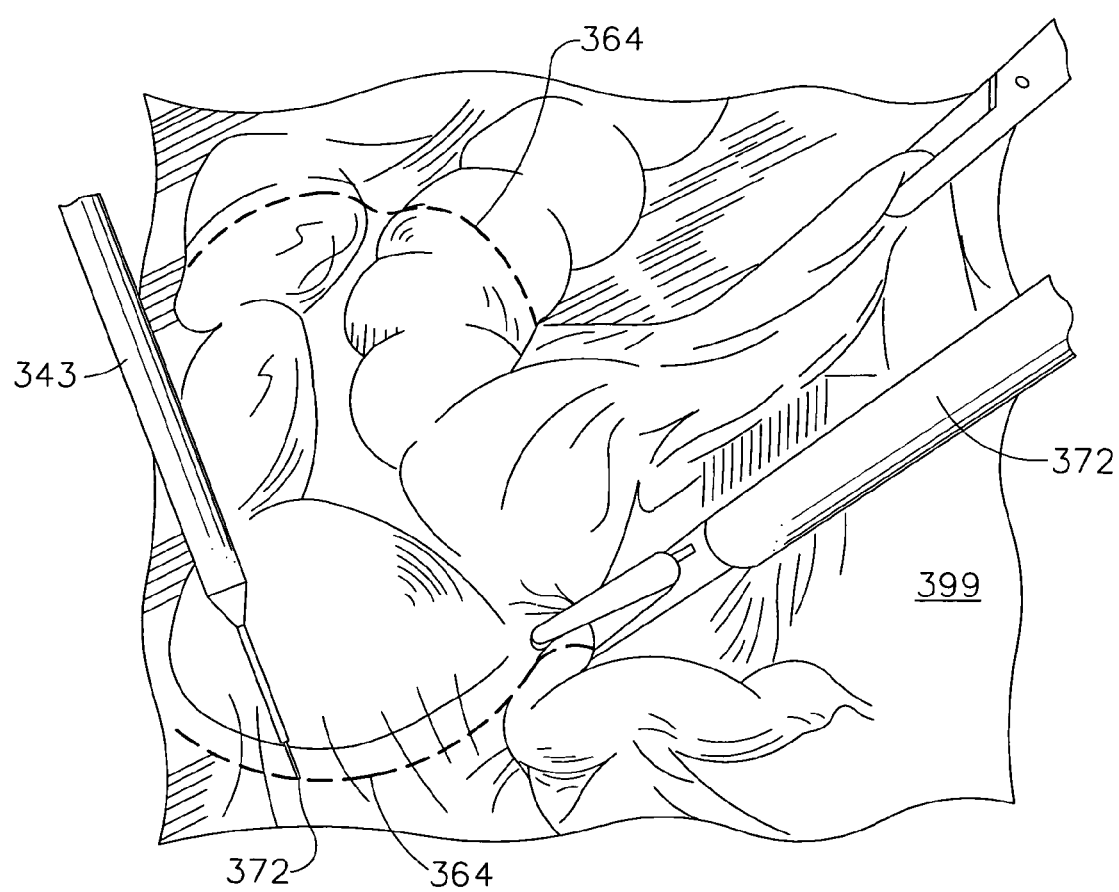
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40:
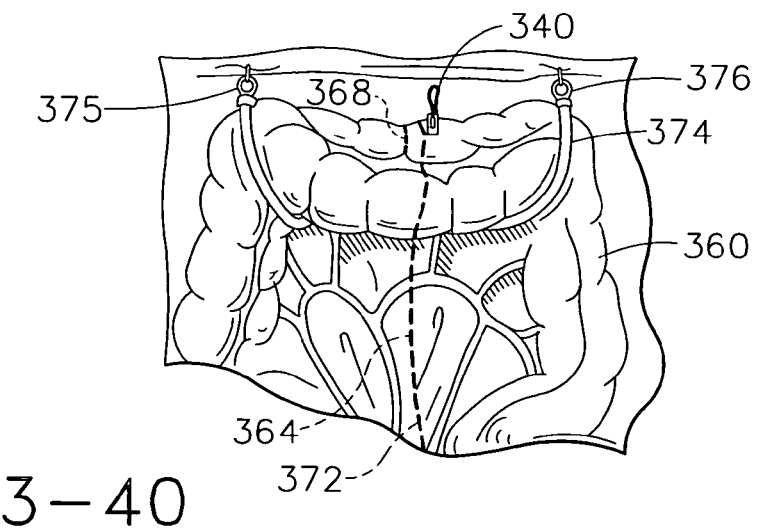
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
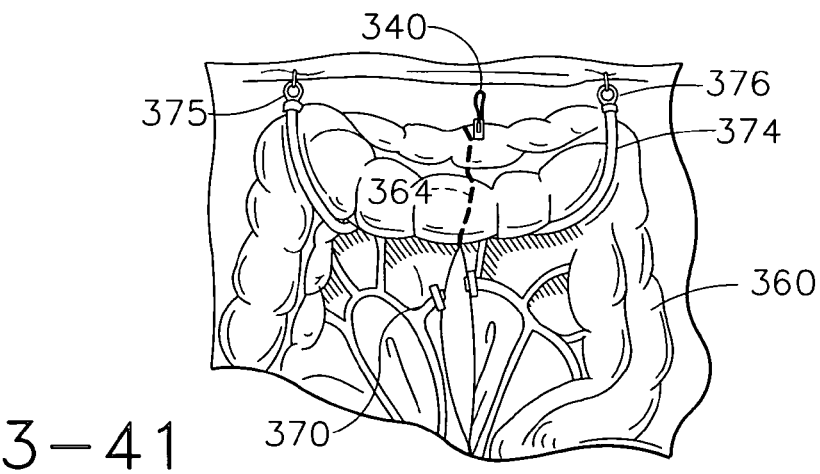
Figures 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42:
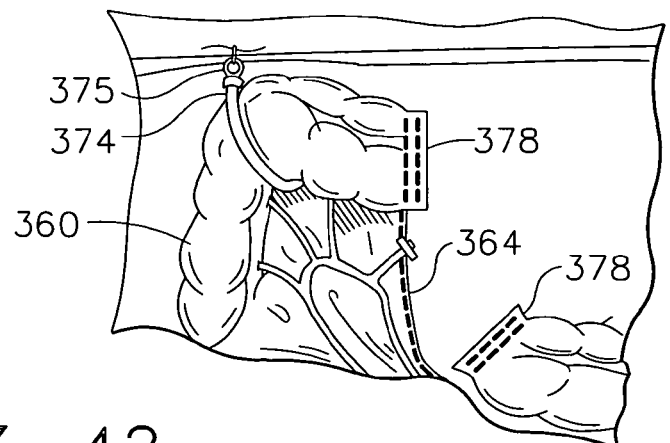
Figures 1, 4:
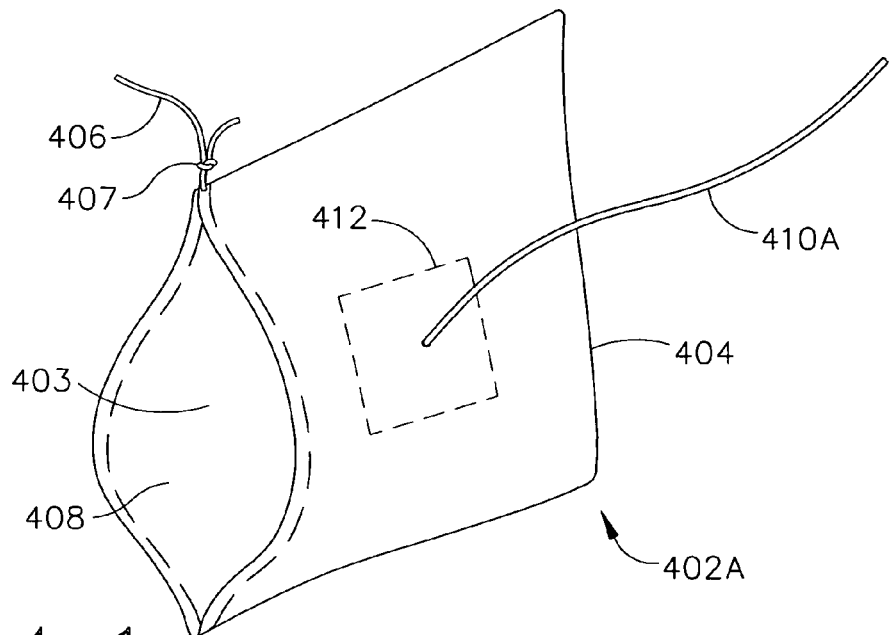
Figures 2, 4:
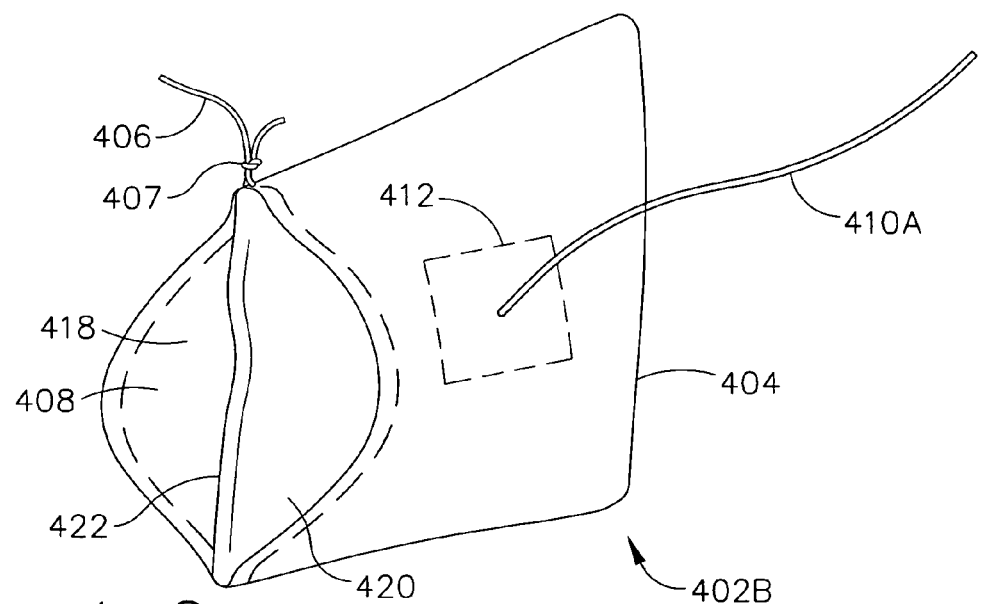
Figures 3, 4:
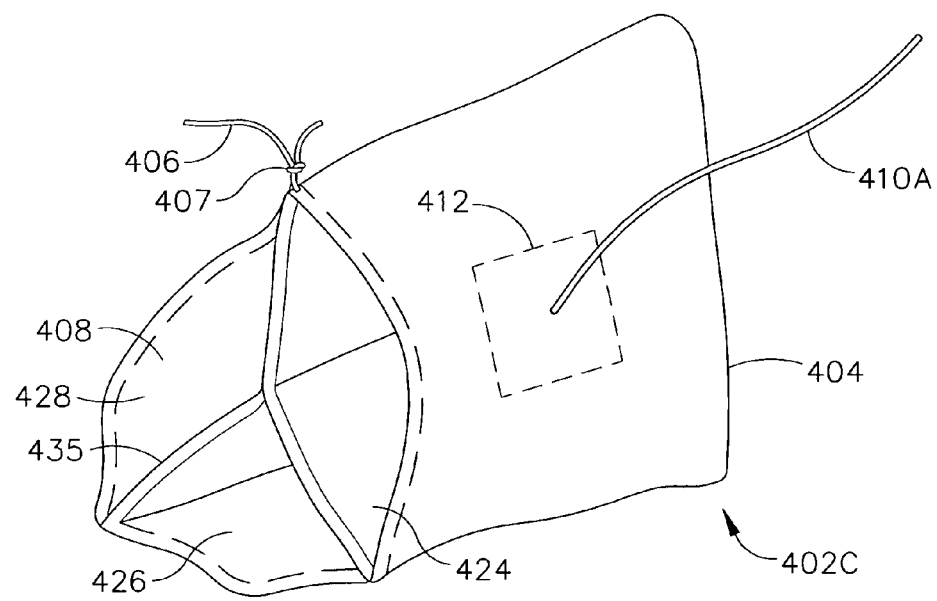
Figure 4:
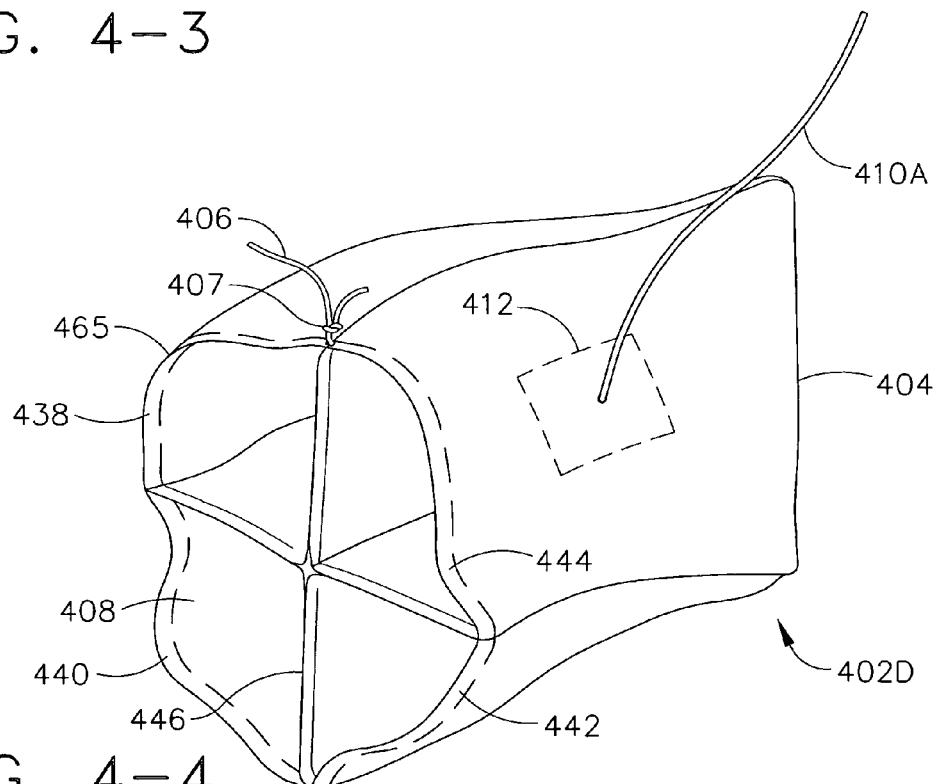
Figures 4, 5:
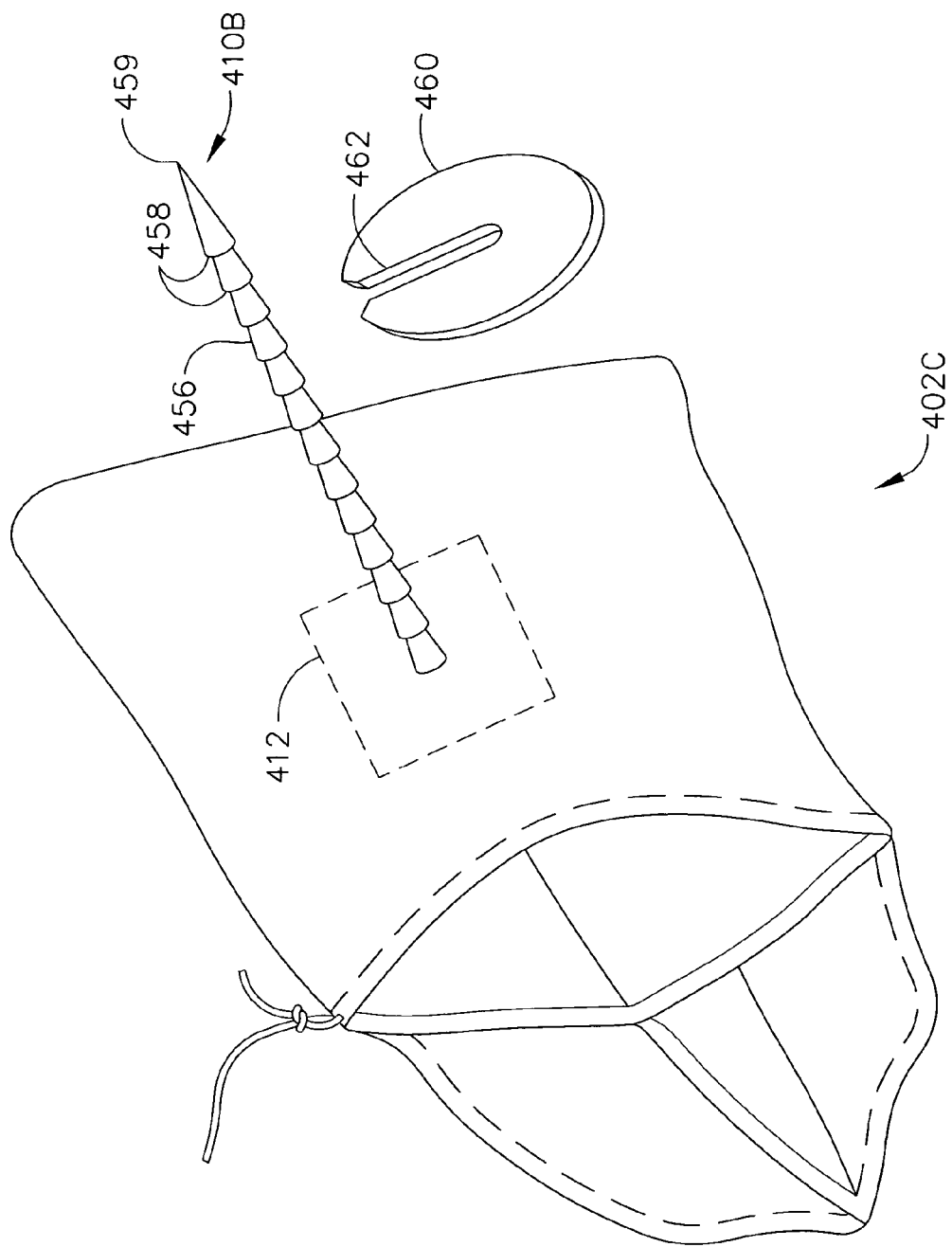
Figures 4, 5, 6:
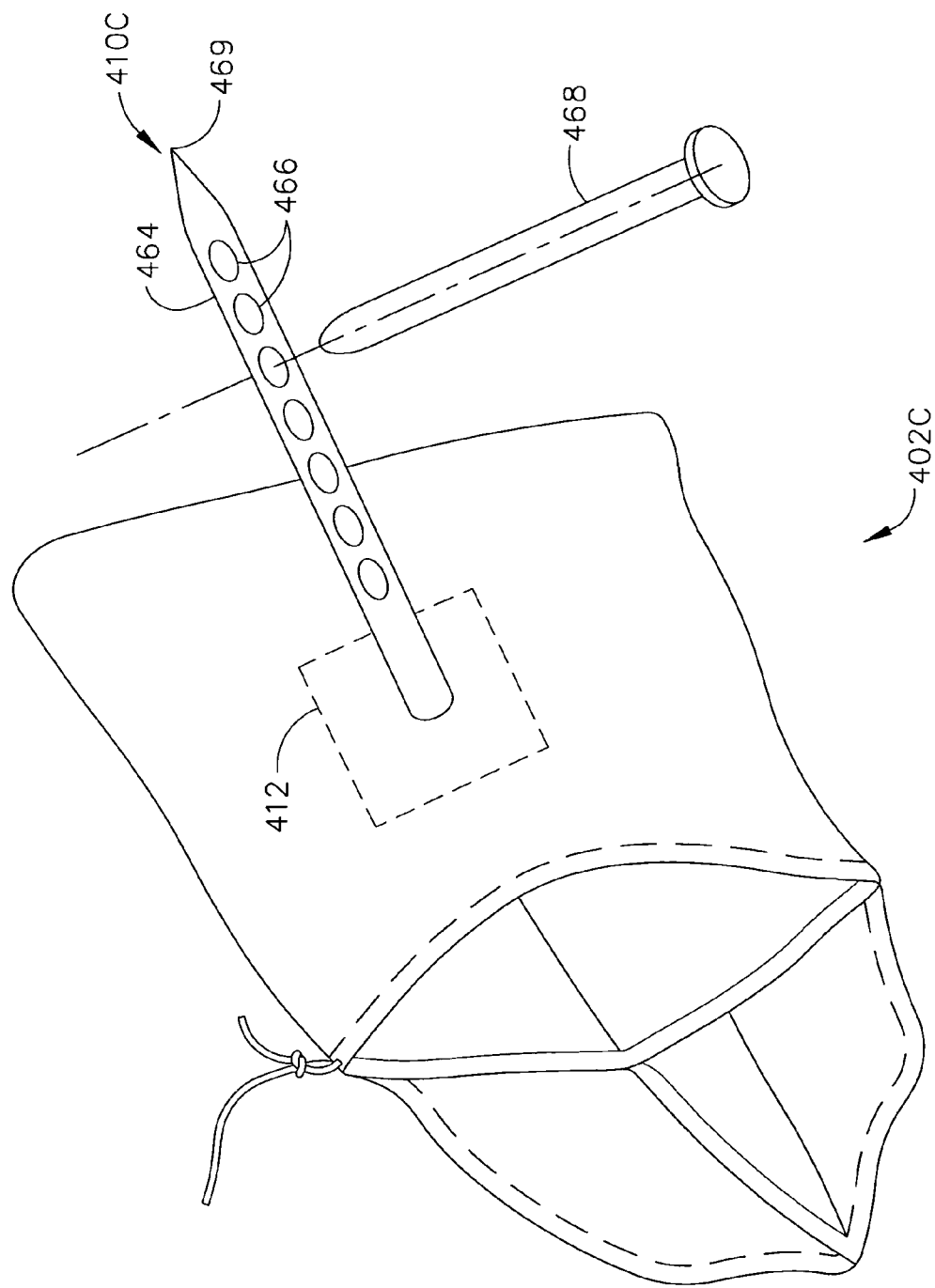
Figures 4, 5, 6, 7:
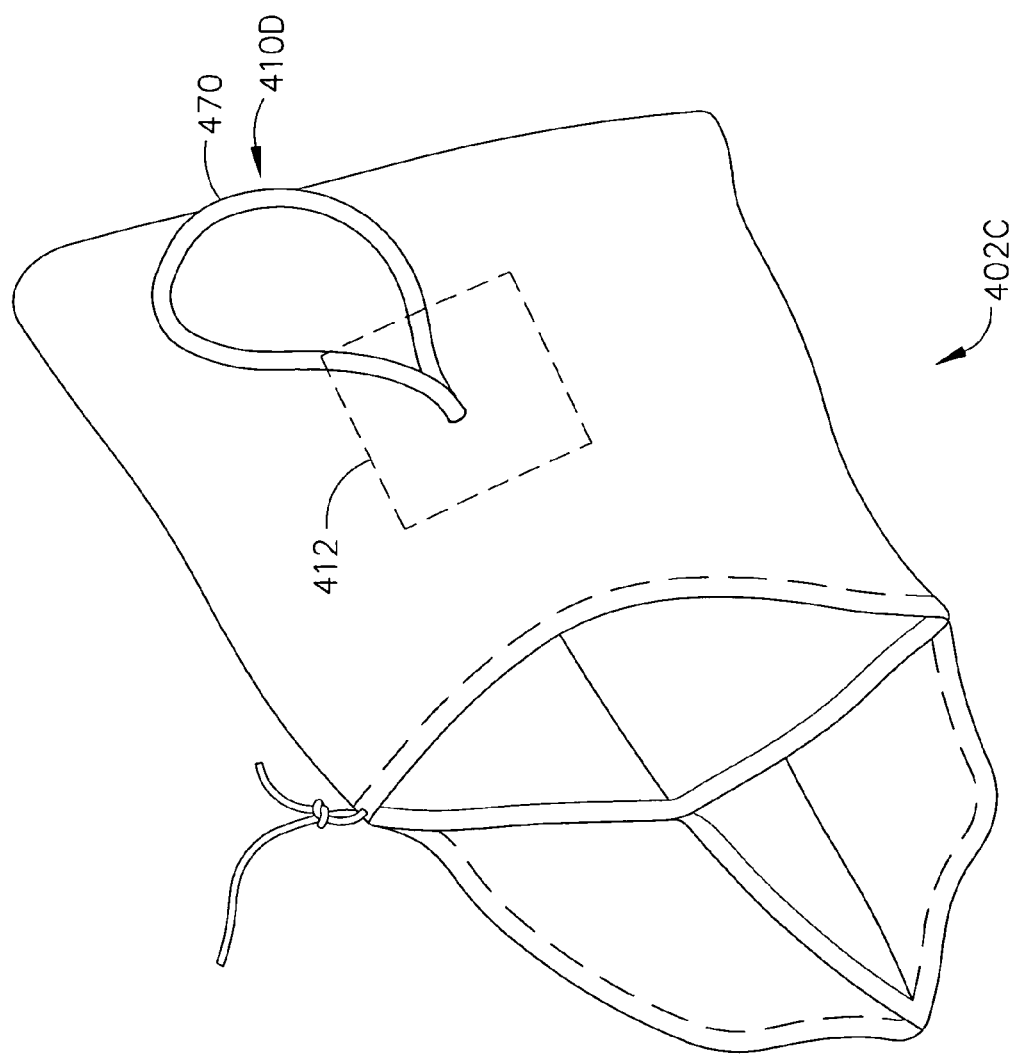
Figures 4, 5, 6, 7, 8:
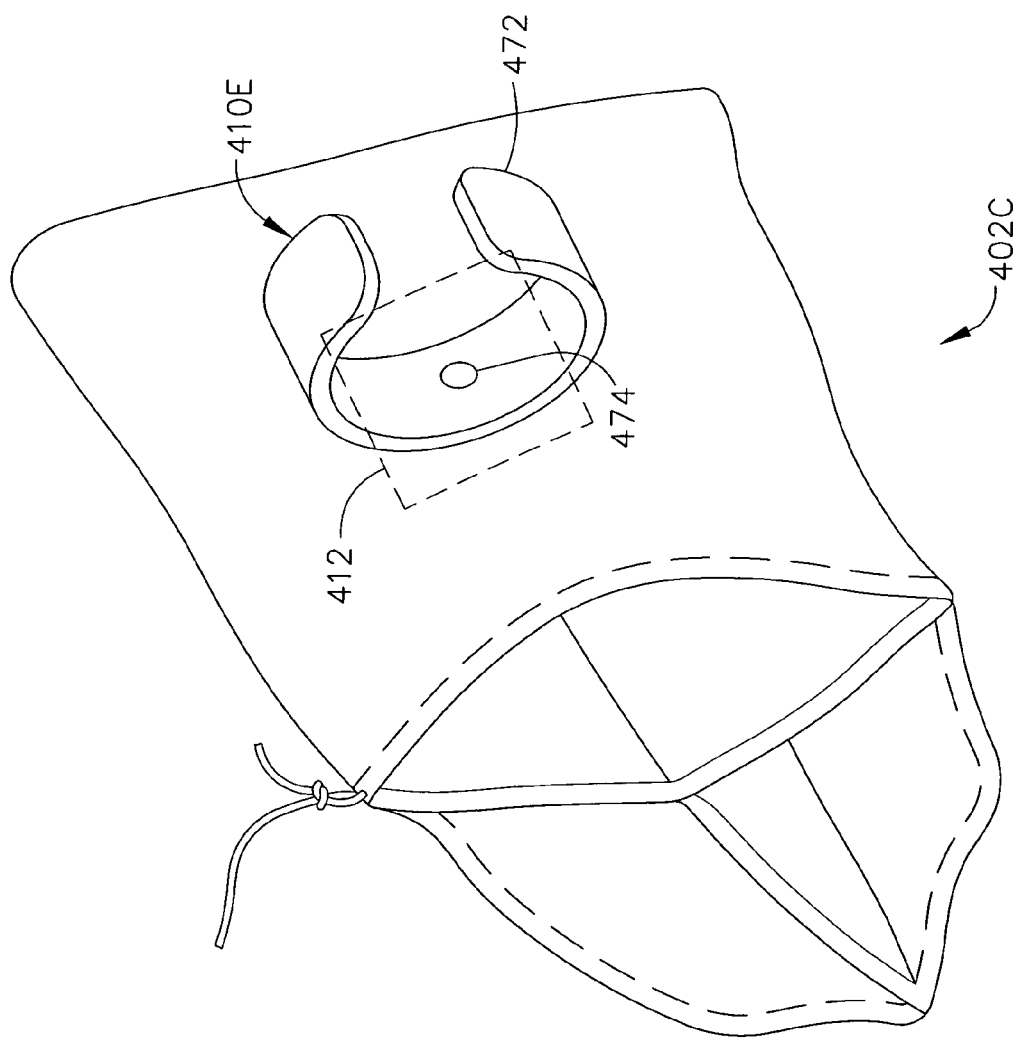
Figures 4, 5, 6, 7, 8, 9:
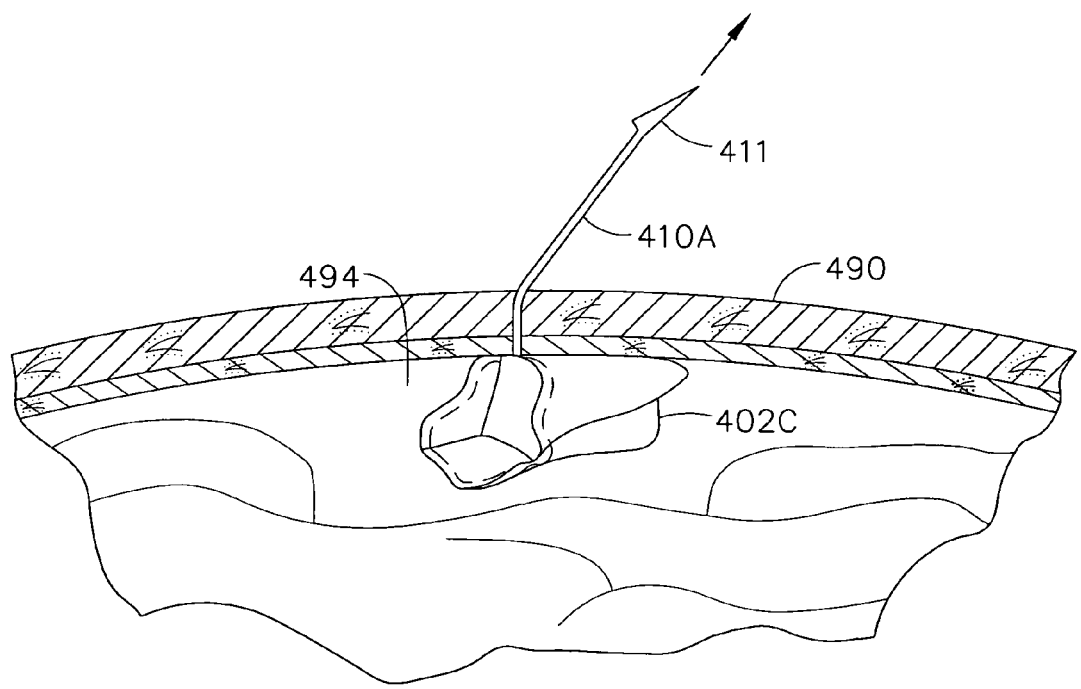
Figures 4, 5, 6, 7, 8, 9, 10:
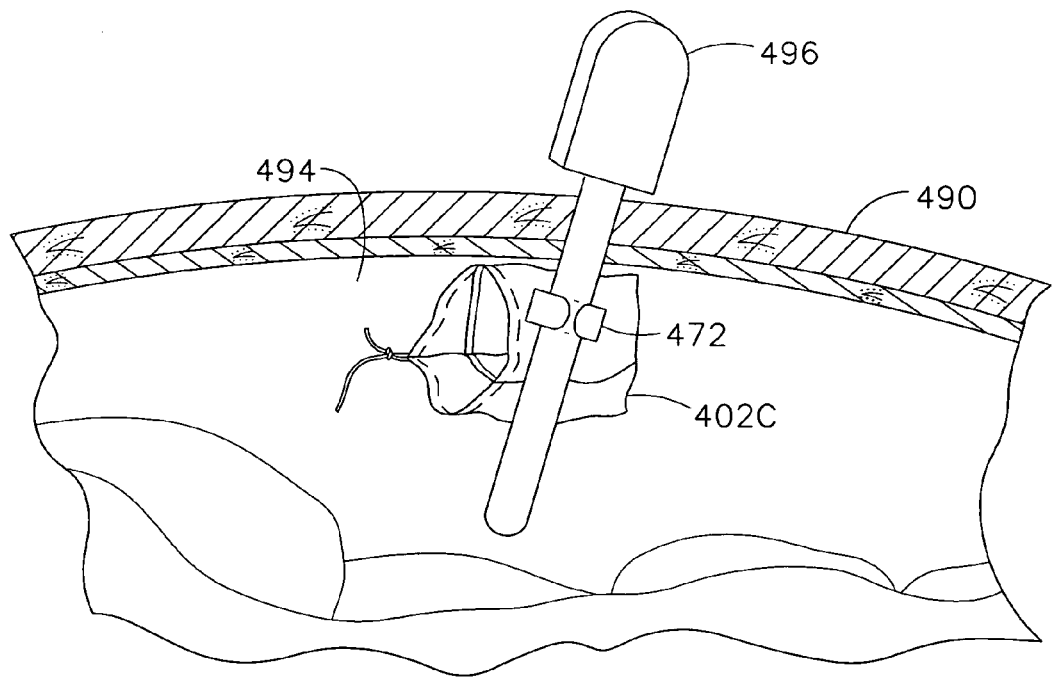
Figures 4, 5, 6, 7, 8, 9, 10, 11:
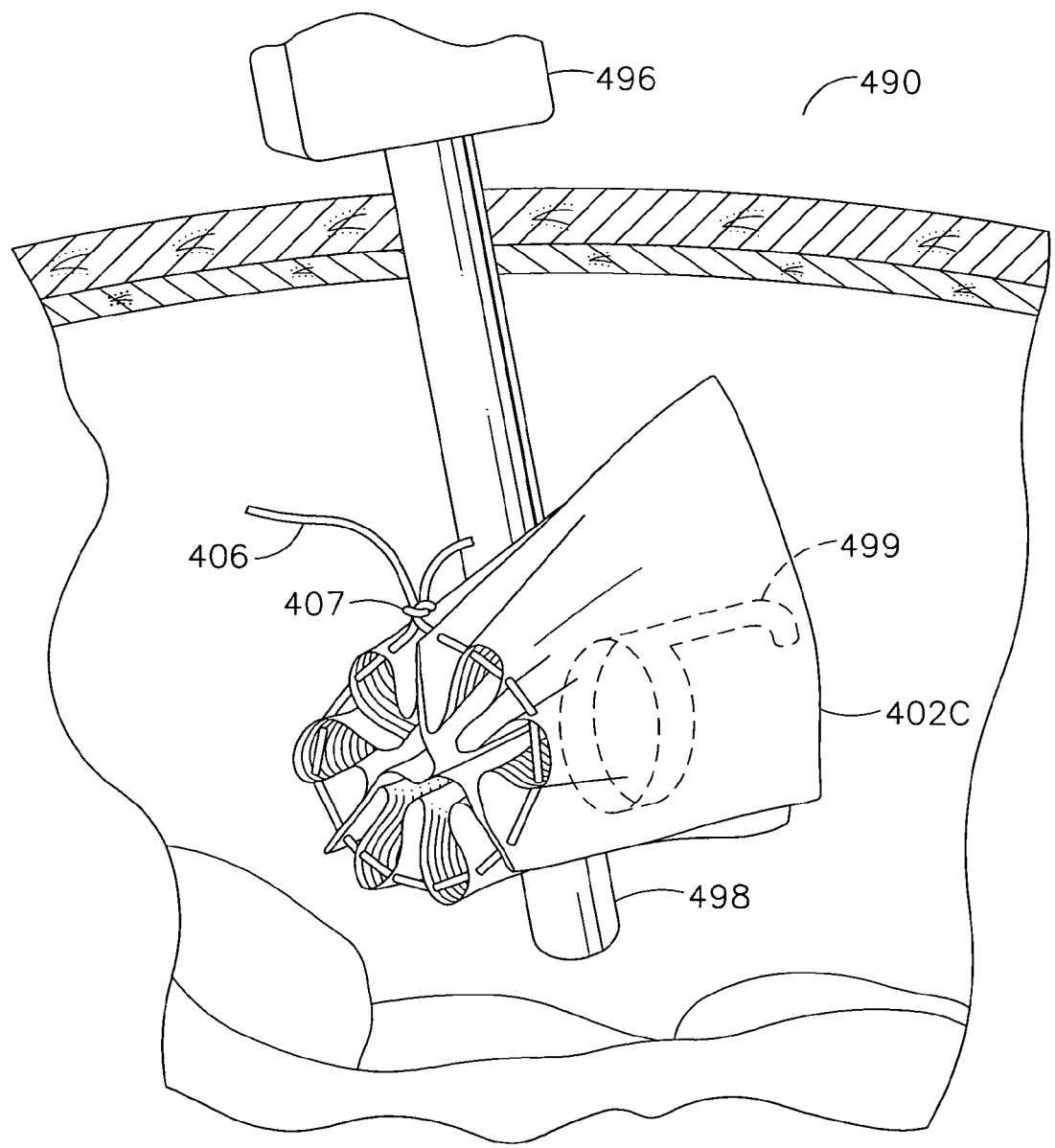
Figures 4, 5, 6, 7, 8, 9, 10, 11, 12:
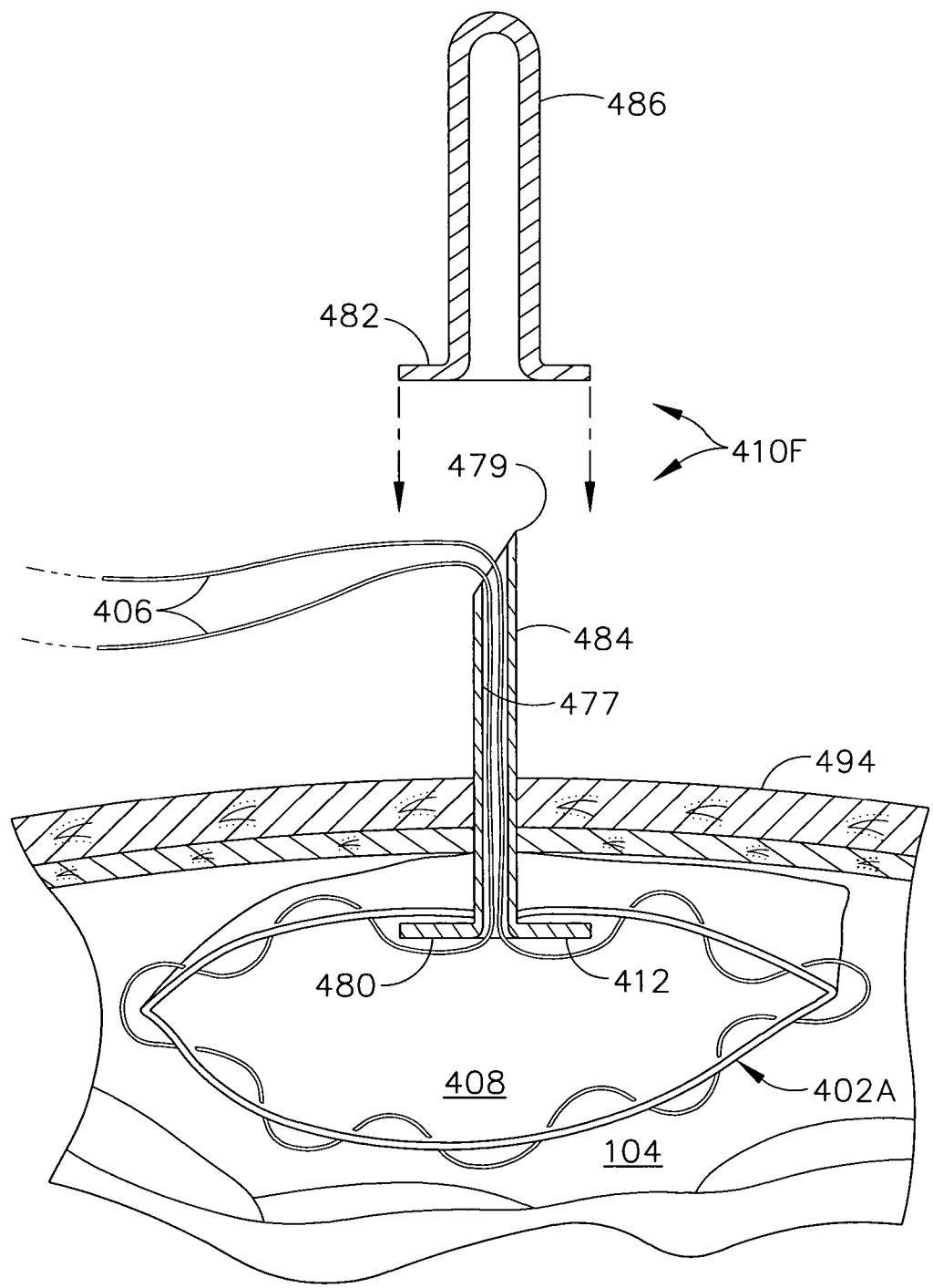
Figures 4, 5, 6, 7, 8, 9, 10, 11, 12, 13:
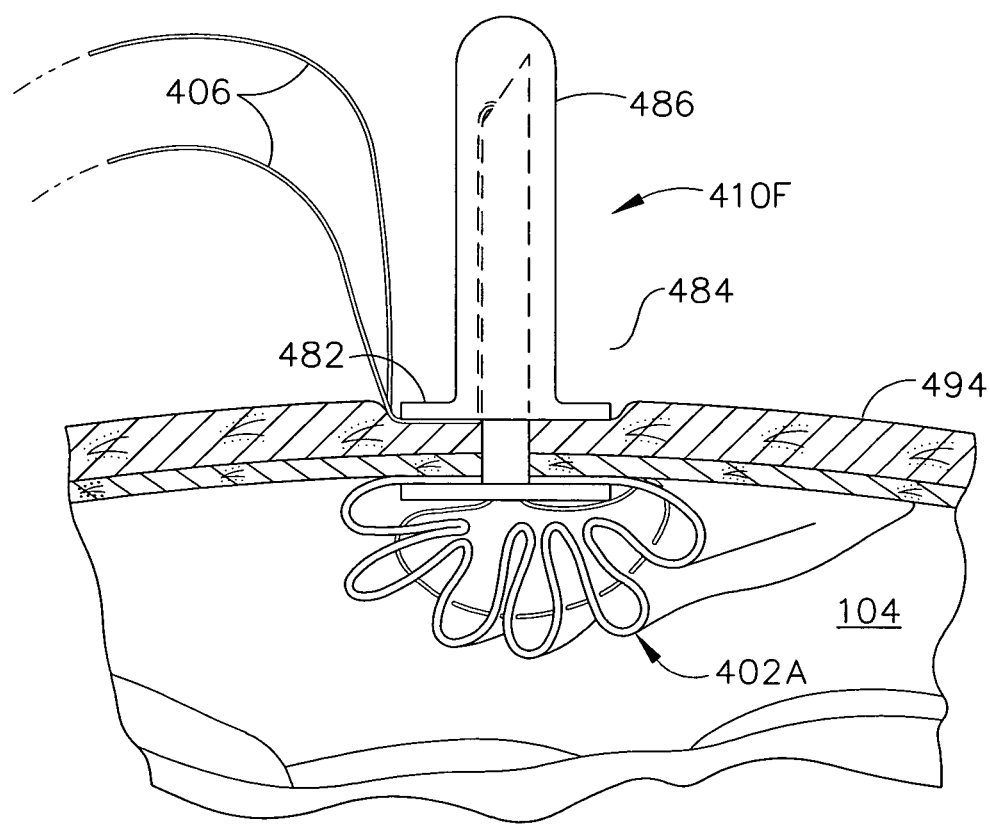
Figures 1, 5:
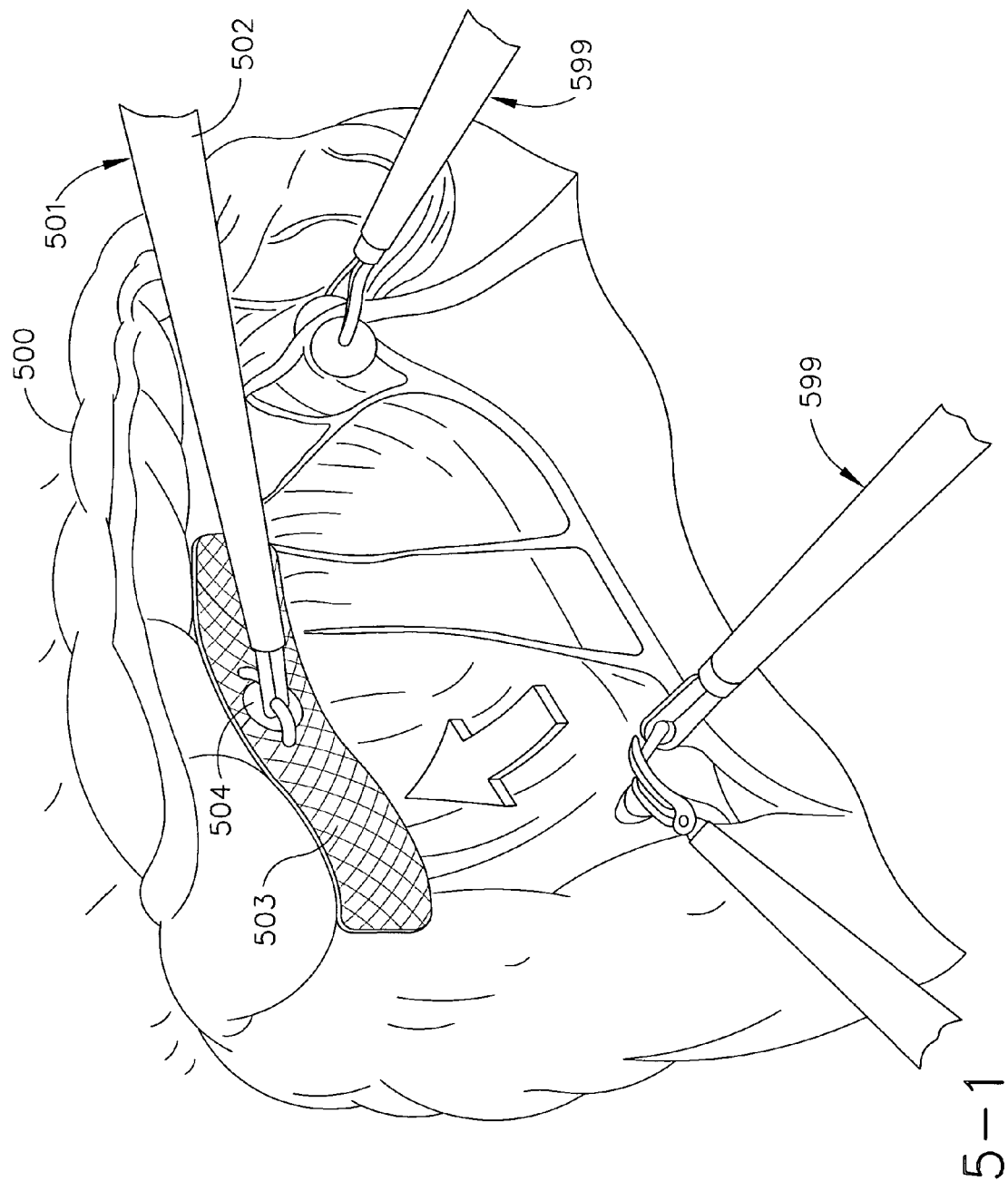
Figures 2, 5:
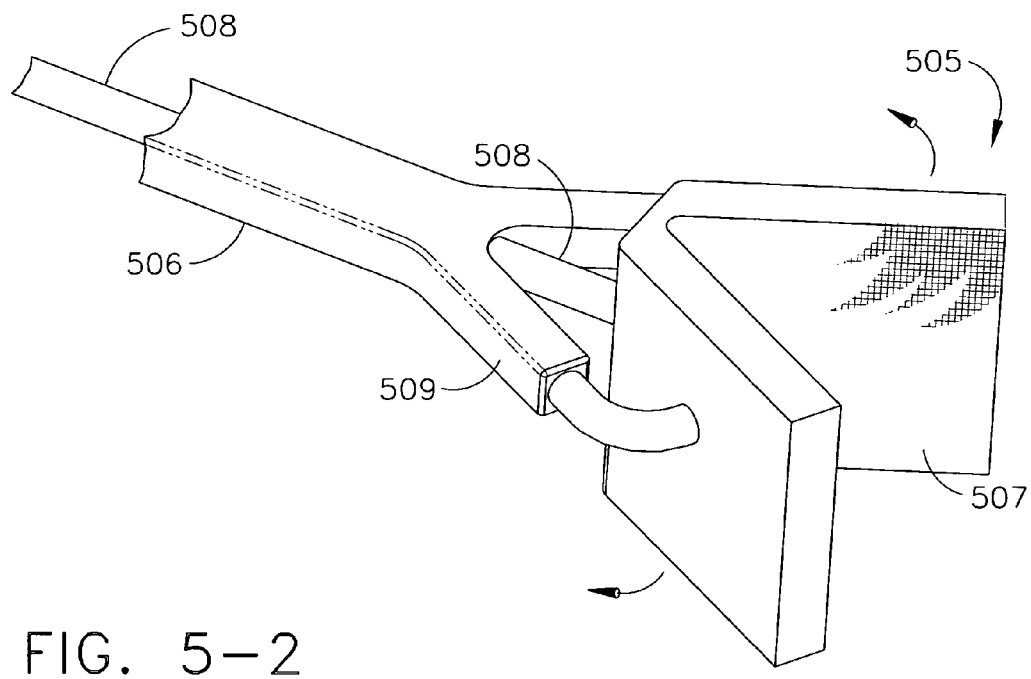
Figures 3, 5:
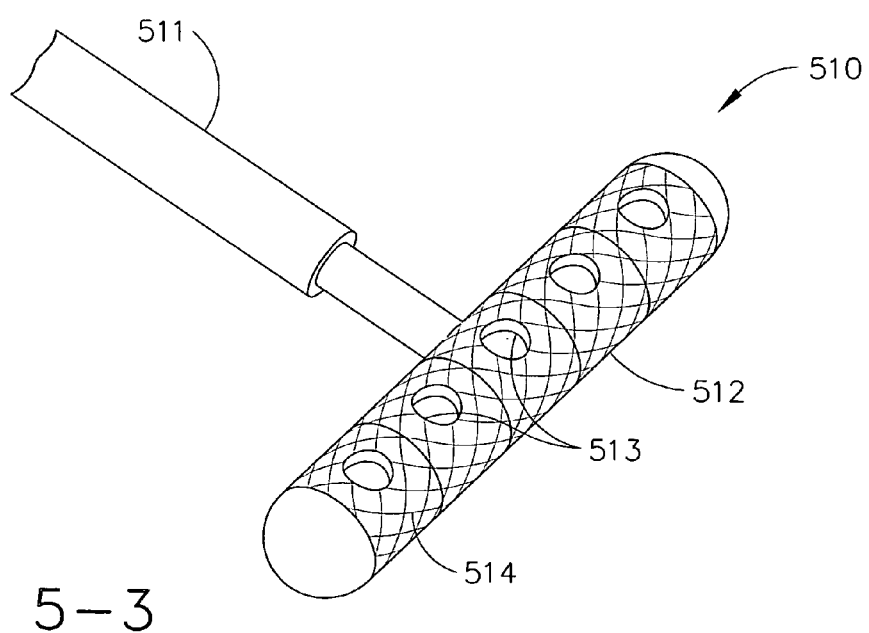
Figures 4, 5:
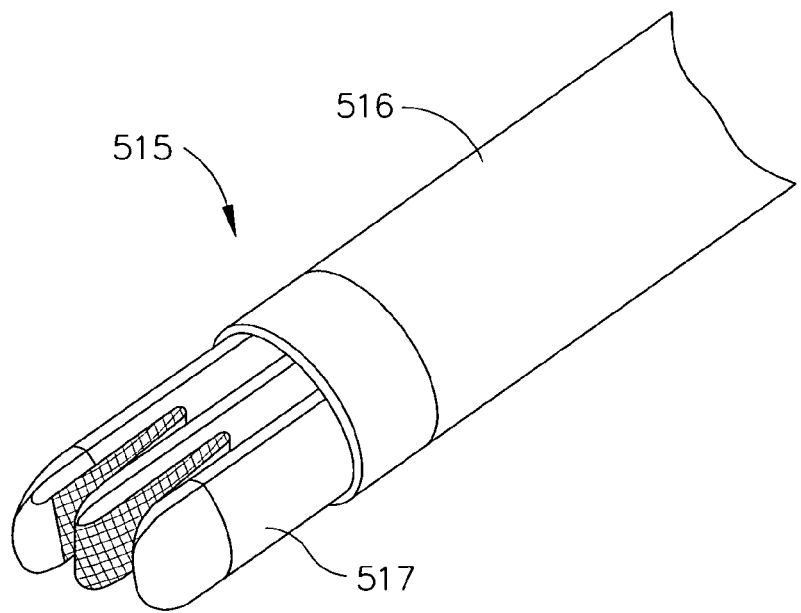
Figure 5:
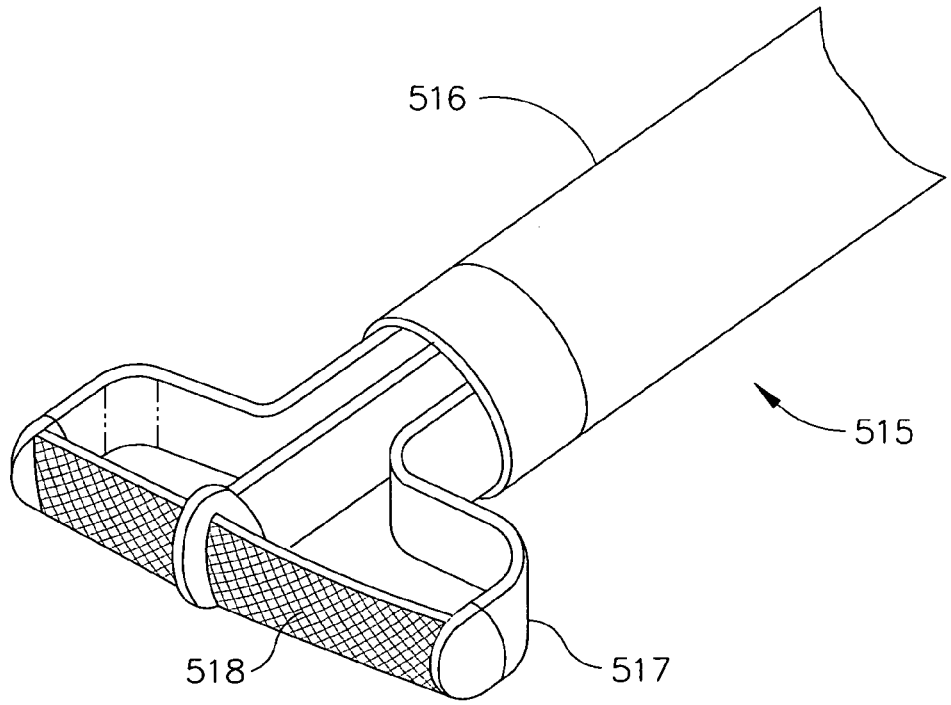
Figures 5, 6:
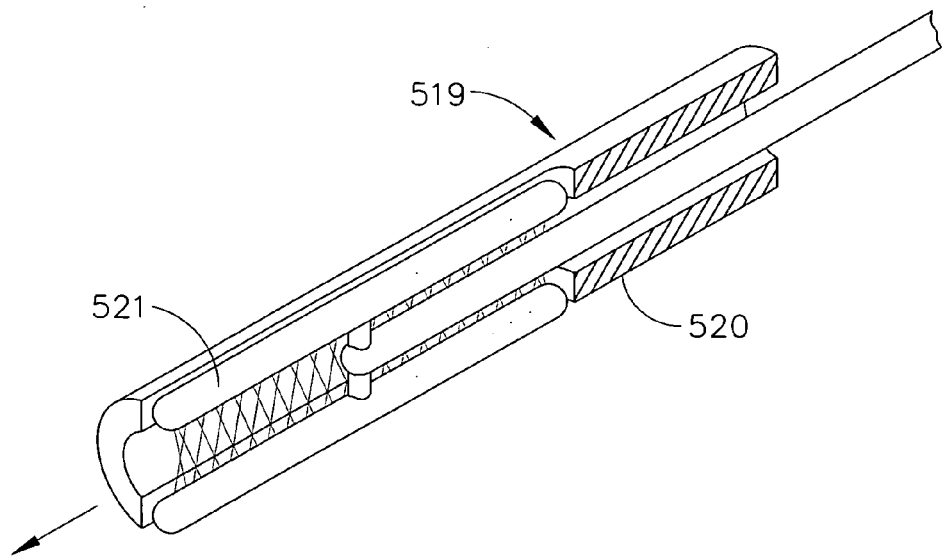
Figures 5, 6, 7:
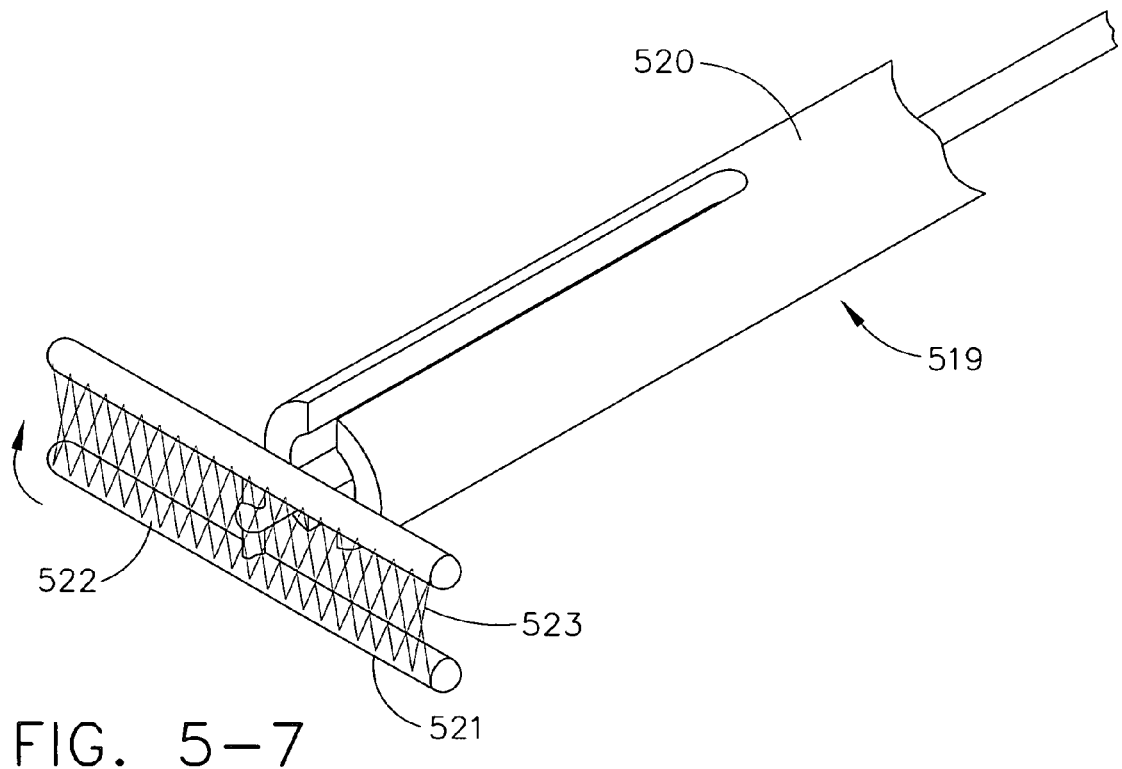
Figures 5, 6, 7, 8:
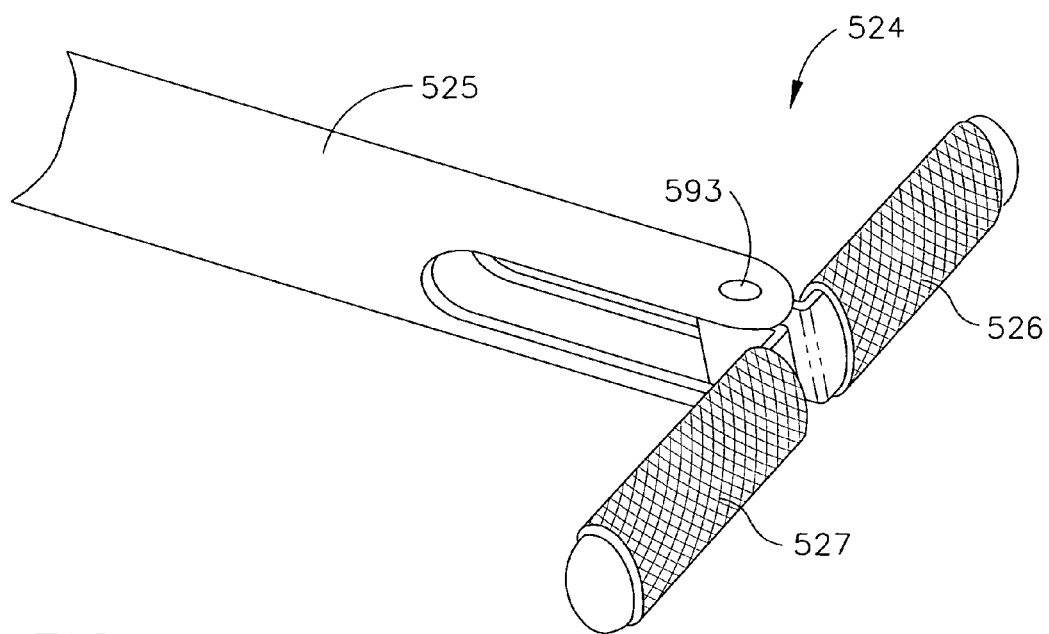
Figures 5, 6, 7, 8, 9:
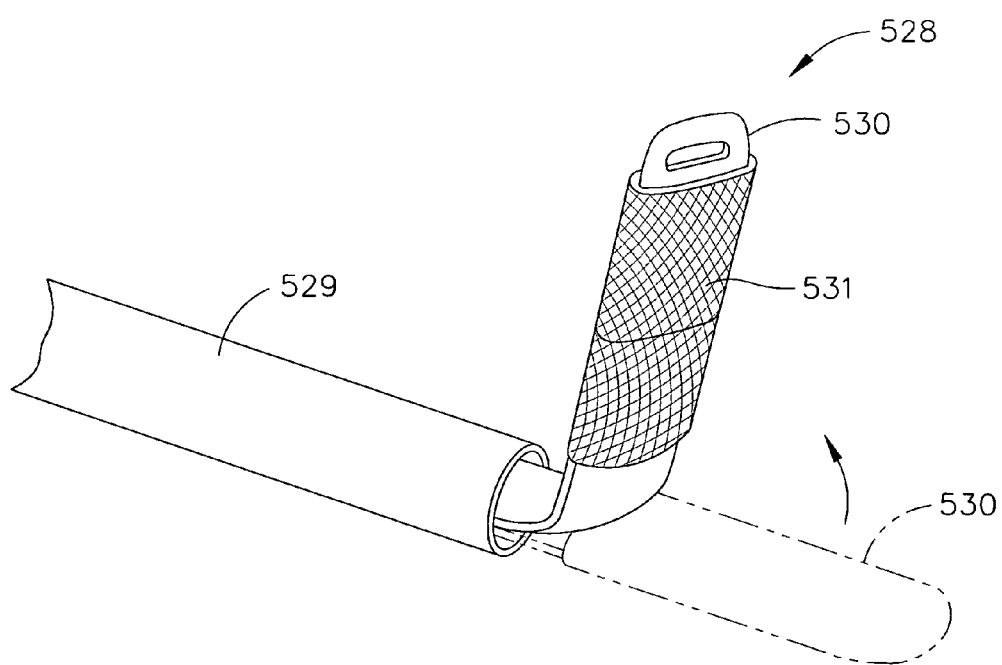
Figures 5, 6, 7, 8, 9, 10:
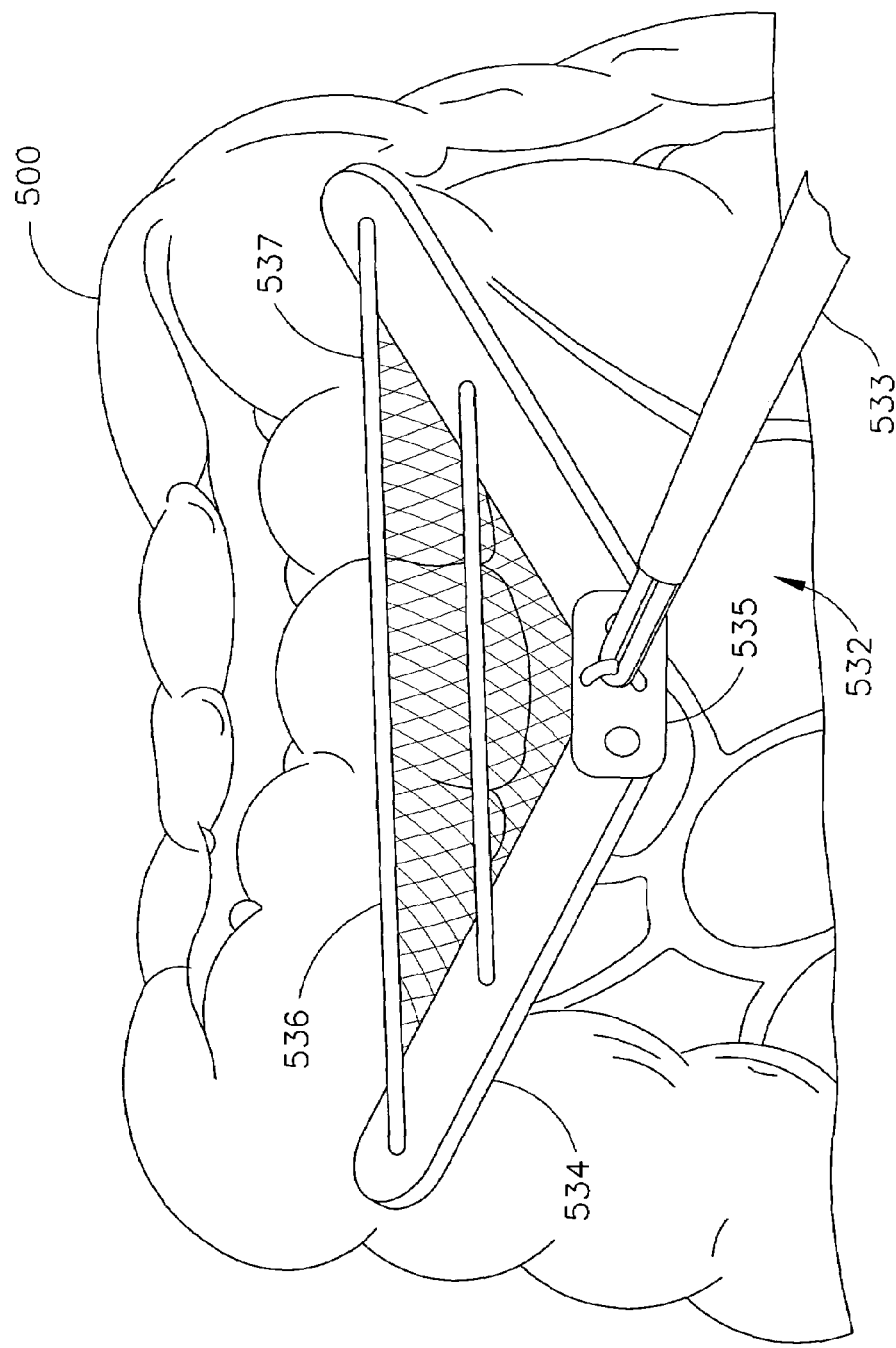
Figures 5, 6, 7, 8, 9, 10, 11:
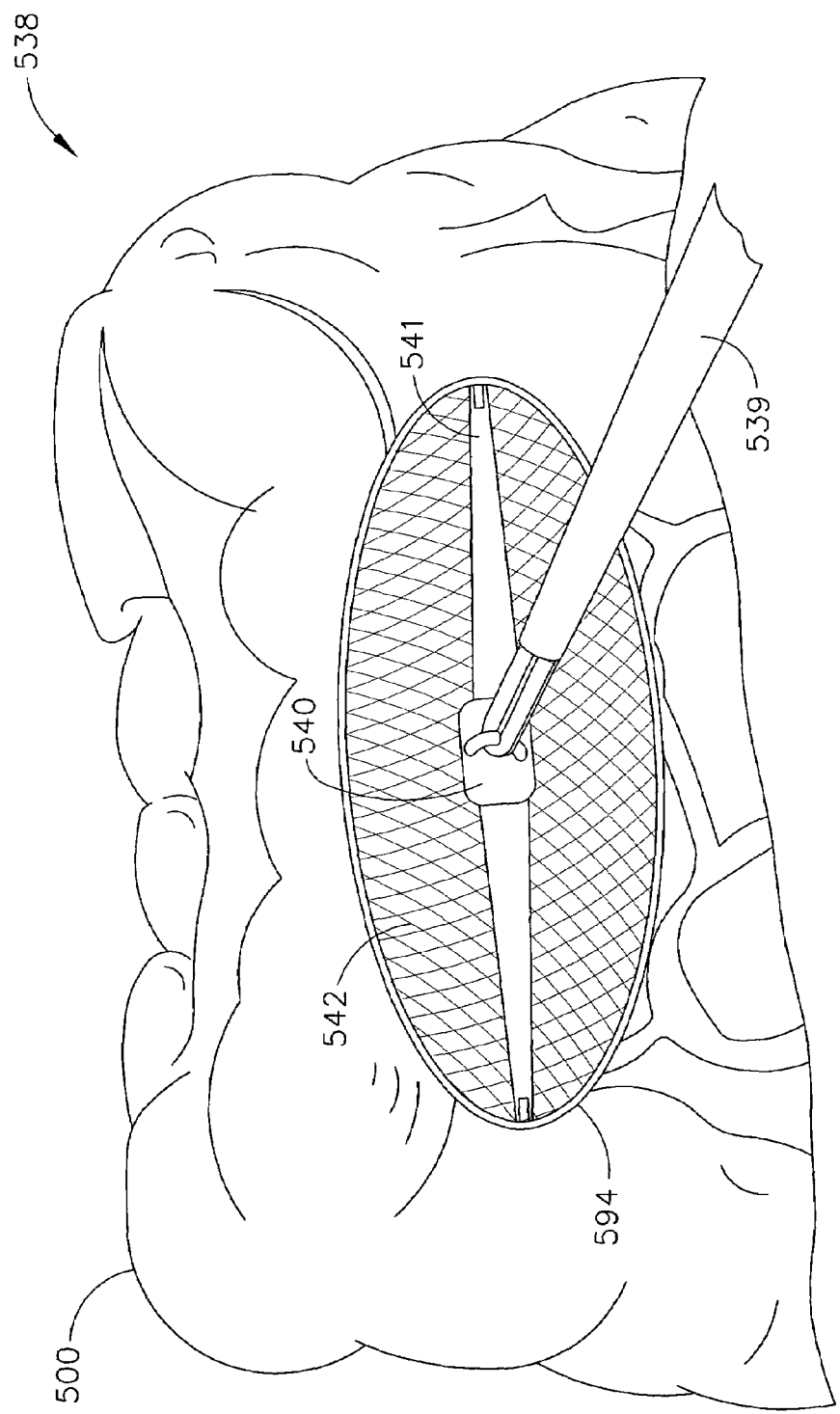
Figures 5, 6, 7, 8, 9, 10, 11, 12:
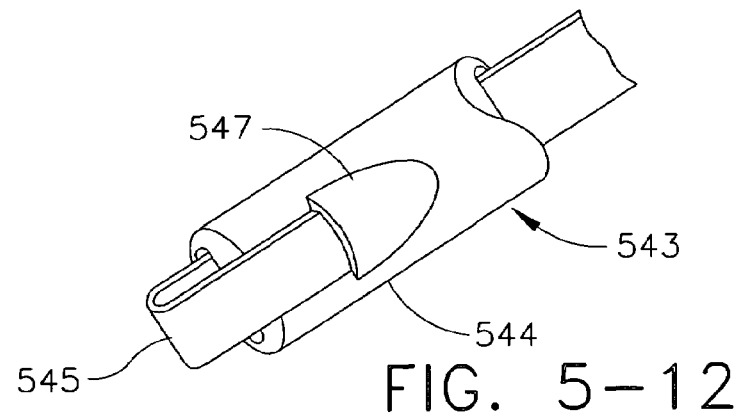
Figures 5, 6, 7, 8, 9, 10, 11, 12, 13, 13A:
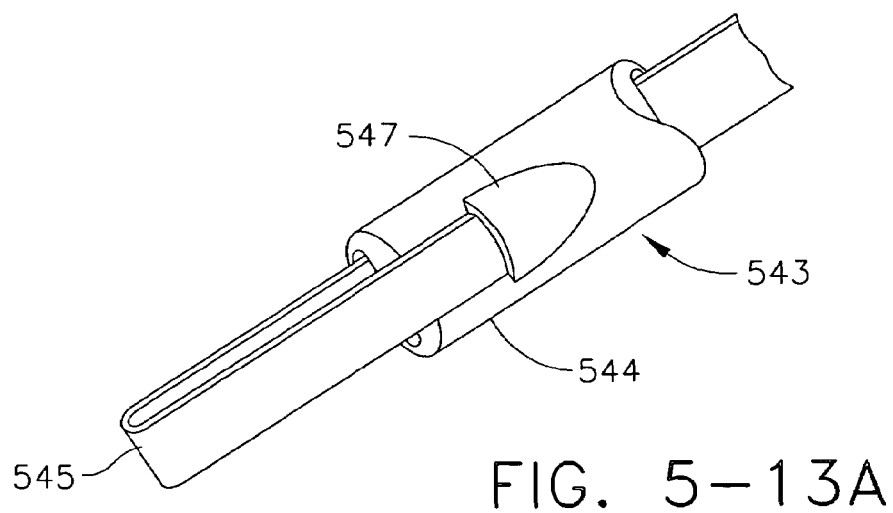
Figures 5, 6, 7, 8, 9, 10, 11, 12, 13, 13B:
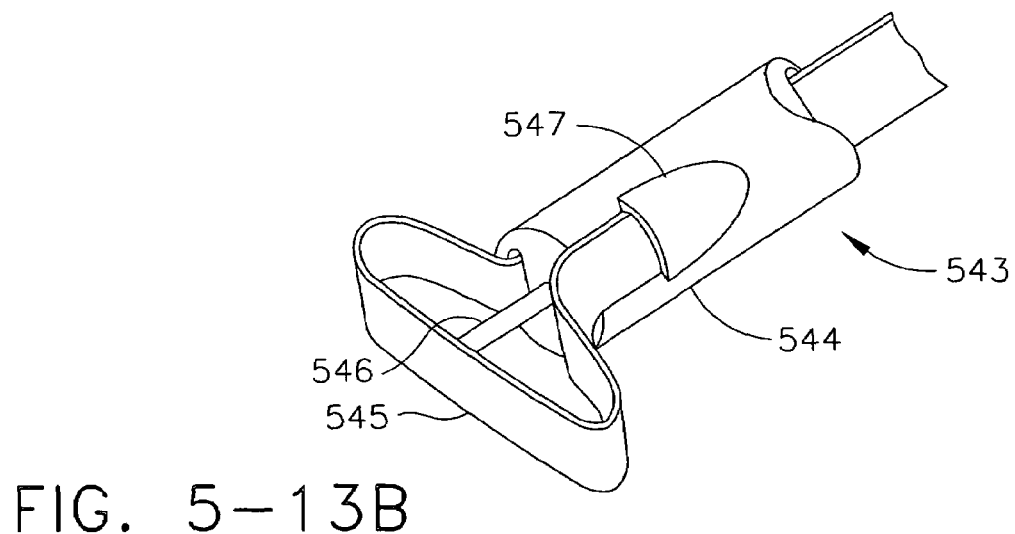
Figures 5, 6, 7, 8, 9, 10, 11, 12, 13, 14:
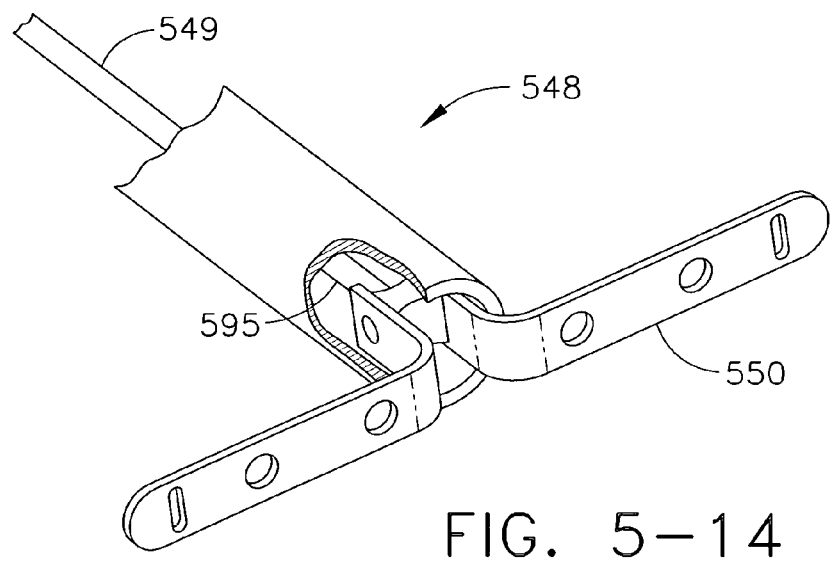
Figures 5, 6, 7, 8, 9, 10, 11, 12, 13, 14, 15:
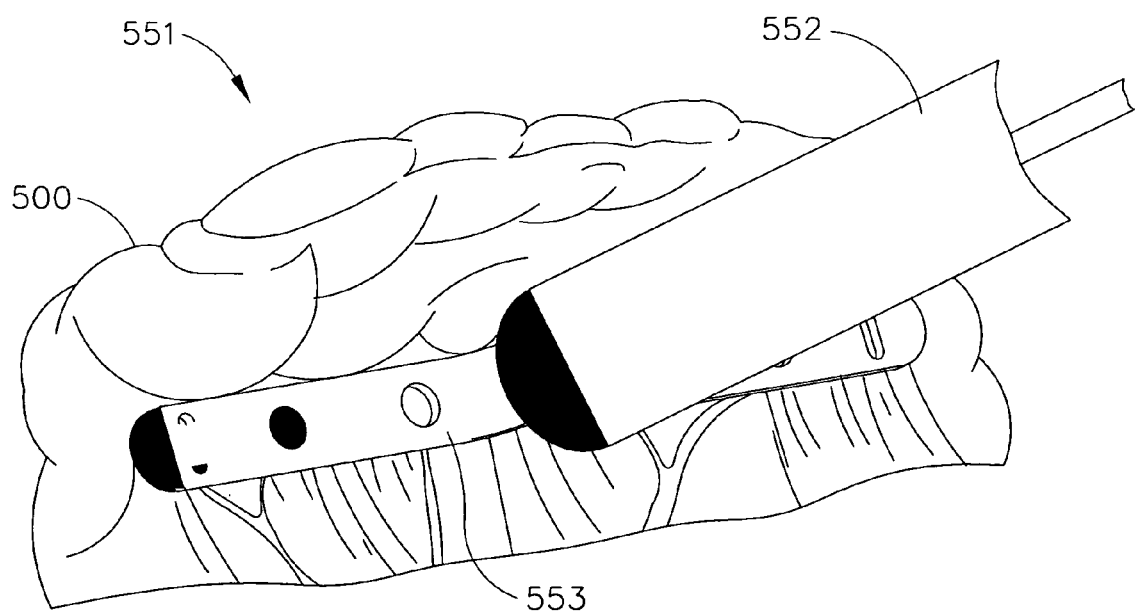
Figures 5, 6, 7, 8, 9, 10, 11, 12, 13, 14, 15, 16:
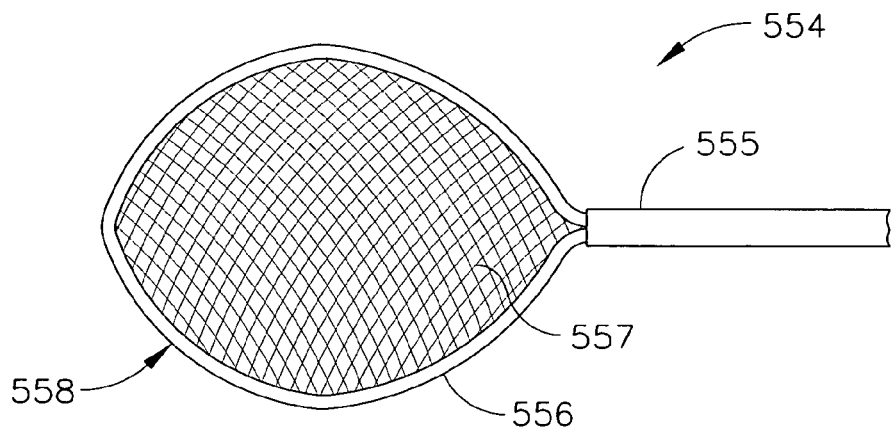
Figures 5, 6, 7, 8, 9, 10, 11, 12, 13, 14, 15, 16, 17:
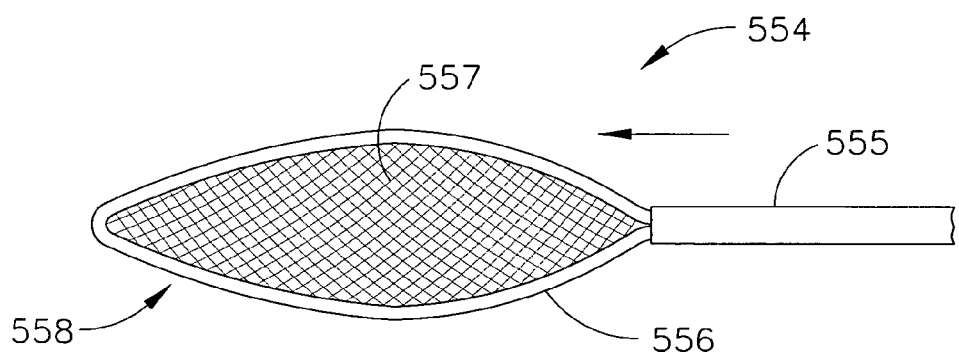
Figures 5, 6, 7, 8, 9, 10, 11, 12, 13, 14, 15, 16, 17, 18:
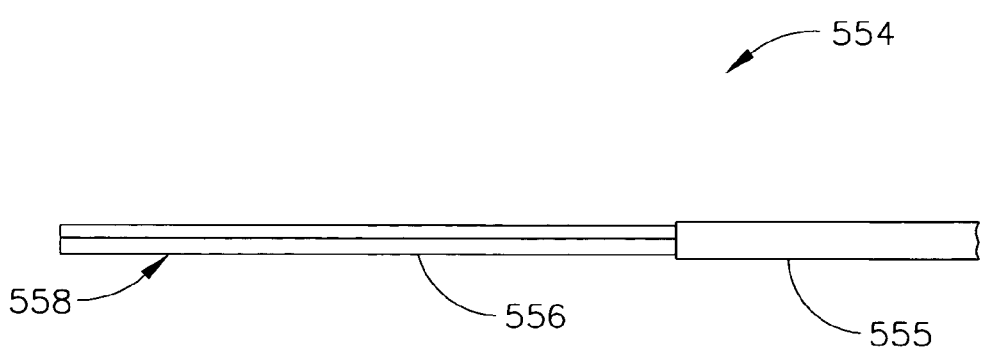
Figures 5, 6, 7, 8, 9, 10, 11, 12, 13, 14, 15, 16, 17, 18, 19:
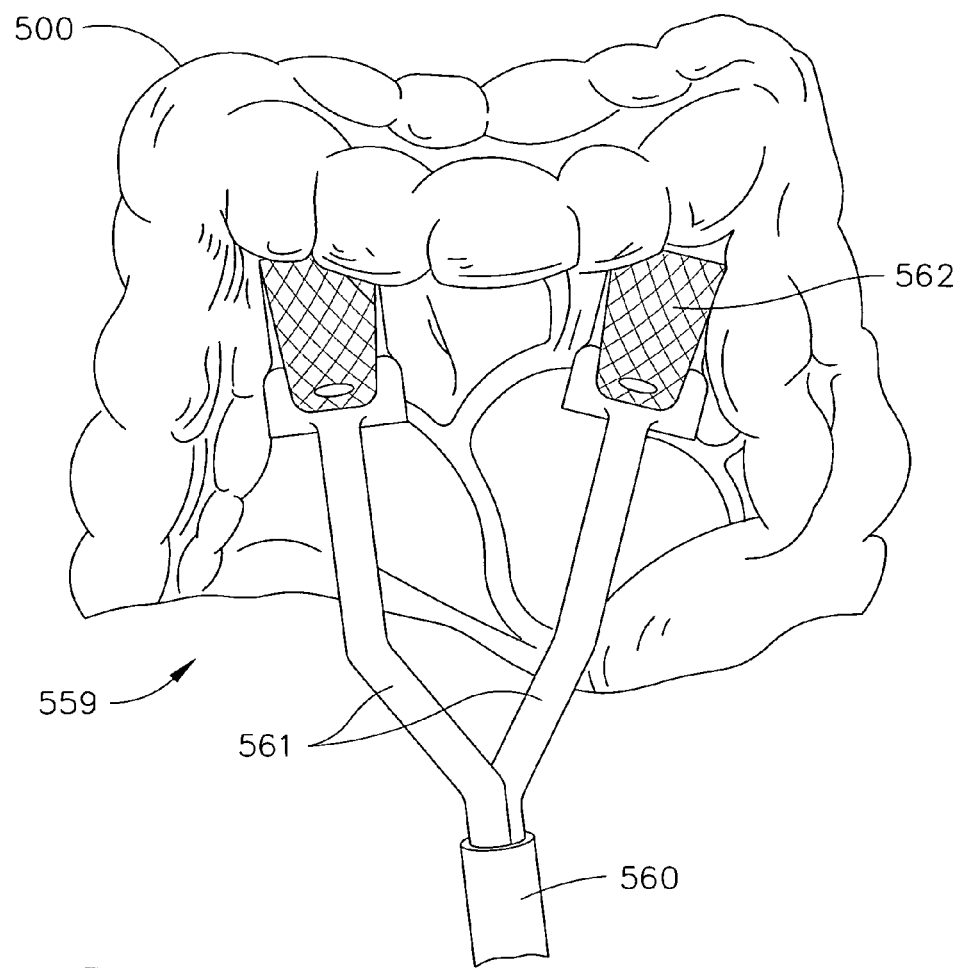
Figures 5, 6, 7, 8, 9, 10, 11, 12, 13, 14, 15, 16, 17, 18, 19, 20:
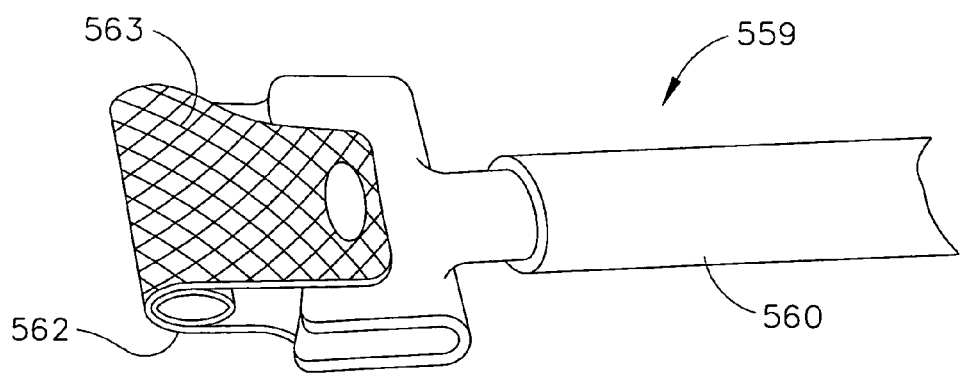
Figures 5, 6, 7, 8, 9, 10, 11, 12, 13, 14, 15, 16, 17, 18, 19, 20, 21, 22, 23, 24:
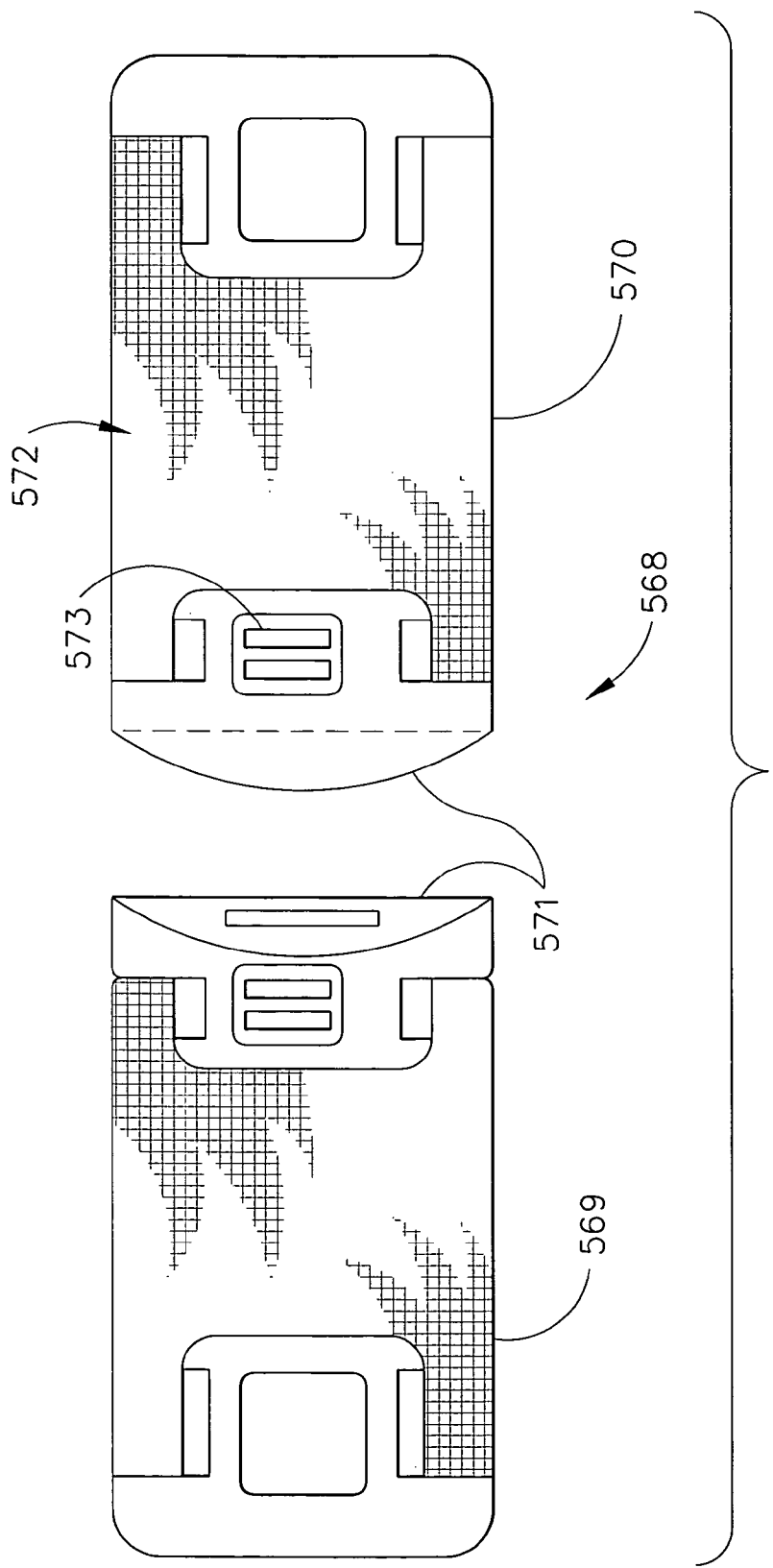
Figures 5, 6, 7, 8, 9, 10, 11, 12, 13, 14, 15, 16, 17, 18, 19, 20, 21, 22, 23, 24, 25, 26, 27:
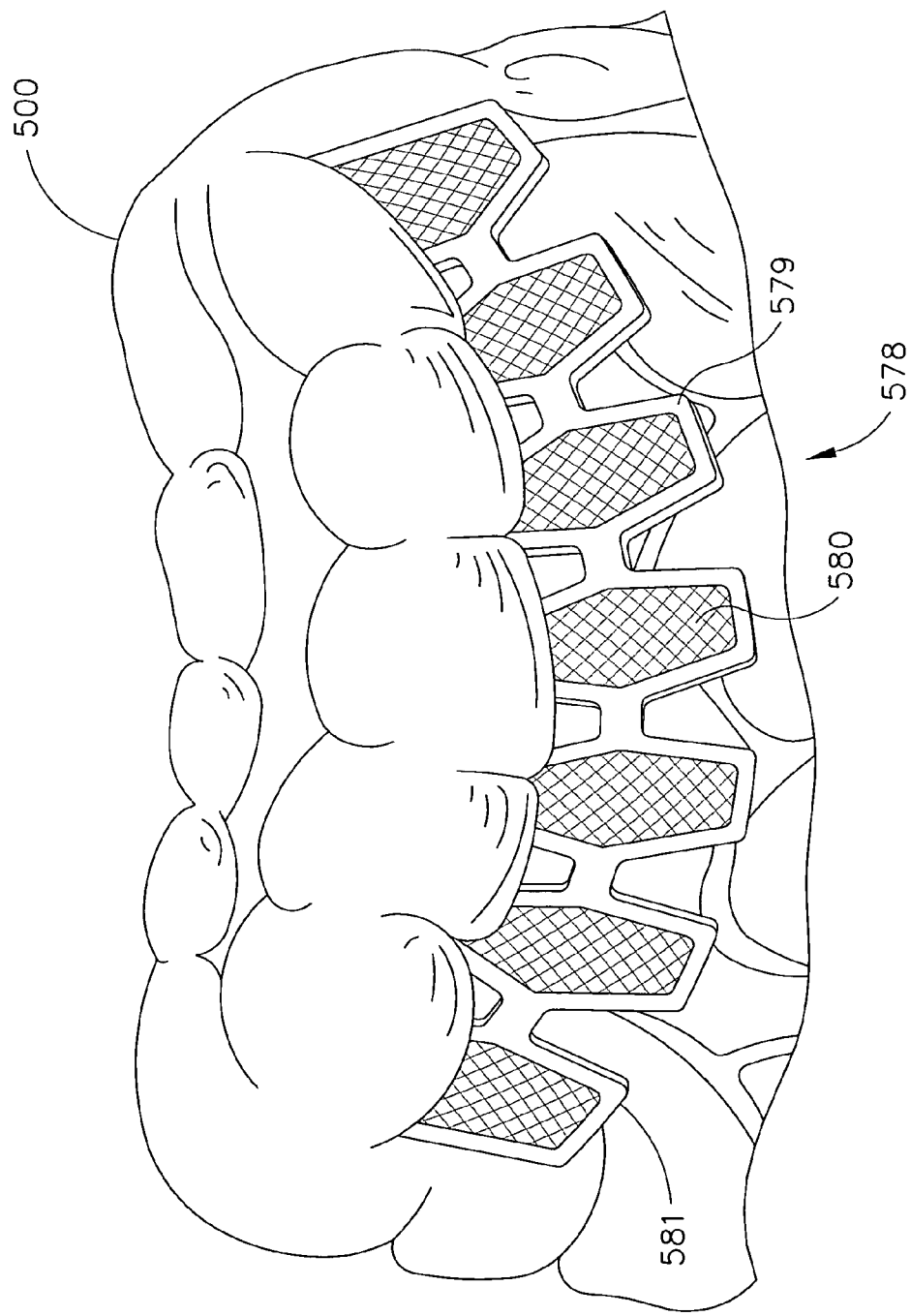
Figures 5, 6, 7, 8, 9, 10, 11, 12, 13, 14, 15, 16, 17, 18, 19, 20, 21, 22, 23, 24, 25, 26, 27, 28:
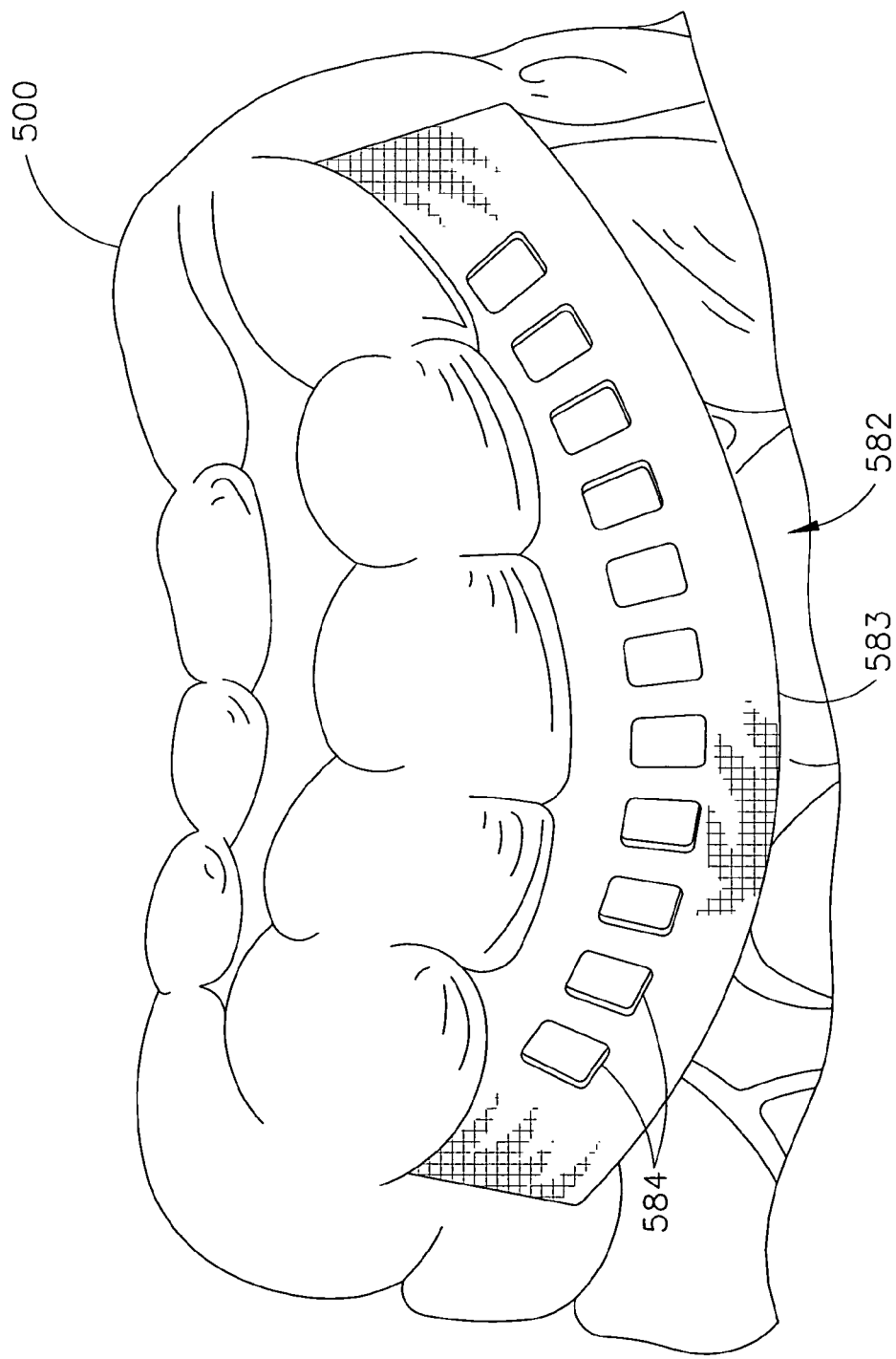
Figures 5, 6, 7, 8, 9, 10, 11, 12, 13, 14, 15, 16, 17, 18, 19, 20, 21, 22, 23, 24, 25, 26, 27, 28, 29:
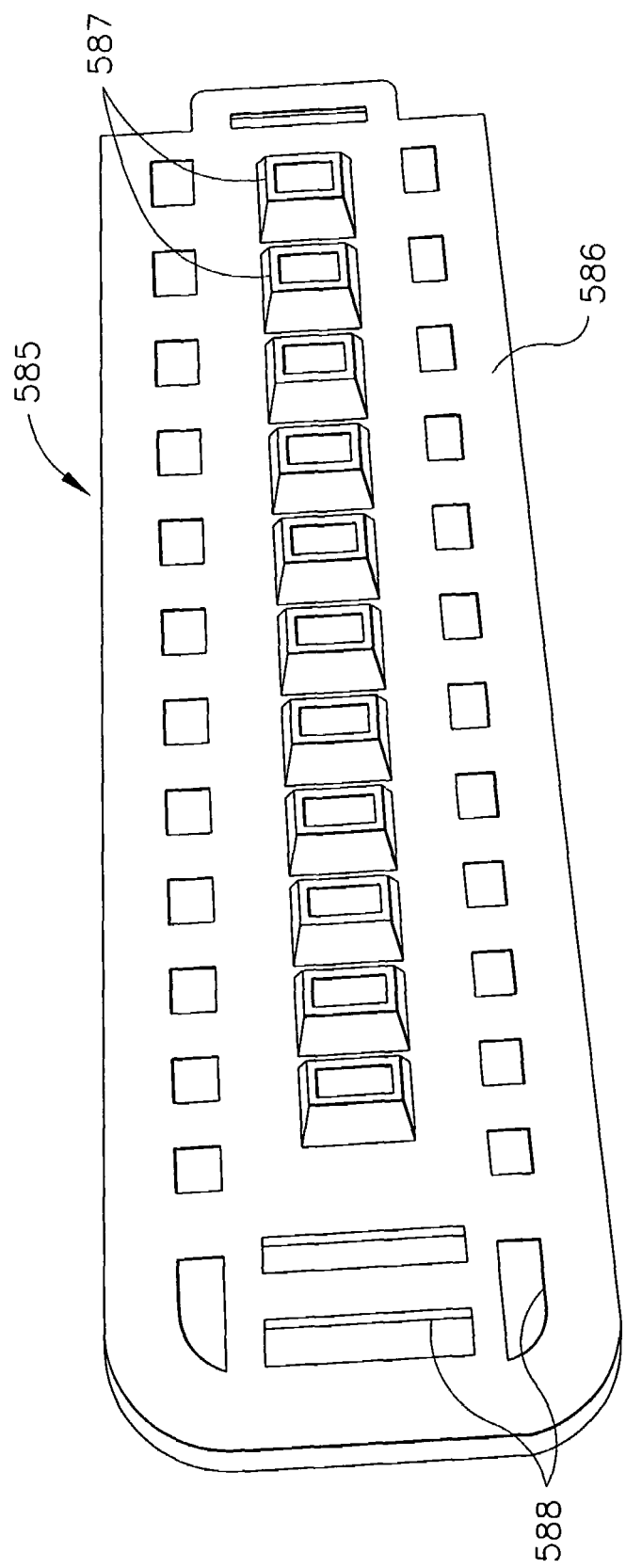
Figures 5, 6, 7, 8, 9, 10, 11, 12, 13, 14, 15, 16, 17, 18, 19, 20, 21, 22, 23, 24, 25, 26, 27, 28, 29, 30:
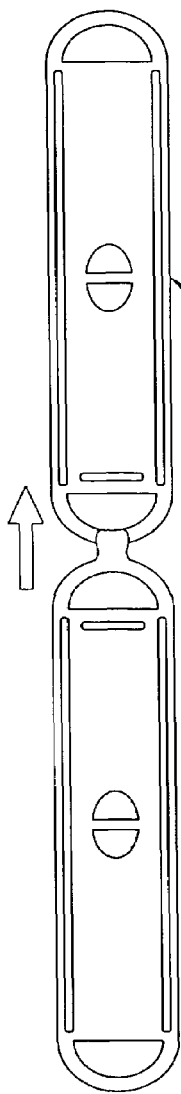
Figures 5, 6, 7, 8, 9, 10, 11, 12, 13, 14, 15, 16, 17, 18, 19, 20, 21, 22, 23, 24, 25, 26, 27, 28, 29, 30, 31:
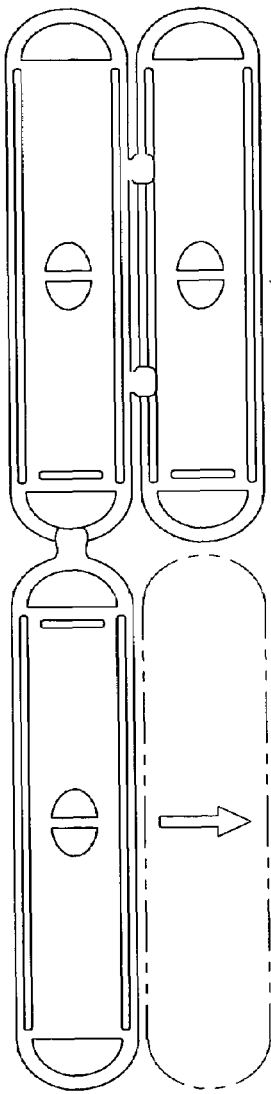
Figures 5, 6, 7, 8, 9, 10, 11, 12, 13, 14, 15, 16, 17, 18, 19, 20, 21, 22, 23, 24, 25, 26, 27, 28, 29, 30, 31, 32:
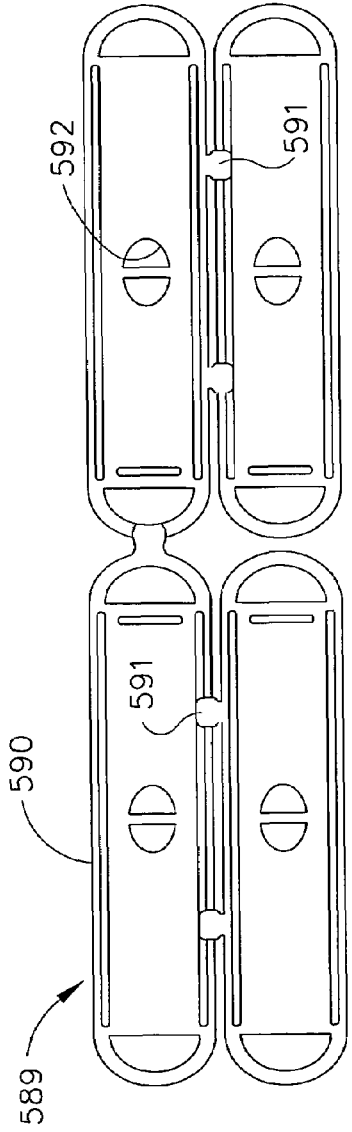
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33:
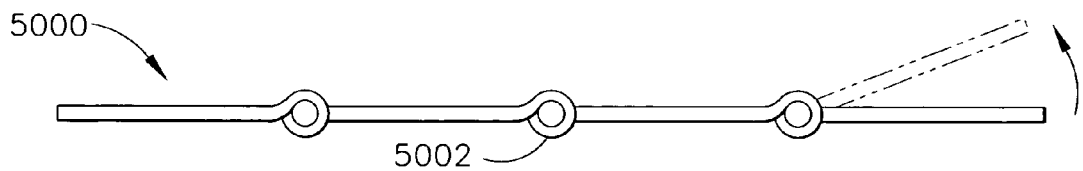
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34:
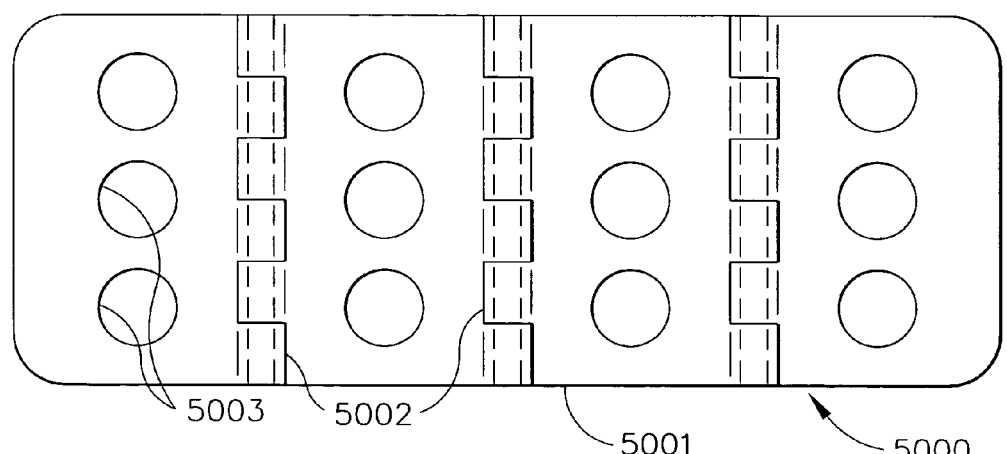
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35:
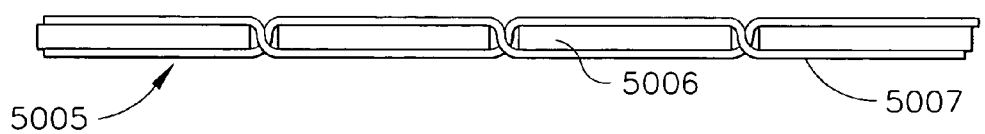
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36:
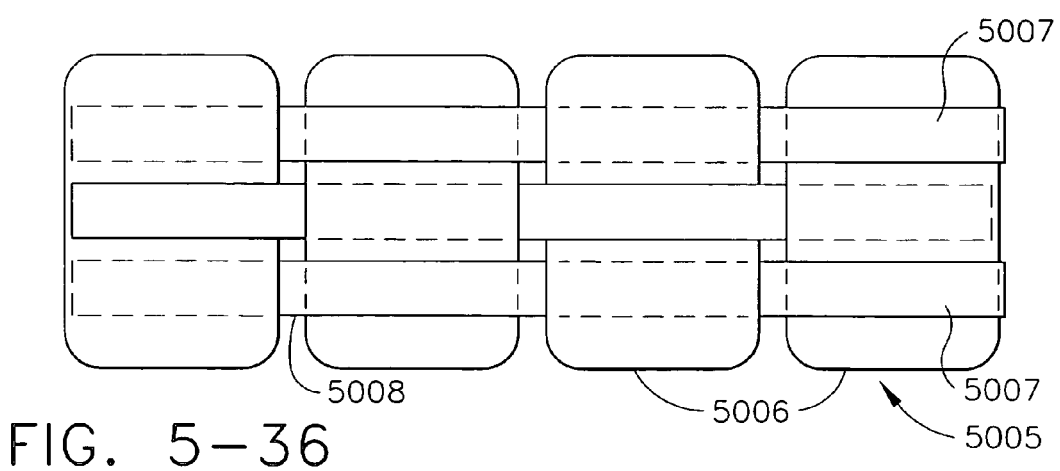
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 37A:
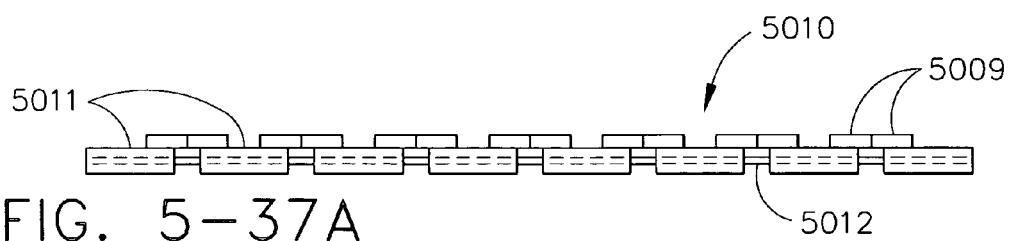
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38:
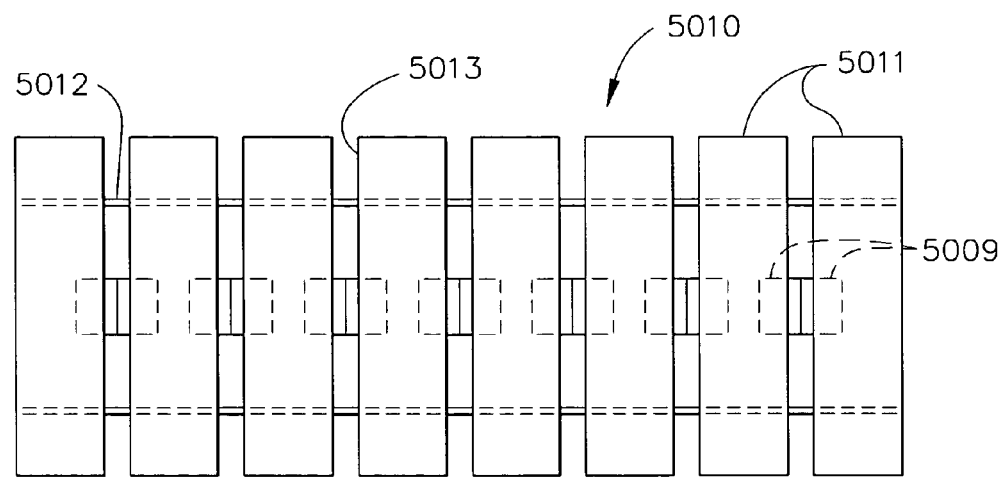
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 37B:
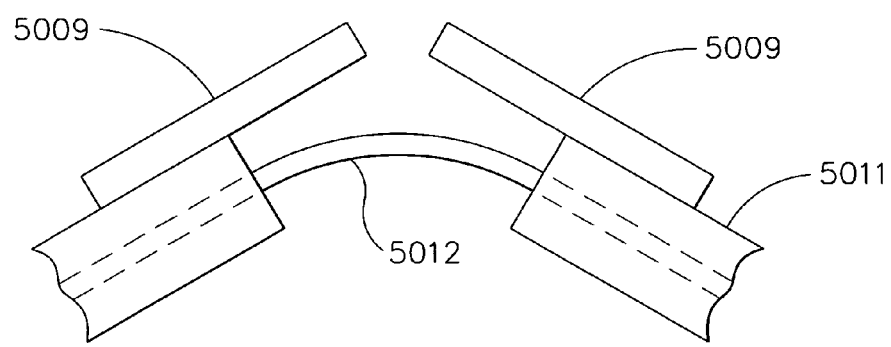
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41:
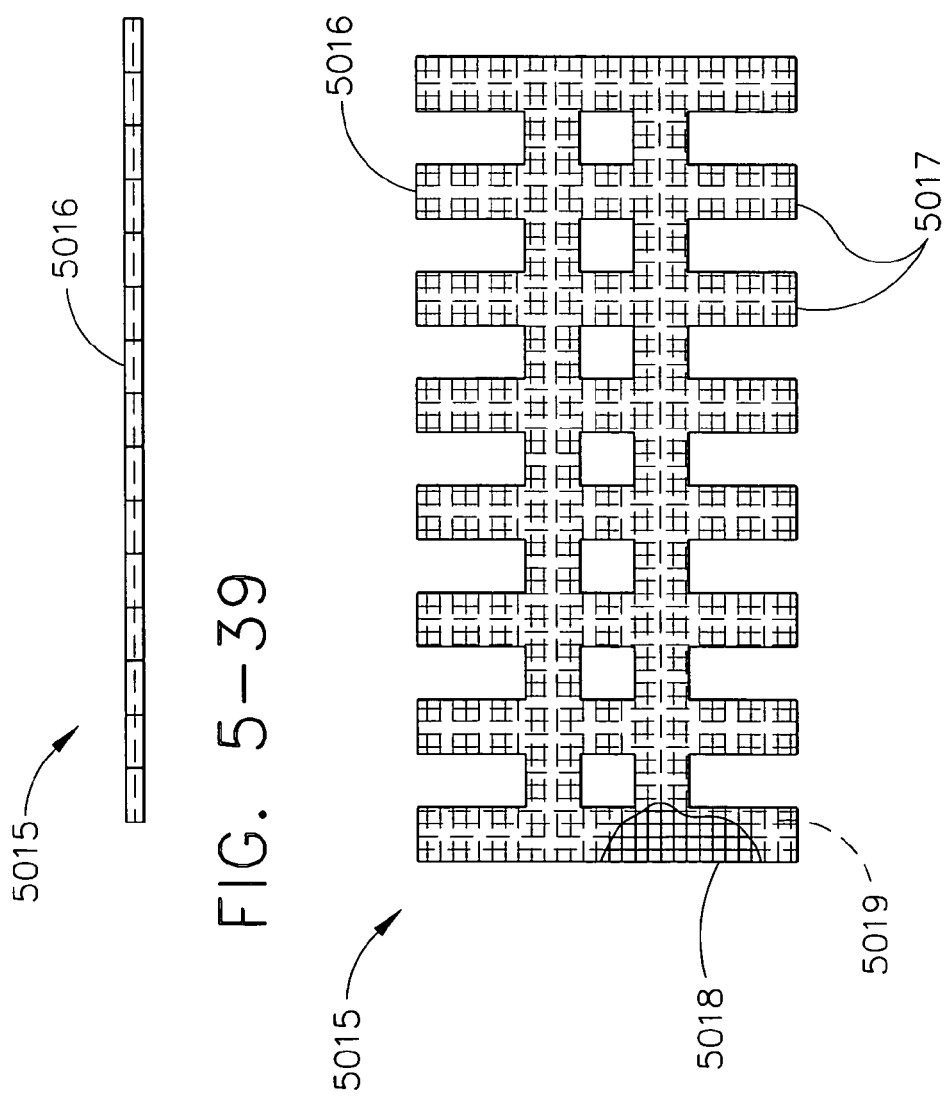
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42:
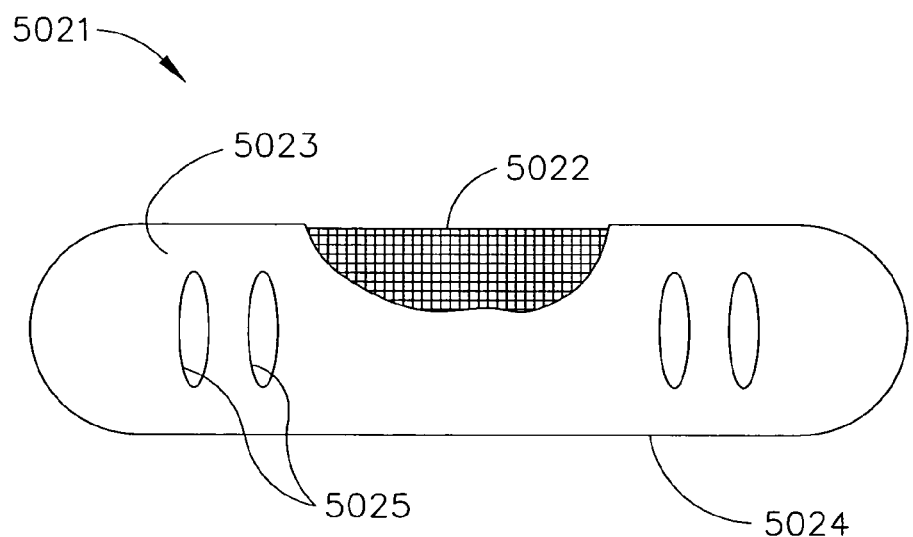
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43:
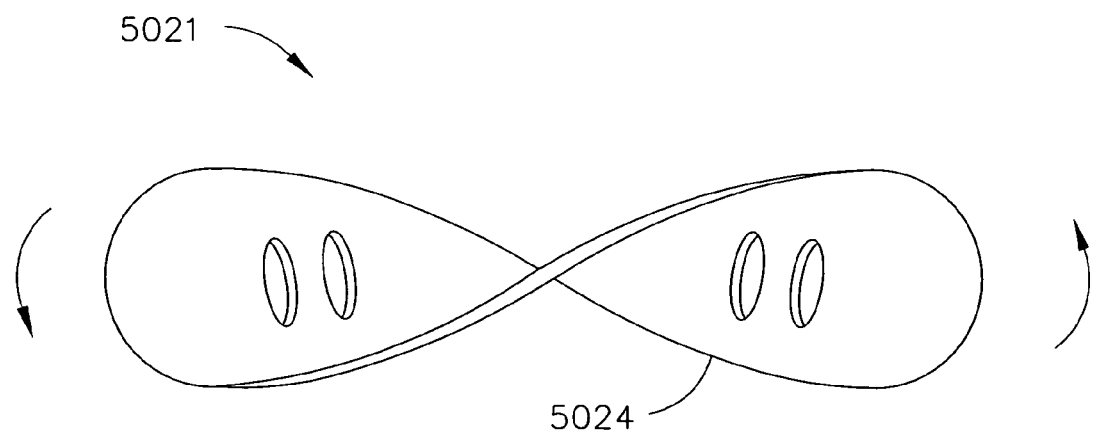
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44:
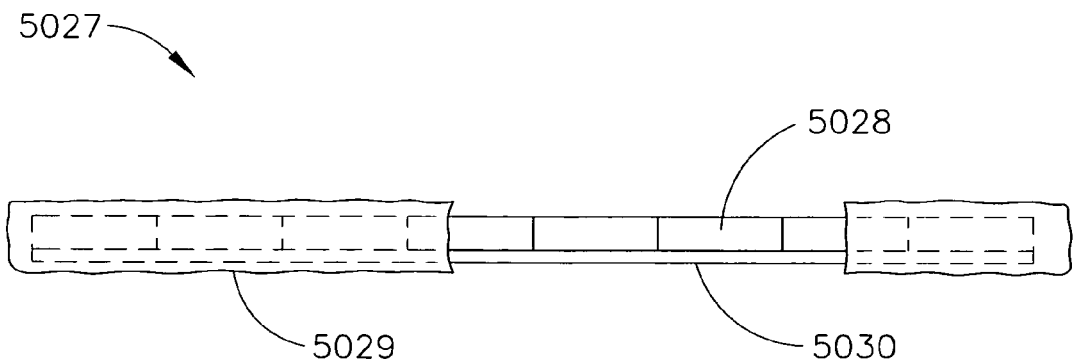
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45:
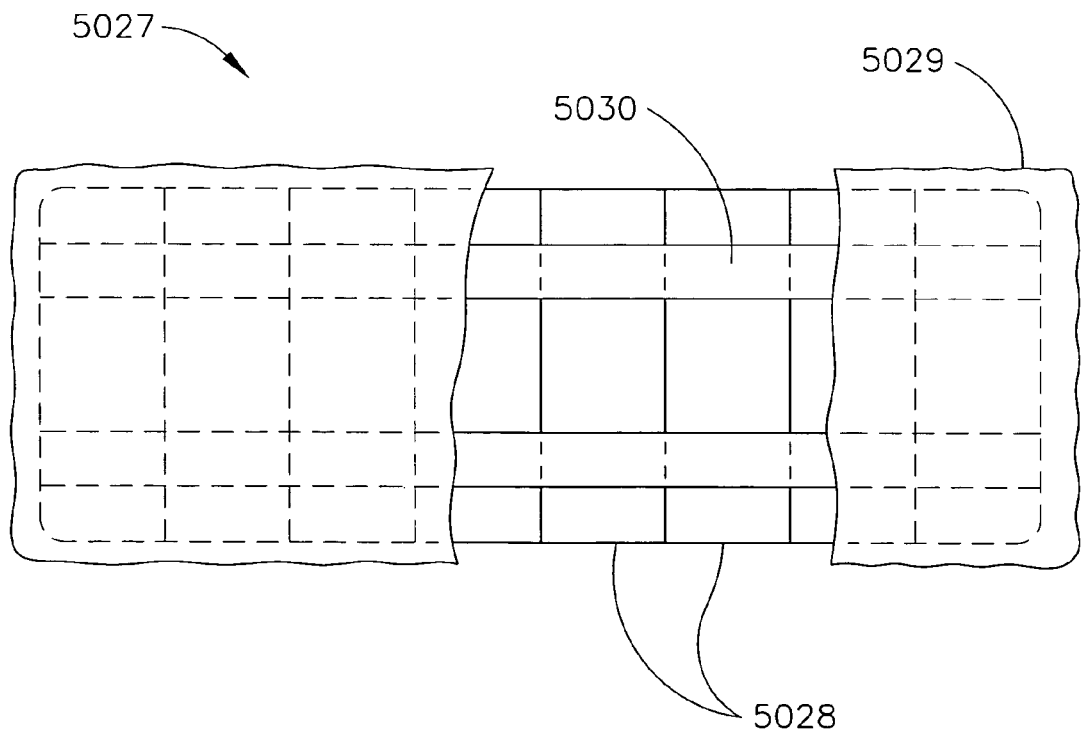
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46:
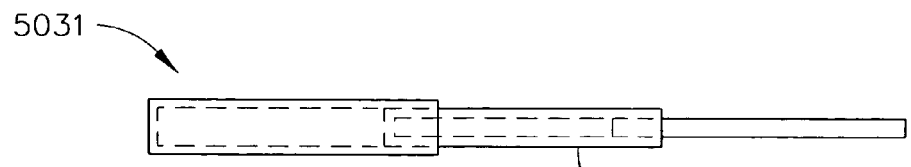
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47:
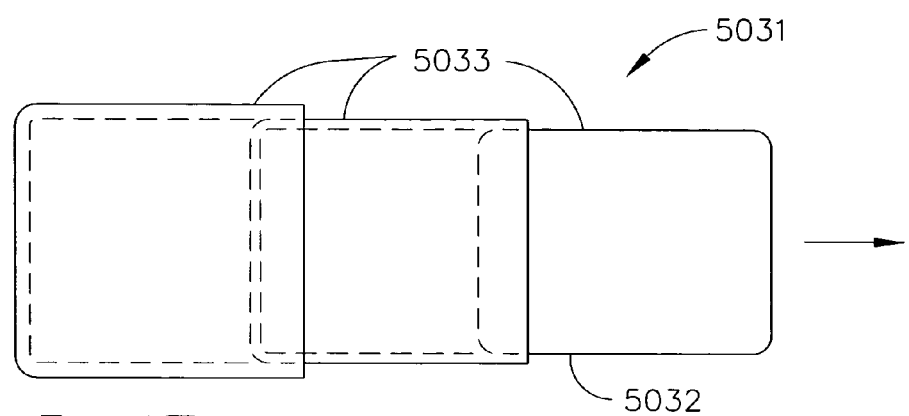
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48:
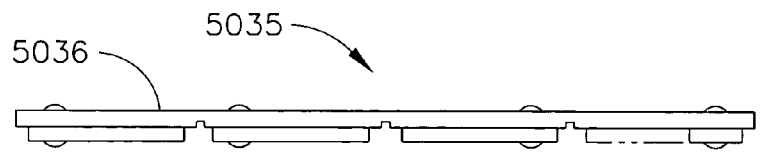
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49:
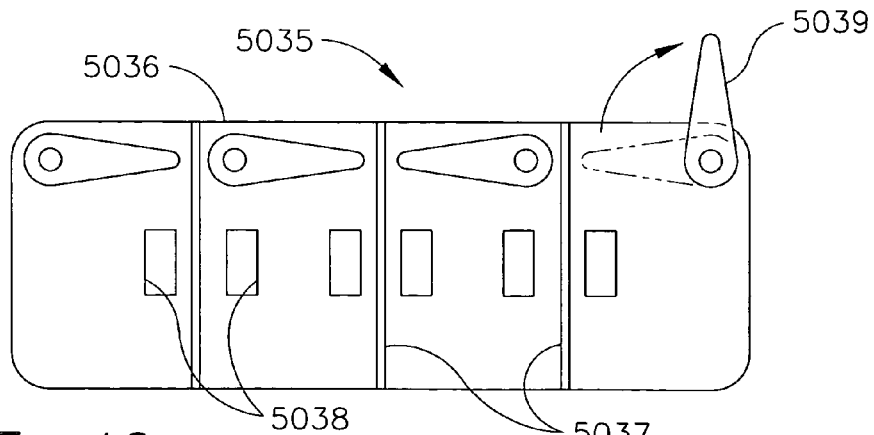
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50:
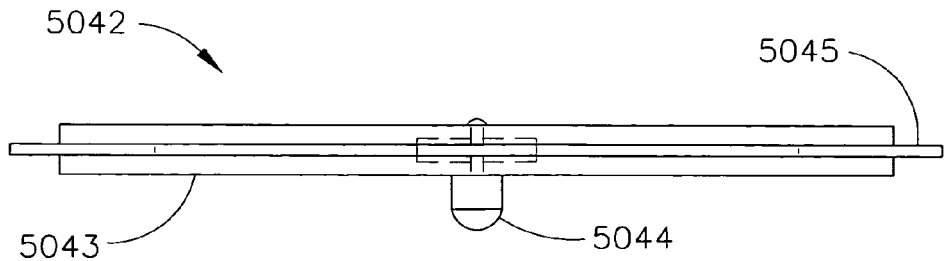
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51:
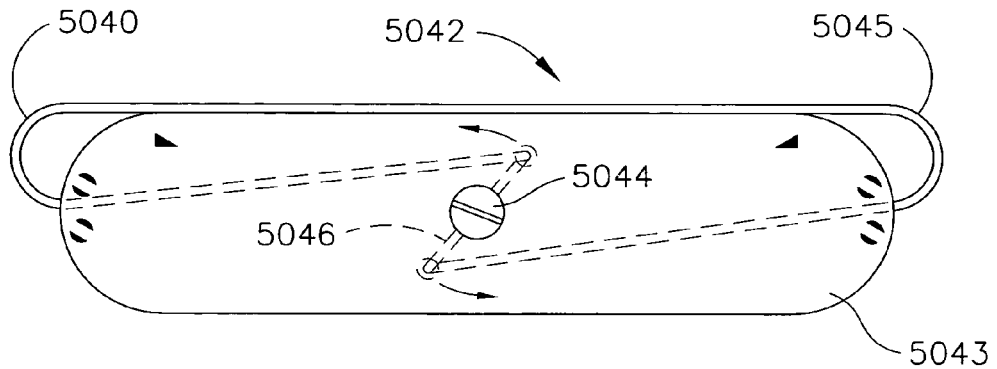
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52:
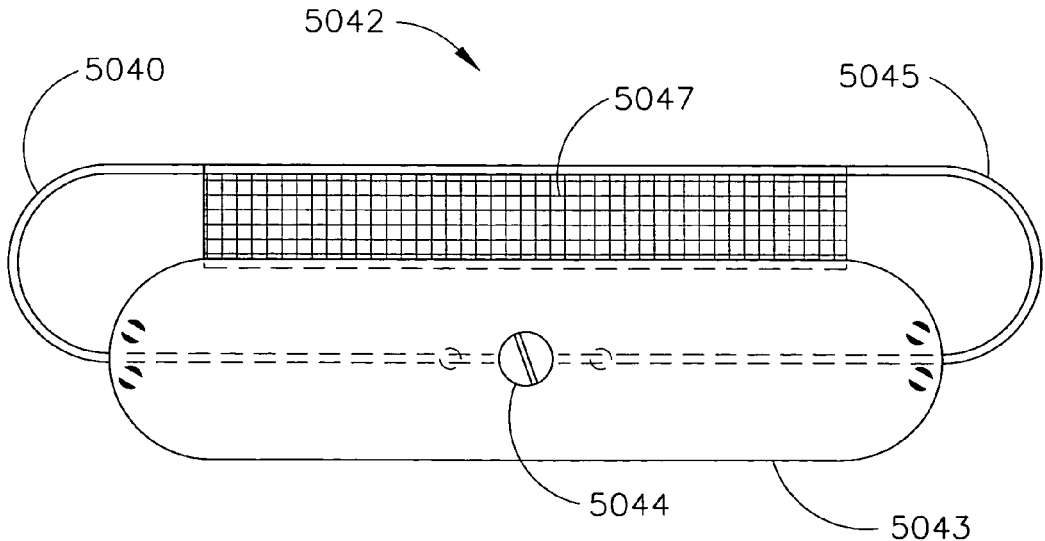
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53:
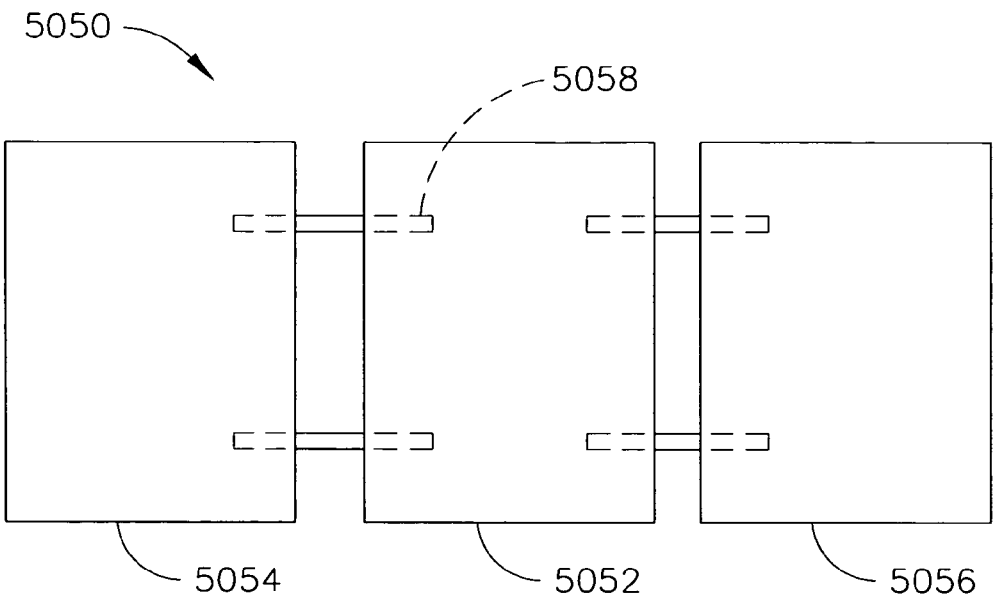
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54:
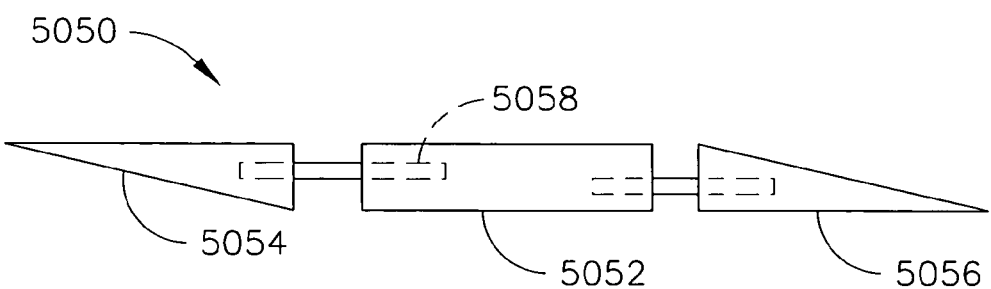
Figures 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55:
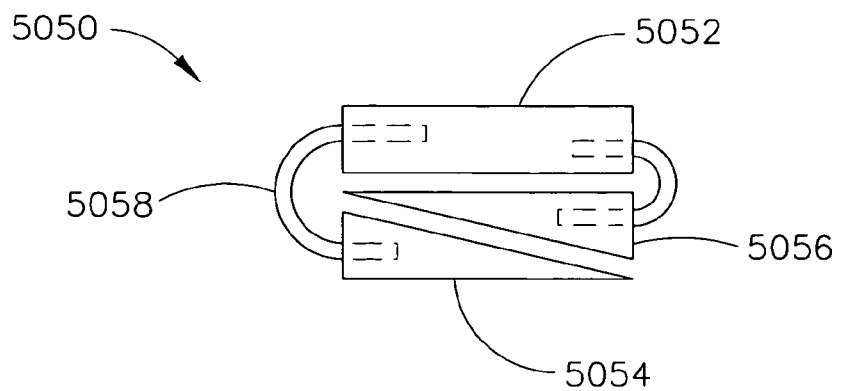
Figures 5, 56, 57:
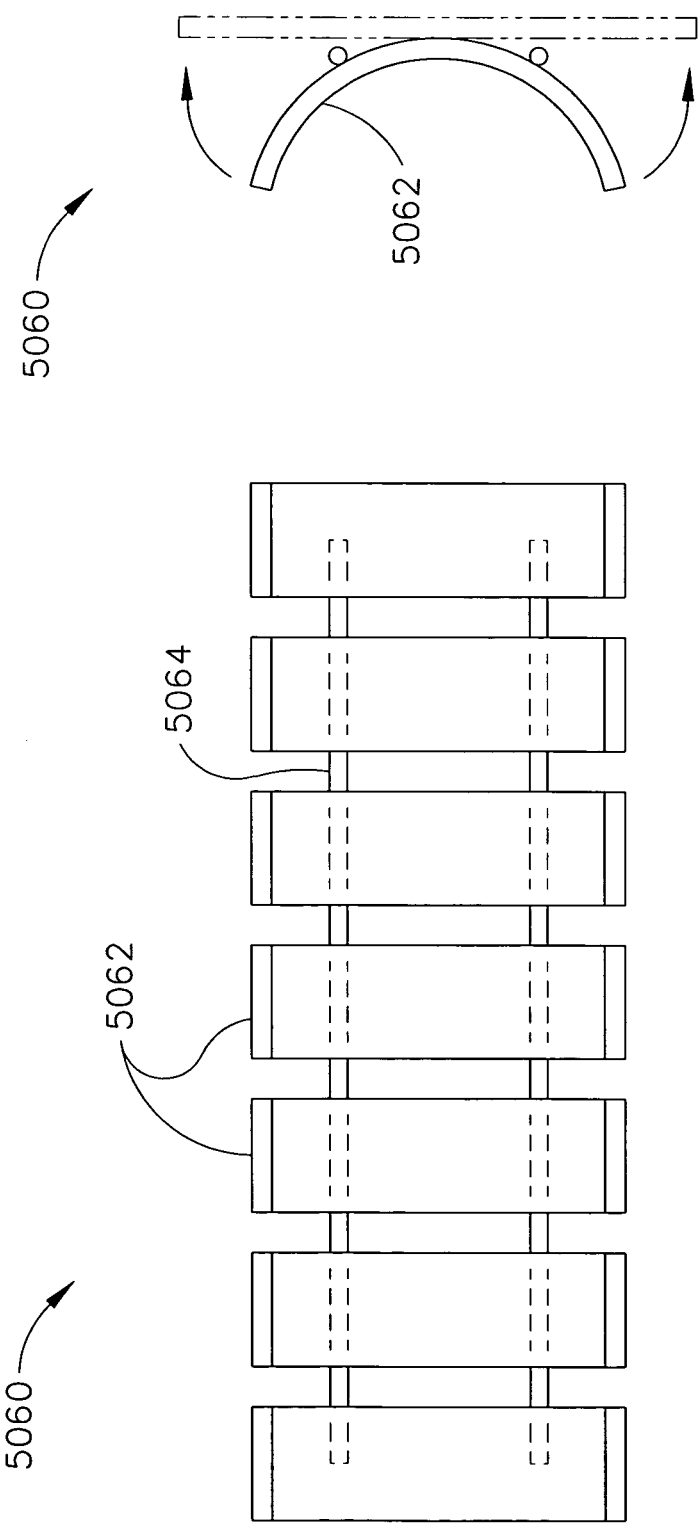
Figures 3, 6:
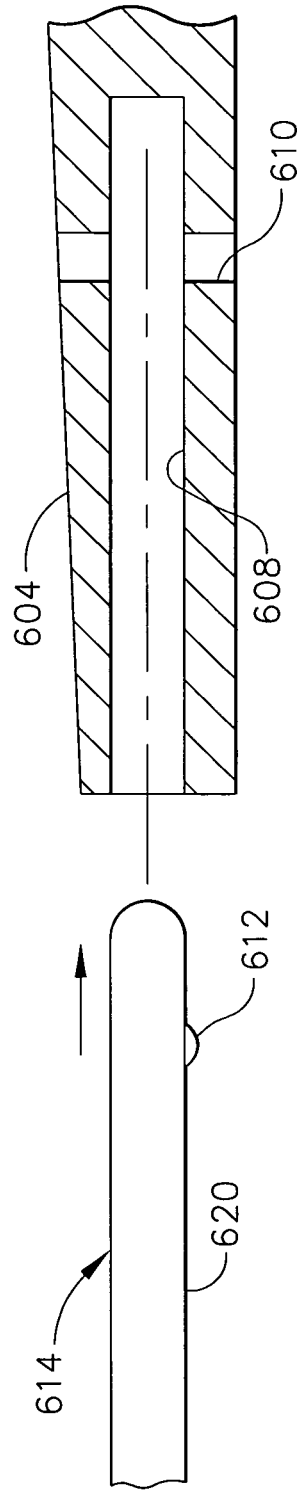
Figures 4, 6:
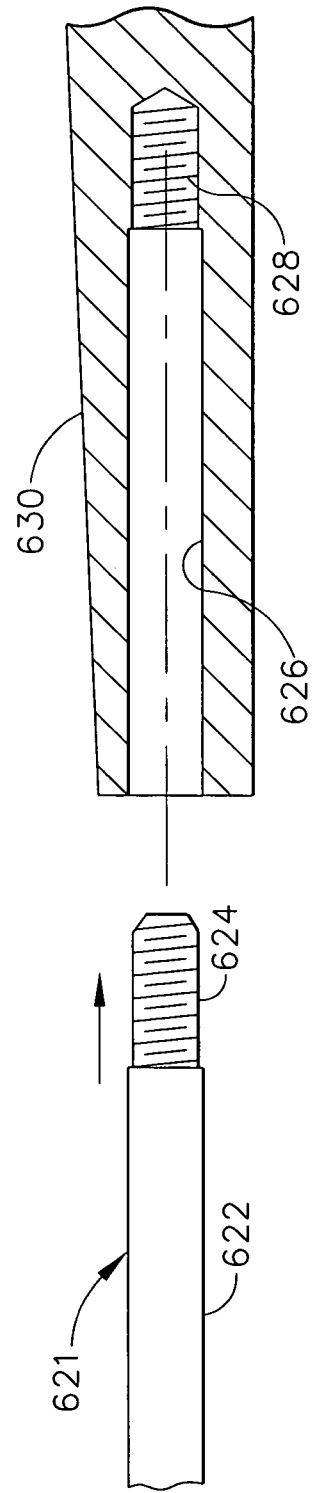
Figures 6, 7, 8, 9:
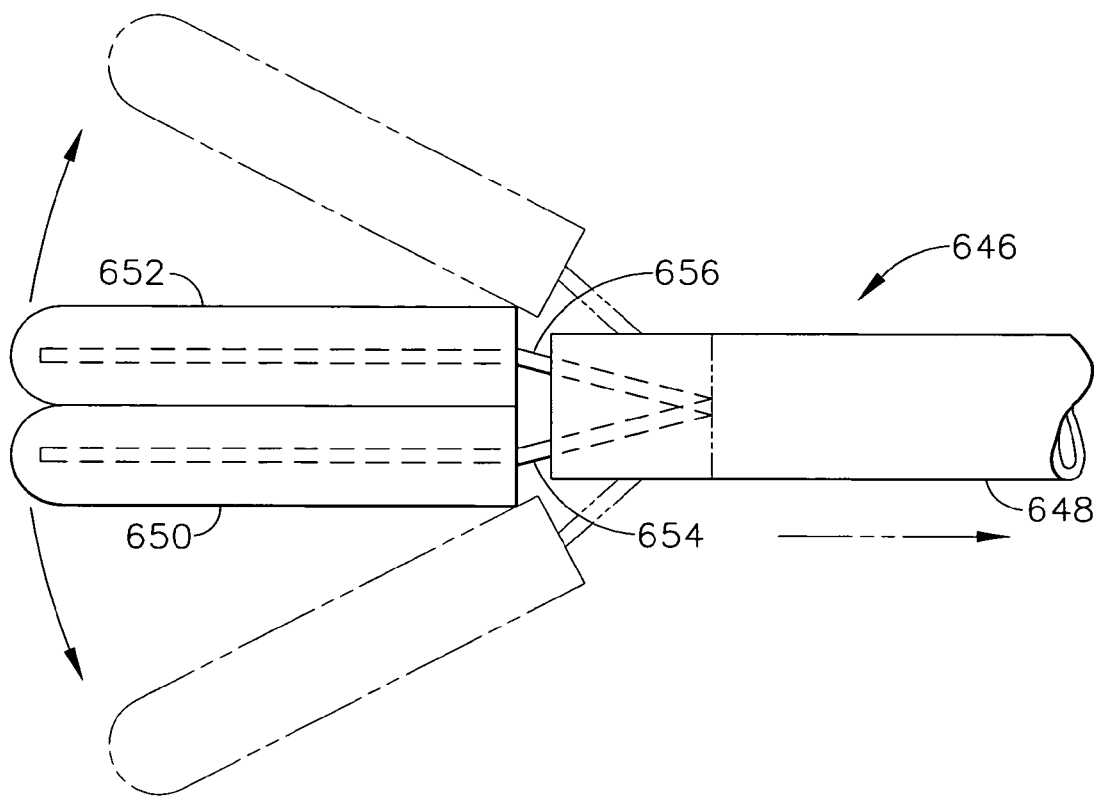
Figures 6, 7, 8, 9, 10:
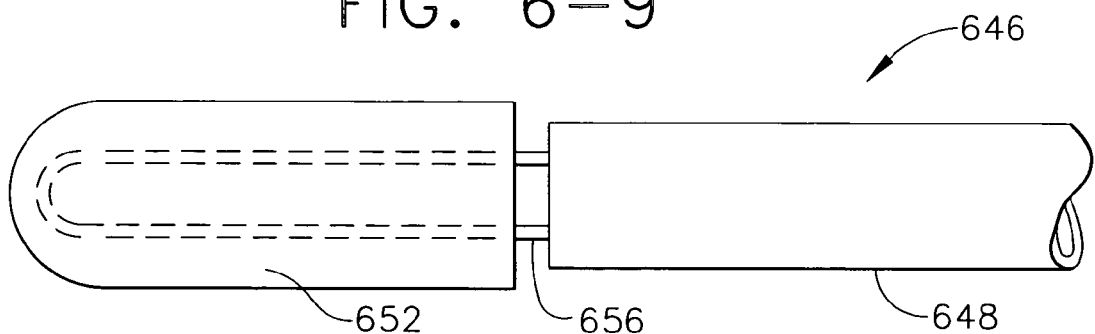
Figures 6, 7, 8, 9, 10, 11:
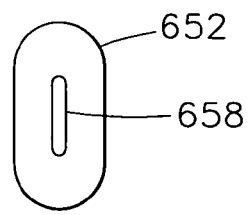
Figures 6, 7, 8, 9, 10, 11, 12:
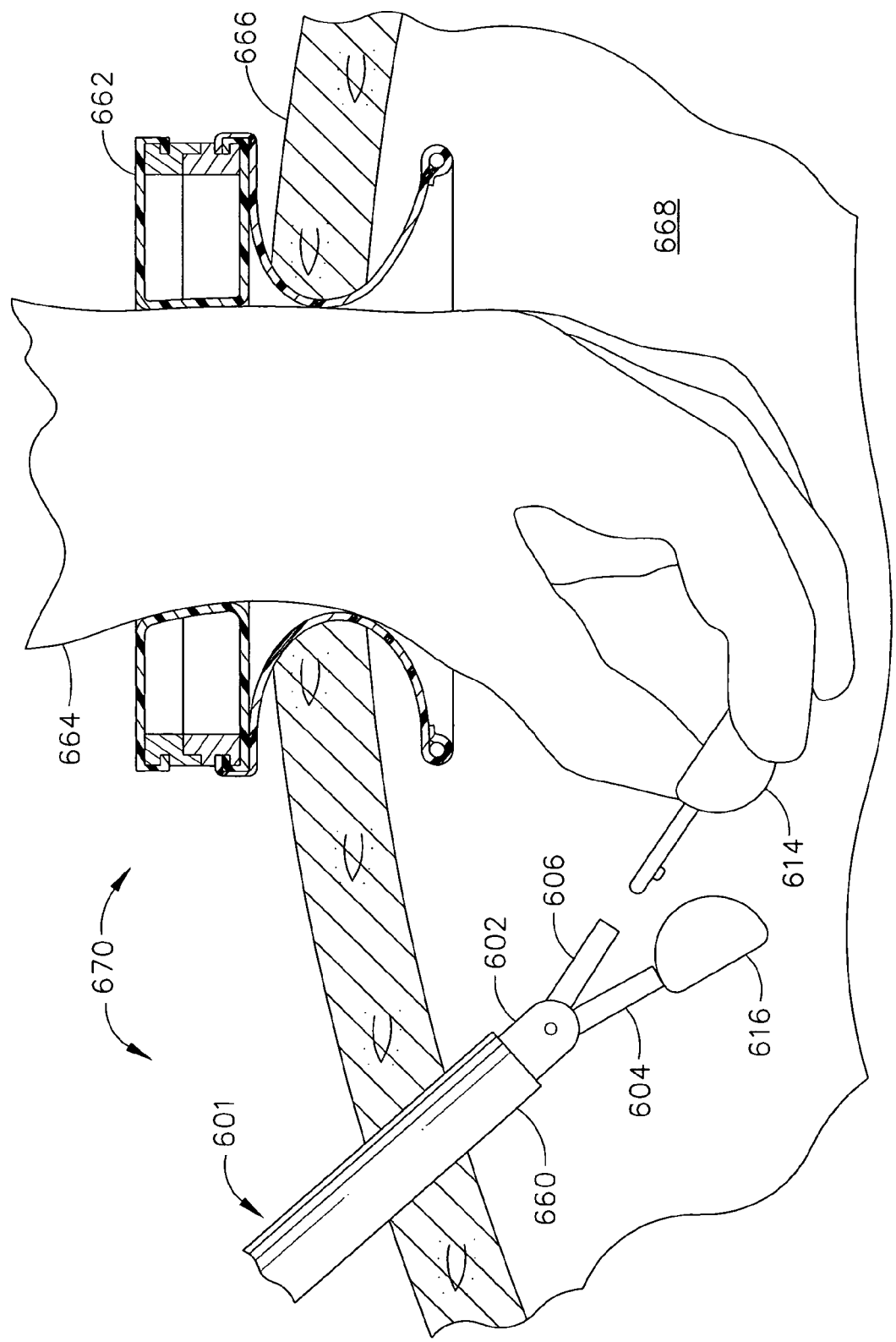
Figures 6, 7, 8, 9, 10, 11, 12, 13:
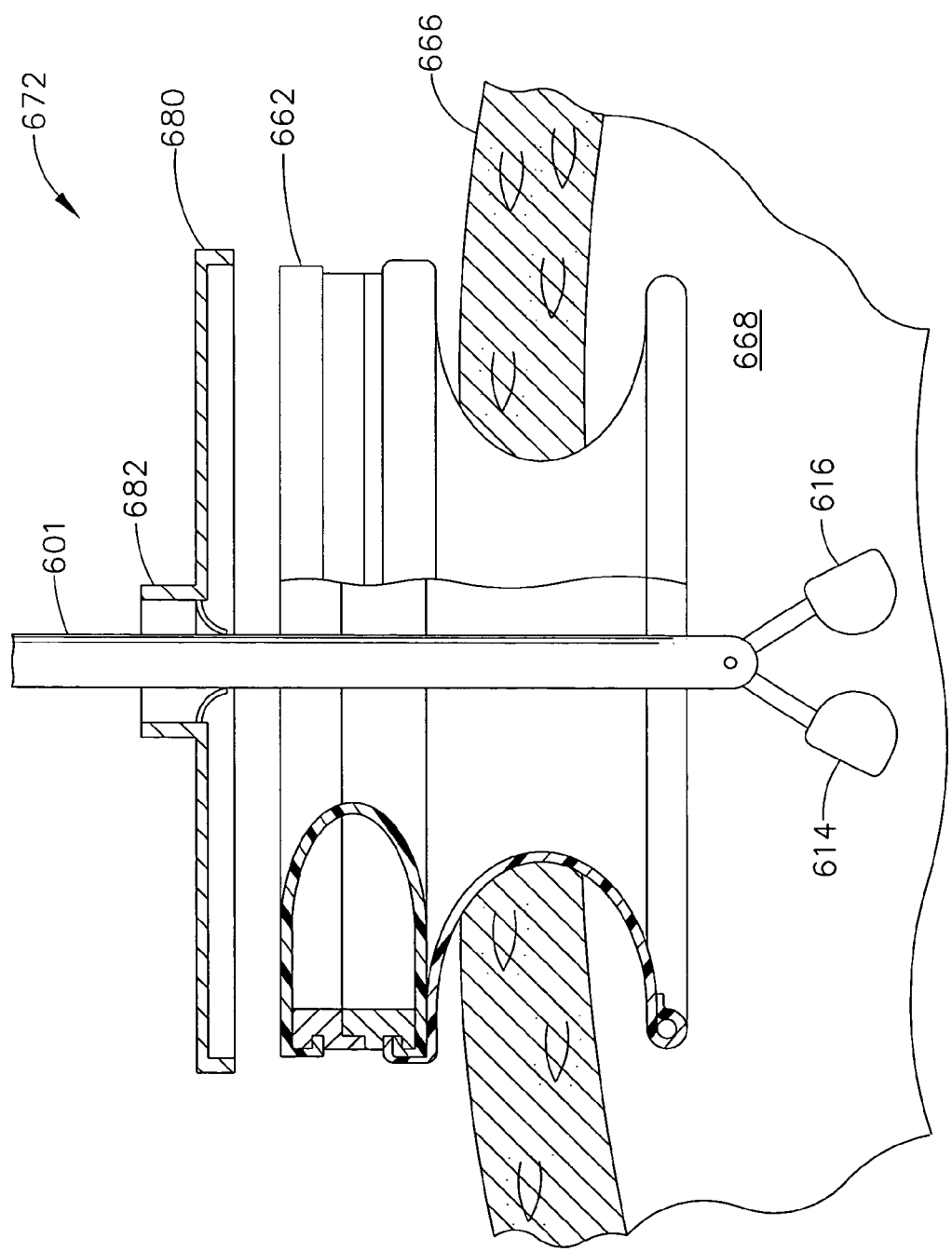
Figures 1, 7:
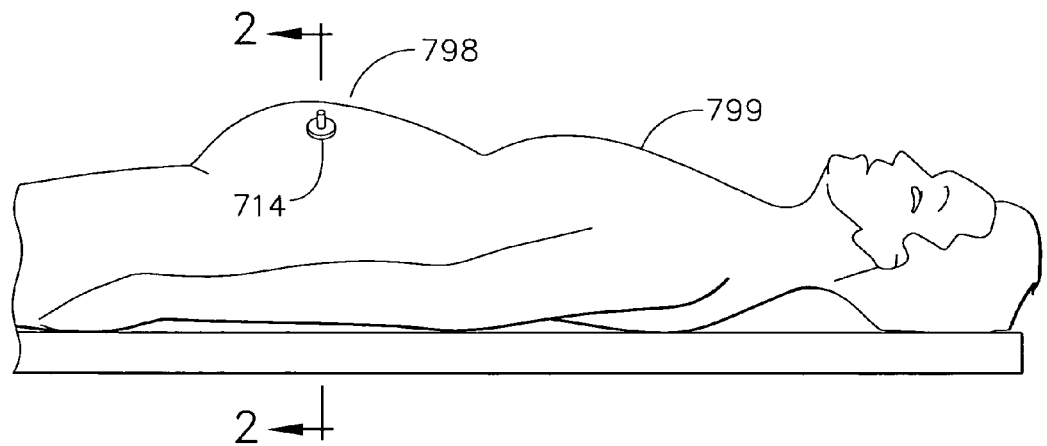
Figures 2, 7:
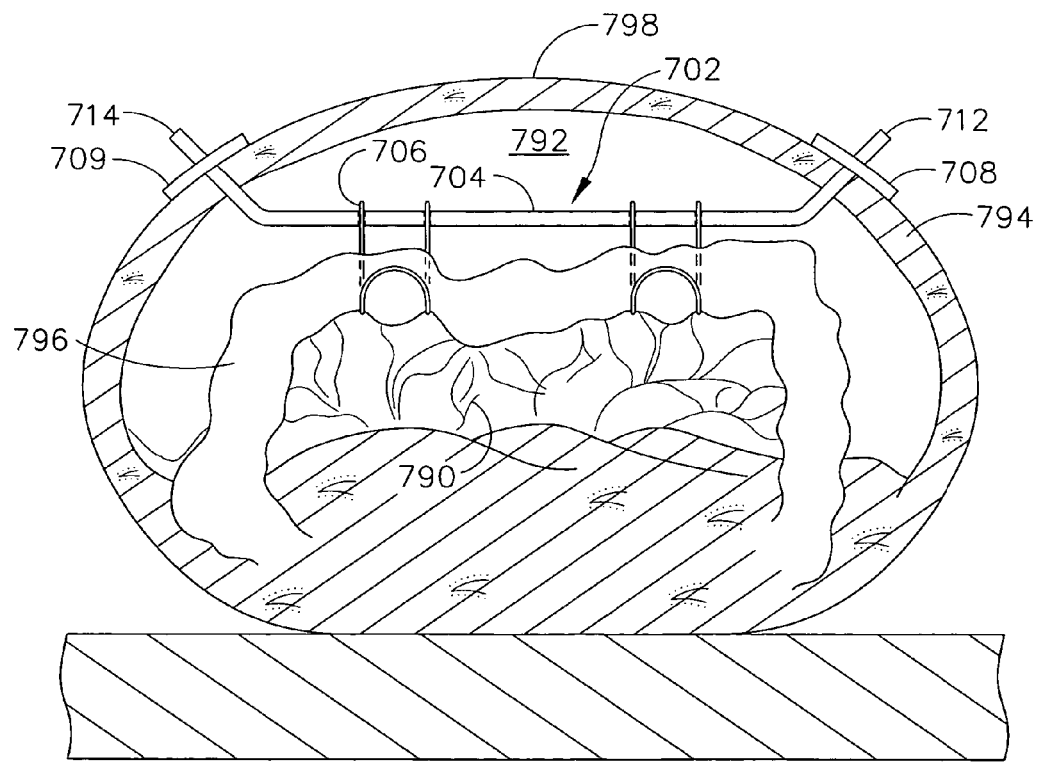
Figures 6B, 7:
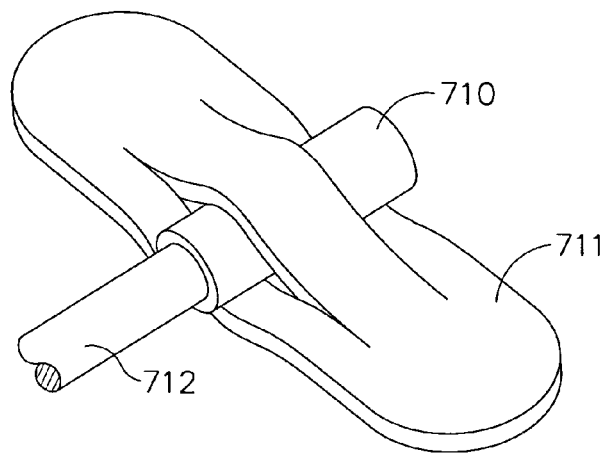
Figure 7:
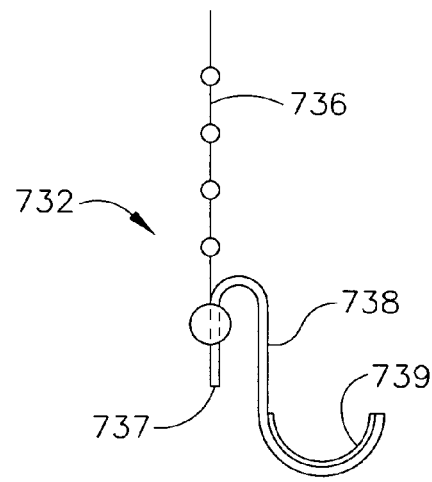
Figures 7, 8:
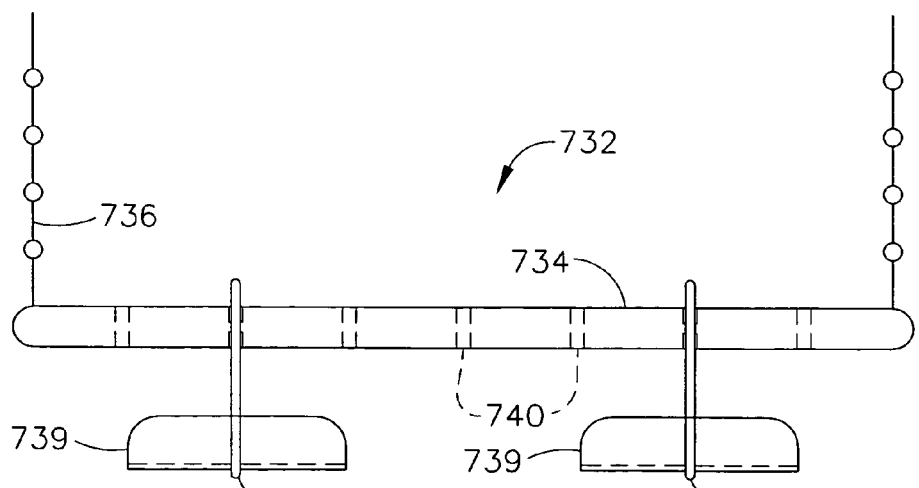
Figures 7, 8, 9:
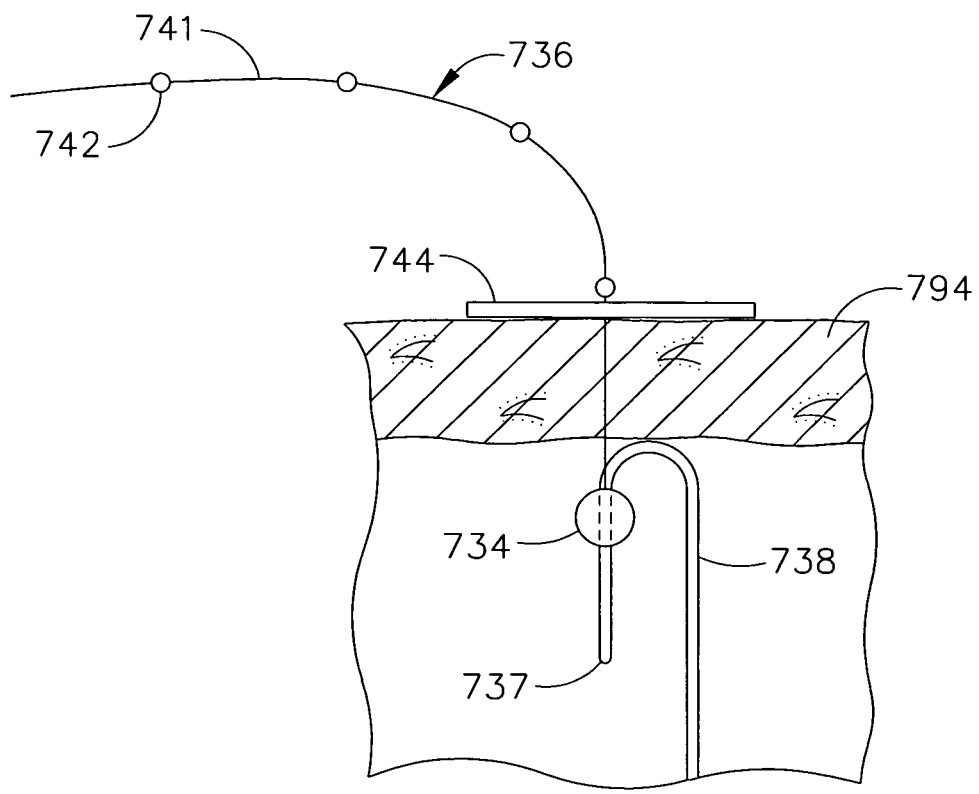
Figures 7, 8, 9, 10:
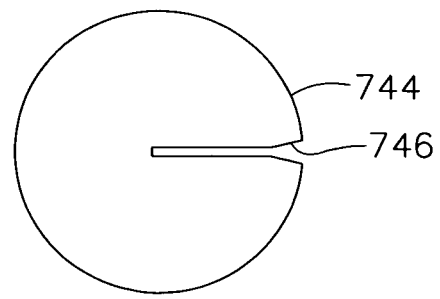
Figures 7, 8, 9, 10, 11:
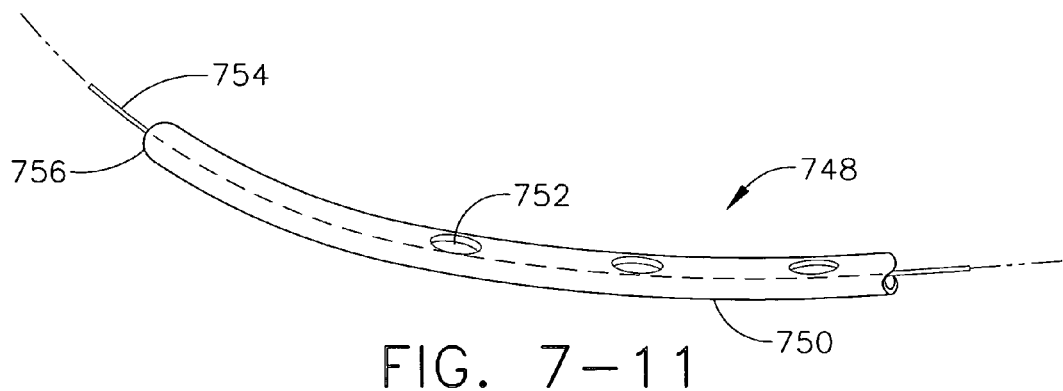
Figures 7, 8, 9, 10, 11, 12:
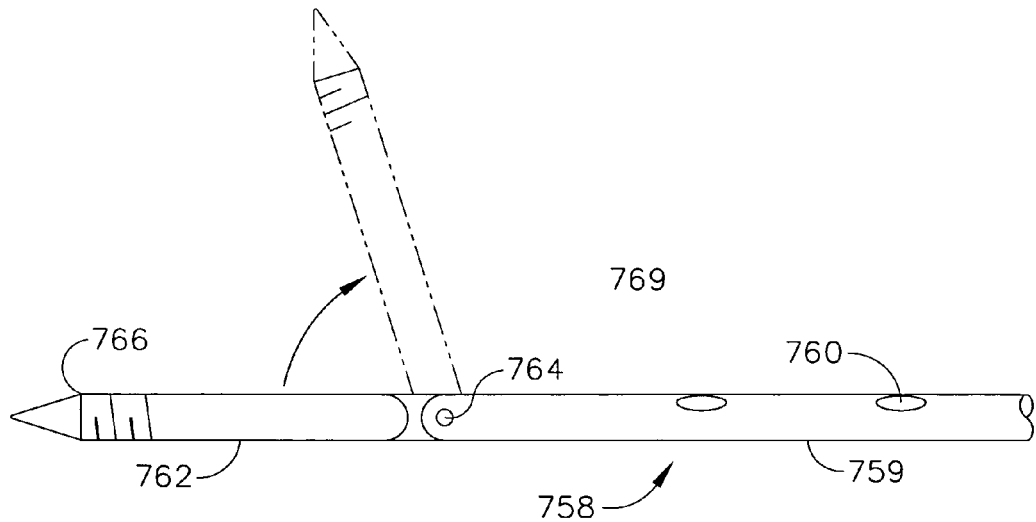
Figures 7, 8, 9, 10, 11, 12, 13:
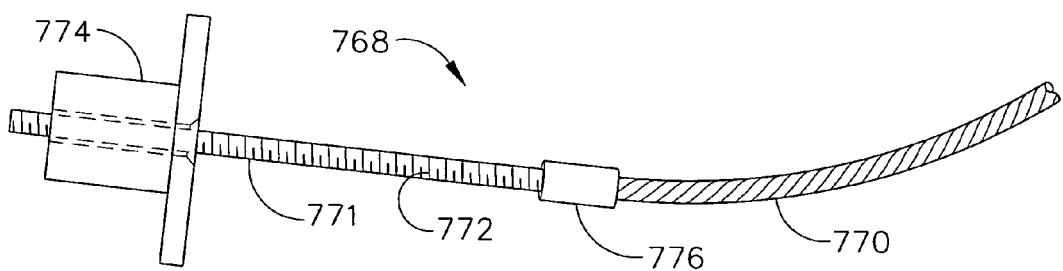

FIG. 5-49 is a front view of the retraction device shown in FIG. 5-48;

FIG. 5-50 is a top view of a thirtieth aspect of a retraction device;

FIG. 5-51 is a front view of the retraction device shown in FIG. 5-50, while in a closed configuration;

FIG. 5-52 is a front view of the retraction device shown in FIG. 5-50, while in an opened configuration;

FIG. 5-53 is a front view of a thirty-first aspect of a retraction device;

FIG. 5-54 is a top view of the retraction device shown in FIG. 5-53, when opened;

FIG. 5-55 is a top view of the retraction device shown in FIG. 5-53, when folded;

FIG. 5-56 is a front view of a thirty-second aspect of a retraction device;

FIG. 5-57 is an end view of the retraction device shown in FIG. 5-56;

FIG. 6-1 is a front view of the distal portion of a surgical instrument, shown with a first aspect of an end effector;

FIG. 6-2 is a sectional view, taken at line 2-2 of FIG. 1, of a first embodiment of an arm of the surgical instrument;

FIG. 6-3 is a front sectional view of the first embodiment of the arm of the surgical instrument shown in FIG. 6-1;

FIG. 6-4 is a front sectional view of a second embodiment of an arm of a surgical instrument;

FIG. 6-5 is an end view of a second aspect of an end effector;

FIG. 6-6 is a front view of the end effector shown in FIG. 6-5;

FIG. 6-7 is an end view of a third aspect of an end effector;

FIG. 6-8 is a front view of the end effector shown in FIG. 6-7;

FIG. 6-9 is a front view of the distal portion of a surgical instrument, shown with a fourth aspect of an end effector;

FIG. 6-10 is a top view of the end effector shown in FIG. 6-9;

FIG. 6-11 is an end view of the end effector shown in FIG. 6-9;

FIG. 6-12 illustrates part of a first method for performing a hand-assisted, laparoscopic procedure;

FIG. 6-13 illustrates part of a second method for performing a hand-assisted, laparoscopic procedure;

FIG. 7-1 is a side view of a patient;

FIG. 7-2 is a cross-sectional view of a patient's abdomen, taken at line 2-2 of FIG. 7-1;

FIG. 7-3 is an end view of a first aspect of a tissue suspension device;

FIG. 7-4 is a side view of the tissue suspension device shown in FIG. 7-3;

FIG. 7-5 is an enlarged side view of a second end of the tissue suspension device shown in FIG. 7-3;

FIG. 7-6A is an enlarged side view of a first end of the tissue suspension device shown in FIG. 7-3;

FIG. 7-6B is an isometric view of the first end of the tissue suspension device shown in FIG. 7-3, assembled to a supporting element;

FIG. 7-7 is an end view of a second aspect of a tissue suspension device;

FIG. 7-8 is a side view of the tissue suspension device shown in FIG. 7-7;

FIG. 7-9 is an enlarged view of a support element on the end of the tissue suspension device shown in FIG. 7-7;

FIG. 7-10 is top view of a retaining element of the support element shown in FIG. 7-9;

FIG. 7-11 is a partial side view of a third aspect of a tissue suspension device;

FIG. 7-12 is a partial side view of a fourth aspect of a tissue suspension device; and FIG. 7-13 is a partial side view of a fifth aspect of a tissue suspension device.

DETAILED DESCRIPTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. Further, unless otherwise indicated, the terms and expressions employed herein have been chosen for the purpose of describing the illustrative embodiments of the present invention for the convenience of the reader and are not for the purpose of limiting the invention.

Further, it is understood that any one or more of the following-described embodiments, expressions of embodiments, examples, etc. can be combined with any one or more of the other following-described embodiments, expressions of embodiments, examples, etc.

Multi-port Insert

A first aspect of a multi-port insert, generally designated 100, relates to an insert for use with a laparoscopic access device 122. Referring now to the figures, FIG. 1-1 and FIG. 1-2 depict one embodiment of the multi-port insert 100. The multi-port insert 100 includes a base 102 having two or more ports or apertures 104 that provide for the insertion of surgical instruments. The multi-port insert 100 may be used with a laparoscopic access device 122 (FIG. 1-7) such as a Lap Disc Hand Access Device model #LD111, commercially available from Ethicon Endo-Surgery, Inc. of Cincinnati, Ohio. The multi-port insert provides for the insertion of one or more surgical instruments through the laparoscopic access device 122, while preventing insufflation gases from escaping from the body cavity.

As illustrated in FIG. 1-1 and FIG. 1-2, the base 102 may include four separate apertures 104 spaced evenly around the center of the base 102 with each aperture 104 having a raised lip or rim 106. This configuration allows surgical tools, such as gripping devices to be inserted through two apertures 104. The gripping devices may be used to manipulate or lift a portion of the bowel to provide the surgeon with access to the either the bowel tissue being manipulated or the underlying tissue. An endoscope including a camera and light may be inserted through a third aperture 104 to provide the surgeon with the ability to view the interior of the body cavity. An additional surgical instrument, such as a needle, scissors, an ultrasonic transducer or any other surgical instrument, may be inserted through the fourth aperture 104. Although FIG. 1-1 and FIG. 1-2 illustrate a base 102 including four apertures 104, alternate numbers and configurations of apertures may be used. In addition, a base 102 may include apertures 104 of varying sizes able to provide for the insertion of differently sized surgical instruments. In one embodiment the apertures may be sized to provide for instruments between five and twelve millimeters in diameter. The base 102 may also include an reference indicator 180 that may be used by the surgeon as a reference point during laparoscopic procedures.

Referring now to FIG. 1-3 and FIG. 1-4, each port or aperture 104 in the base 102 includes its own seal assembly 108 to provide a seal and prevent the escape of insufflation gases. There are many possible types of seals which may be utilized in the seal assembly 108. In one embodiment, each seal assembly 108 includes an iris seal 110 and a duck bill valve 112 such as the seal assembly described in U.S. Patent Application Publication No. 2004/0230161 (Ser. No. 10/815, 356; filed Mar. 31, 2004) to Zeiner, the entire contents of which are hereby incorporated herein by reference. Each iris seal 110 may include a plurality of layered elastic members 114 having a semi-circular profile disposed between two rigid seal rings 116. The elastic members 114 may form a conical-shaped seal such that when a surgical instrument is inserted from the top side thereof, the elastic members 114 are displaced downwardly and radially outwardly and form a seal around the surgical instrument. Each seal assembly 108 may also include a zero-closure valve such as a duckbill valve 112 to prevent the seal assembly 108 from leaking when there is no surgical instrument inserted through the seal assembly 108. The duckbill valve 112 may include two overlapping flaps 113. Pressure from below the duckbill valve 112 pushes the flaps 113 together, maintaining the seal. Pressure from above the duckbill valve 112 pushes the flaps 113 apart, allowing a surgical instrument to pass through.

In one embodiment, each seal assembly 108 is flexibly attached to the base 102 using a floatation system such as bellows 118 located around the periphery of each seal assembly 108. The bellows 118 may be made from a flexible, elastic material and allow the seal assembly 108 to move laterally and pivot within the aperture 104. The movement of the seal assembly 108 allows surgical instruments to be inserted through the apertures 104 at an angle rather than along the axis of the aperture 104. The bellows 118 may be attached to the lip of the aperture 104 by a retaining ring 120 that frictionally fits over each rim 106. The force required to deflect the bellows 118 is much less than the pressure exerted by surgical instrument on the elastic members 114 while the surgical instrument is inserted in the seal assembly 108. This allows the floatation system to deflect within each aperture 104 while the elastic members 114 maintain a sealing condition with the instrument.

The multi-port insert 100 may be attached to a laparoscopic access device 122 as shown in FIG. 1-7. The laparoscopic access device 122 may include a generally coaxially aligned upper ring 146 and lower ring 148 and a membrane 128 coupled to and extending generally axially between the upper ring 146 and lower ring 148. The membrane 128 has a central opening of variable size. For example, in one embodiment the upper ring 146 and lower ring 148 are rotatable in opposite directions relative to one another to change the size of the opening. The base 102 of the multi-port insert 100 may be attached to the laparoscopic access device 122 by a simple latch mechanism 124 to allow the multi-port insert 100 to be attached to currently available laparoscopic access devices 122. Alternatively, one or more C-clamps or other clamping devices or structures may be used to attach the multi-port insert 100 to a laparoscopic access device 122. In addition, the multi-port insert 100 may be attached to a laparoscopic access device 122 using a threadable surface on the multi-port insert 100 and a corresponding mating threadable surface on the laparoscopic access device 122.

Once attached to the laparoscopic device, the base 102 of the multi-port insert 100 may form a seal with the laparoscopic access device 122 to prevent the escape of insufflation gas. As shown in FIG. 1-5, the base 102 may include a collar 126 that may be inserted into the laparoscopic access device 122. As illustrated in FIG. 1-7, the collar 126 extends into the laparoscopic access device 122 and forms a seal with the membrane. In addition, the collar 126 may also protect the membrane 128 of the laparoscopic access device from any surgical instruments inserted through the apertures 104. As depicted in FIG. 1-5, the collar 126 may include a generally tapered portion 127. The tapered portion 127 allows the apertures 104 to be seated within the laparoscopic access device 122. Lowering the apertures 104 lowers the pivot points of the surgical instruments and increases the range of motion of the surgical instruments inserted through the apertures 104. In an alternate embodiment, the collar 126 does not include a tapered portion and may be generally cylindrically shaped.

In an alternate embodiment illustrated in FIG. 1-6, a resilient layer 150 may be located on a lower surface of the base 102 such that when the multi-port insert 100 is attached to the laparoscopic access device 122, the resilient layer 150 forms a seal between the multi-port insert 100 and the laparoscopic device. The resilient layer 150 may be formed from a closed-cell elastomer or any other suitable material.

In another embodiment, the base 102 of the multi-port insert may be inserted through the opening in the membrane 128 of the laparoscopic access device 122 and attached to the lower ring 148 of the laparoscopic access device 122. This configuration would provide a greater range of motion within the body cavity for the surgical instruments by lowering the pivot points for the instruments below the surface of the skin.

The multi-port insert 100 may also include one or more instrument supports 130 that are attached to the base 102 to fix the position of one or more surgical instruments inserted through the multi-port insert 100. FIG. 1-8 illustrates a first embodiment of a surgical instrument support 130 extending generally axially from the base 102. The surgical instrument support 130 may include a gripping portion 138, a stem 154 and an instrument support base 134. The gripping portion 138 may be used to hold one or more surgical instruments and may include a C-clamp or any other device suitable for holding a surgical instrument. The stem 154 connects the gripping portion 138 and the instrument support base 134. In one embodiment, the stem 154 may be composed of a malleable substance, such as copper wire, to allow the surgical instrument support 130 to be positioned to hold a surgical instrument.

The instrument support base 134 attaches the instrument support 130 to the multi-port insert 100. The base 134 may be inserted into a track 132 that extends around the periphery of the multi-port insert 100. The track 132 may include an opening 178 to allow an instrument support base 134 to be inserted into the track 132. The instrument support 130 may be positioned along the track 132 around the circumference of the multi-port insert 100.

The instrument support 130 includes a positional lock 136 for fixing the position of the instrument support base 134 with respect to the multi-port insert 100. The stem 154 may be inserted through an aperture in the positional lock 136. The positional lock 136 may be threadably connected to the instrument support base 134, such that when the positional lock 136 is rotated in a first direction the instrument support base 134 is drawn upward away from the base 102. Frictional forces between the track 132, the instrument support base 134 and the positional lock 136 secure the instrument support base 134 relative to the base 102 of the multi-port insert 100. In an alternative embodiment, a clamp may be used to secure the instrument support 130 to the base 102.

The instrument support 130 may also include an extension control 152 and an extension lock 140. The extension control 152 includes a generally conical portion 166 and an aperture shaped to receive the stem 154. The conical portion 166 of the extension control 152 includes one or more slits (not shown). The extension lock 140 includes an aperture shaped to receive the stem 154 and a generally conical shaped opening 156. The extension lock 140 may be threadably connected to the extension control 152 such that the extension lock 140 may be drawn downward over the extension control 152. The pressure exerted by the extension lock 140 on the extension control 152 pushes the conical portion 166 of the extension control 152 down and inward, exerting pressure against the stem 154, preventing the stem 154 from sliding through the apertures in the extension control 152 and thereby locking the stem 154 in place. The surface of the stem 154 may be rough, textured or covered with a coating to increase friction between the stem and the extension control 152 and facilitate locking the stem 154 in place.

FIG. 1-10 illustrates an alternate embodiment of an instrument support 130' in which the instrument support 130' covers and is radially aligned with an aperture 104 of the multi-port insert 100. The instrument support 130' may be attached to one or more of the apertures 104. One or more of the rims 106 may be shaped to form a socket-shaped housing 142'. The instrument support 130' includes an instrument support base 134' having a semispherical portion seated within the housing 142'. The instrument support base 134' is capable of pivoting within the housing 142' to provide a range of motion to the surgical instruments received therethrough. The instrument support 130' may include a rotation lock 164' threadably connected to the instrument support base 134'. Rotating the rotation lock 164' in a first direction causes the rotation lock 164' to exert pressure downward on the housing 142' while at the same time drawing the instrument support base 134' upward against the housing 142'. The frictional forces between the instrument support base 134', the housing 142' and the rotational lock 164' may prevent the instrument support base 134' from pivoting or rotating within the housing 142'.

The instrument support 130' may include an instrument contact ring 160' and an instrument locknut 162' designed to control the depth of insertion into the body cavity of the surgical instruments. The instrument locknut 162' may be threadably connected to the instrument support base 134' such that, when the locknut 162' is rotated and engages the threads of the instrument support base 134', the locknut 162' exerts pressure against the instrument contact ring 160' causing the contact ring 160' to close around the surgical instrument and thereby controlling the depth of insertion of the instrument.

FIG. 1-11 illustrates a third embodiment of an instrument support 130". This embodiment also covers and is radially aligned with an aperture 104 of the multi-port insert 100. The instrument support 130" may include a socket-shaped, metalized or metal impregnated housing 142" that attaches to the upper surface of the base. The instrument support 130" includes an instrument support base 134" having a semispherical portion which rests upon the housing 142". The instrument support base 134" is capable of pivoting on the housing 142" to provide a range of motion to the surgical instruments received therethrough. The instrument support 130" may include includes one or more magnets 170" attached to the instrument support base 134". The attraction between the housing 142" and the magnets 170" holds the instrument support base 134" in place relative to the housing 142". The instrument support 130" includes an elastic boot 168" attached to the housing 142" and the instrument support base 134". The elastic boot 168" maintains a seal and prevents the escape of insufflation gases. As in the previous embodiment, the instrument support 130" may include seal assembly 108, an instrument contact ring 160 and an instrument locknut 162 to control the depth of insertion of a surgical instrument. The seal assembly 108 may include a duckbill valve 112 and an iris seal 110.

FIG. 1-12 illustrates a further embodiment of the instrument support 130''' in which the housing 142''' may include a set of concentric ridges 172'''. The instrument support base 134''' may include one or more legs 174''' include a set of teeth 176''' that mate with the ridges 172''' of the housing 142''' to hold the instrument support base 134''' in place relative to the housing 142'''. In this embodiment, the elastic boot 168''' attaches holds the instrument support base 134''' in contact with the housing 142'''.

The multi-port insert may be utilized during laparoscopic procedures to provide the surgeon with the ability to insert multiple surgical instruments into the body cavity of the patient without substantial loss of insufflation gases and without requiring multiple additional incisions. In one embodiment the lower ring of the laparoscopic access device 122 may be inserted into the body of a patient through an incision in the abdomen of the patient. During laparoscopic surgery, the surgeon may elect to attach a multi-port insert 100 to the upper ring 148 of the laparoscopic access device 122 using the latch mechanisms 124, clamps or the like. Once attached, the multi-port insert 100 forms a seal with the laparoscopic access device 122. The seal between the multi-port insert 100 and the laparoscopic access device 122 and the seal assemblies 108 prevent excessive amounts of the insufflation gases from escaping the body cavity. The surgeon may insert a surgical instrument through any or all of the apertures 104. This allows the surgeon to insert multiple surgical instruments into the body cavity patient at the same time. The seal assemblies 108 automatically reseal upon removal of the surgical instruments allowing the surgeon to insert and remove multiple surgical instruments during surgery.

The multi-port insert 100 may also include one or more instrument supports 130 designed to hold surgical instruments inserted through the multi-port insert. In one embodiment the instrument supports 130 attach to the track 132 in the base 102. The instrument supports 130 may be positioned at an appropriate location on the base 102 and locked into place using the positional lock 136. The surgeon may control the distance the instrument support 130 extends from the base 102 using the extension control 152 and extension lock 140. The instrument support 130 may be attached to a surgical instrument using the gripping portion 138. The surgeon may reposition and readjust the instrument support 130 at any time. At any time during the procedure the surgeon may elect to disconnect the multi-port insert 100 from the laparoscopic access device 122.

Surgical Access Device

FIG. 2-1 is a partially sectioned front view of an access device 202 of the prior art, positioned in a body wall 299 of a patient. Access device 202 is disclosed in U.S. Pat. No. 6,110,154, which issued to Shimomura et al. on Aug. 29, 2000, and is titled "Valve and Valved Trocar Jacket Tube." Access device 202 includes an upper ring 204, a lower ring 206, a first cylindrical elastic member 208 (or first elastic member 208), a second cylindrical elastic member 210 (also referred to as second elastic member 210 and sleeve 210), and a resilient member 212. First elastic member 208 and second elastic member 210 are each made of a thin-walled, silicone rubber tubing material, or any one of a number of other elastic, biocompatible materials in sheet or tube form. The ends of first elastic member 208 are assembled with upper ring 204 and lower ring 206, respectively, to form a hyperboloid ("hour glass") shape defining an opening 250 centered on a vertical axis 249 of access device 202. Similarly, the ends of second elastic member 210 are assembled with lower ring 206 and resilient ring 212 to form a hyperboloid shape and defining a passageway 223 therethrough. The surgeon may position second elastic member 210 in the body wall 299 of the patient by pushing resilient ring 212 (while folded) through the surgical incision. Once in the body cavity, resilient ring 212 resumes an approximately circular shape to sealingly retain access device 202 in body wall 299. An annular interface 211 between upper ring 204 and lower ring 206 frictionally holds the relative angular orientation of upper ring 204 and lower ring 206 in order to maintain the size of opening 250. The frictional holding force is easily overcome by the surgeon turning either one of upper ring 204 and lower ring 206 while holding the other. Additionally, upper ring 204 and lower ring 206 may each be molded from a plastic to have interlocking features around the perimeter of their mating surfaces. The surgeon may accordingly adjust the relative angular position about vertical axis 249 of upper ring 204 with respect to lower ring 206, and thus set the size of opening 250 to numerous diameters ranging from a fully closed configuration to a fully open configuration. The surgeon may adjust opening 250, therefore, to seal against the surgeon's hand or one or more surgical instruments extending through opening 250, providing the ability to insufflate the body cavity with carbon dioxide during the surgical procedure.

Upper ring 204, lower ring 206 and first elastic member 208 are also referred to together as a valve subassembly 201. As will become apparent to those skilled in the art, the aspects and features described herein are also applicable to surgical access devices having other types of valve assemblies such as, for example, those including a hydrophilic gel material with a sealable slit opening for surgical access into the body cavity.

FIG. 2-2 is a front view and FIG. 2-3 is a top view, of a first aspect of an access device 222 while in a closed configuration. Access device 222 includes a tubular access channel 238 extending from a lower ring 226 to a resilient ring 232. The surgeon may position a second elastic member 230 in the surgical incision and adjust an upper ring 224 with respect to lower ring 226 to set the size of opening 250 in a first elastic member 228 as described for access device 202 of FIG. 2-1. Access channel 238 increases the overall functionality of access device 202. The surgeon may use access channel 238 to introduce ancillary, remotely operable, surgical implements and/or accessories into the body cavity of the patient, separate from and without obstructing opening 250 and passageway 223. Access channel 238 may be made of, but is not limited to, any one of numerous flexible, biocompatible materials including polyvinyl chloride, polyethylene, silicone rubber, and polyurethane extruded tubing. A proximal end 246 of access channel 238 attaches to a port 236 having a cap 242. Port 246 attaches to a tab 234 extending radially from lower ring 226. Port 246, tab 234, and lower ring 226 may be injection molded unitarily. The surgeon may introduce a surgical implement into port 246 along a may be approximately in the range of, but is not limited to, 0-90 degrees. Access channel 238 has a distal end 244 attached to resilient member 232 with a clip 240. Clip 240 may be, for example, made of a resilient material, such as silicone rubber, and adhered to second elastic member 230 around resilient member 232. Access channel 238 may also be adhered to the outside or inside of second elastic member 230, or molded integrally into the wall of second elastic member 230. Distal end 244 may extend a short distance, such as 0-5 centimeters, distal to resilient member 232, and is oriented in a generally downward direction as shown. Access channel 238 has sufficient length to conform to the outside shape of second elastic member 230 so that the body wall of the patient may easily seal around both access channel 238 and second elastic member 230.

Port 236 may alternately be attached to upper ring 224, rather then to lower ring 226. If port 236 is attached to upper ring 224, than access channel 238 would need to be long enough to wrap around second elastic element 230, spiraling around second elastic element 230 at least one wrap, so that the surgeon may rotate upper ring 224 in either direction to adjust the size of opening 250.

FIG. 2-4 is an enlarged, sectional view of port 236 of access device 222 shown in FIG. 2-2 and FIG. 2-3. Proximal end 246 of access channel 238 assembles into port 236, for example, with a biocompatible adhesive. Port 236 retains a seal 237, which is made of a silicone rubber, for example. Seal 237 has a disc shape and contains a small, central hole that may easily stretch and seal around a surgical implement and/or accessory introduced into port 236. To maintain insufflation in the body cavity when the surgeon is not using access channel 238, the surgeon may press cap 242 onto port 236. Port 236 of FIG. 2-4 is shown as merely one example; many other versions of a sealable port assembly will become apparent to those skilled in the art, such as those versions incorporating a duckbill valve, a gel, or a closed-cell foam material. The size, shape, orientation, and sealing method of port 236 may be adapted to one or more particular surgical implements and/or accessories to be used in the surgical procedure.

FIG. 2-5 is a front view and FIG. 2-6 is a top view, of a second aspect of an access device 252 while in an open configuration. Access device 252 includes a first access channel 268 having a first port 266, a second access channel 272 having a second port 270, a third access channel 276 having a third port 274, and a fourth access channel (not visible) having a fourth port 278. Each of the ports is attached to or unitarily formed with a lower ring 256 by one of four tabs 264. Each of the access channels pass through one of four entrance holes 253 near the proximal end of a second elastic member 230, extend between an inner wall 259 and an outer wall 257 of second elastic member 260, and pass through one of four exit holes 255 near the distal end of second elastic member 230. The surgeon may position second elastic member 230 in the surgical incision and adjust upper ring 254 with respect to lower ring 256 to set the size of opening 250 in a first elastic member 258 as described for access device 202 of FIG. 2-1.

FIG. 2-7 is an isometric view of a third aspect of an access device 282, shown schematically in combination with eight ancillary devices and/or systems typically used in a surgical procedure. Access device 282 has eight access channels that are separate from and do not obstruct opening 250 and passageway 223. Access device 282 includes an upper flange 283 that extends from a lower ring 286. Eight inlet ports ((291, 292, 293, 294, 295, 296, 297, and 298) are shown spaced apart evenly on upper flange 283 (although they may be spaced apart unevenly). Each inlet port has a corresponding outlet port (291', 292', 293', 294', 295', 296, 297, and 298') attached to a flexible, lower flange attached to a second elastic element 290. As for the second aspect of access device 252 described in FIG. 2-5, each access channel is retained between inner and outer walls of second elastic element 290.

In FIG. 2-7, access device 282 is shown, by way of example, with a variety of ancillary, surgical devices and systems. Other surgical implements, accessories, systems, and devices will become apparent to those skilled in the art. Some of these devices may be small enough to pass through the access channel. Other devices may first need to be introduced into the body cavity via opening 250, and then operably connected to the corresponding outlet port. In some instances, the inlet port or outlet port may include a short pigtail connection.

In FIG. 2-7, a light source 229 operably connects to an outlet port 298' via a fiber optic bundle introduced into inlet port 298, to illuminate the body cavity. An ultrasonic generator 227 operably connects to outlet port 291' via a cable introduced into inlet port 291. An ultrasonic device (not shown) may be introduced into the body cavity via opening 250, and then operably connected to outlet port 291'. An electrical power source 225 electrically connects to outlet port 292' (hidden) via an electrical conductor introduced into inlet port 292. Electrical power may be used, for example, for lighting inside the body cavity, or for powering a tissue-morcelating device (not shown). A flexible, mechanical instrument 231, such as a surgical grasper, is introduced into inlet port 297. A drug/dye administering device 233 is shown, for direct injection into the body cavity via inlet port 293 to treat or mark tissues and organs. A vacuum source 235 fluidly connects with outlet port 294' (hidden) via a tube introduced into inlet port 294, for the suction of fluids out of the body cavity. A fluid source 241 fluidly connects with outlet port 296' via a tube introduced into inlet port 296, for irrigation of tissue in the body cavity. An electrosurgical generator 239 electrically connects to outlet port 295' via an electrical conductor introduced into inlet port 295. An RF instrument (not shown) may be electrically connected to outlet port 295' to be used by the surgeon to cauterize tissue in the body cavity.

Each access channel described in FIG. 2-7 may include either a single or a multilumen, extruded tube. For example, a double lumen access channel may provide both suction and irrigation functions, or electrically isolate a pair of electrical conductors.

FIG. 2-8, FIG. 2-9, and FIG. 2-10 illustrate partial views of a fourth aspect of an access device 203, which provides the surgeon with the ability to conveniently and quickly change access device 203 from a closed or partially closed configuration to an open configuration. Access device 203 includes an intermediate ring 209 disposed between an upper ring 205 and a lower ring 207. A locking element 215 attaches to an outer circumferential surface 218 (FIG. 2-8) of upper ring 205, and releasably locks upper ring 205 to intermediate ring 209. Intermediate ring 209 has a plurality of undercut, upper teeth 213 spaced apart on the perimeter of intermediate ring 209. Upper teeth 213 may interlock with a like plurality of undercut, lower teeth 214 spaced apart on the perimeter of lower ring 207. When a surgeon rotates either of upper ring 205 and lower ring 207 relative to the other in a first rotational direction, upper teeth 213 and lower teeth 214 engage to prevent relative movement of upper ring 205 and lower ring 207 in an opposite, second rotational direction, which is promoted by the spring-back force from twisting first elastic member 208 as opening 250 closes. To release upper ring 205 from lower ring 207, the surgeon may, for example, slightly turn upper ring 205 in the first rotational direction while holding lower ring 207, and pull upper ring 205 apart from lower ring 207 to disengage the upper teeth 213 from the lower teeth 214.

Locking element 215 allows the surgeon to quickly release upper ring 205 from lower ring 207, so that access device 203 may instantly spring back from a closed configuration to an open configuration. Locking element 215 is attached at a fulcrum 219 (FIG. 2-9) on surface 218 of upper ring 205. A pawl 217 of locking element 215 engages a recess 216 in intermediate ring 209 (FIG. 2-9) to lock upper ring 205 to intermediate ring 209, which, in turn, locks to lower ring 207 via the engagement of upper teeth 213 to lower teeth 214. The surgeon may press a pad 220 of locking element 215 to unlock upper ring 205 from intermediate ring 209. The spring back force caused by the twisting of first elastic member 208 while closing opening 250 allows access device 203 to immediately change to the open configuration. When the surgeon changes access device 203 from the open to the closed configuration, the relative rotation of upper ring 205 and lower ring 207 allows pawl 217 to automatically engage with recess 217. Further rotation then allows upper teeth 213 and lower teeth 214 to engage in order to maintain the size of opening 250. This type of locking mechanism is incorporated into the "Lap Disc Hand Access Device," which is available from Ethicon Endo-Surgery, Inc., Cincinnati, Ohio.

Those skilled in the art will appreciate that numerous other aspects of an access device are possible for providing a way to quickly change access device from a closed or partially closed configuration to an open configuration, and that access device 203 is provided as only one example. Access device 203 may also incorporate at least one access channel as described for, but not limited to, the other aspects of the access device described herein.

Tissue Markers and Method for Planning a Surgical Procedure

During a surgical procedure such as hand-assisted laparoscopy, the surgeon must identify tissue structures that are highly mobile within the body cavity, that have a similar coloration as surrounding tissues, and that are generally difficult to find under laparoscopic visualization. The surgeon uses laparoscopic tools and his/her hand to move organs and identify key, anatomical structures in order to plan the surgical procedure. For a tissue resection, for example, in which the surgeon cuts and removes internal tissue from the patient, the surgeon generally needs three types of information to plan the procedure: (1) Where are the proximal and distal end points of the resection? (2) Where is the proximal artery supplying blood to the tissue to be resected? and (3) Where should the line of resection be? Obtaining this information may be very time consuming, and so once the surgeon identifies a key, anatomical structure (or "landmark"), the surgeon would like to mark that area of tissue very conspicuously before searching for other key landmarks. Then the surgeon would be able to quickly find the structure again later during the procedure. Using the "zoom" feature on a laparoscope, and switching back and forth between a close-up view of tissue and a view of a wider area of tissue, may also disorient even experienced surgeons. Accordingly, a method for planning a surgical procedure using a tissue marker, and numerous aspects of a tissue marker, are provided.

FIG. 3-1 through FIG. 3-32 show ten different aspects of a tissue marker, which a surgeon may attach to tissue to indicate a key, anatomical structure. Each of the ten aspects of the tissue marker may be applied to tissue using an applier (single or multiple deploying) that is adapted for that particular tissue marker. Other tissue marker and applier aspects or modifications are possible, and may become apparent to those skilled in the art.

Generally, the tissue marker aspects described herein allow fast, easy, and accurate attachment to internal, soft tissue, and are highly visible throughout the surgical procedure. Each tissue marker aspect also provides the surgeon with the ability to label or otherwise signify meaningful information (using color coding, written information, etc.) to the tissue, to help the surgeon to plan the surgical procedure.

Depending on the type of surgical procedure, the tissue marker may also be made of a material to facilitate medical imaging. For example, the tissue marker may be formed from a radio opaque material for X-ray imaging. The tissue marker may be formed from or coated with a fluorescent material to enhance visibility during the procedure. Or the tissue marker may be made of a material that contains a multiplicity of microbubbles for ultrasonic imaging. The tissue marker may also include a doping agent to facilitate magnetic resonance imaging.

The tissue marker may also be made of an absorbable polymer such as "Vicryl" (Ethicon, Inc., Somerville, N.J.), which may be absorbed by the patient's body within a few weeks. Using an absorbable polymer provides the surgeon with the option to leave the tissue marker in the body after the surgical procedure is completed. Of course, the tissue marker may also be applied to a portion of tissue that is removed from the patient.

The tissue marker may also include an antimicrobial or a drug-eluting coating to inhibit the growth of bacteria in tissue surrounding the tissue marker.

FIG. 3-1 is a top view, FIG. 3-2 is a side view (before deployment), and FIG. 3-3 is a side view (after deployment) of a first aspect of a tissue marker 301. FIG. 3-4 is an illustration of tissue marker 301 during attachment to tissue, and FIG. 3-5A is an illustration of tissue marker 301 after attachment to tissue. Tissue marker 301 is a thin disc of metal or rigid plastic, having a central, fluted aperture 302 for entrapping tissue pulled within. An applier 303 (FIG. 3-4) retains tissue marker 301 and supplies a negative pressure to pull soft tissue 399 into aperture 302. Applier 303 may be attached to a length of flexible tubing that is fluidly connected to a controllable vacuum source (not shown). Applier 303 may also include the vacuum source, which may be a hand-operable pump, for example. Tissue marker 301 may further comprise a flag 304 attached to disc 301. Flag 303 may be color coded, preprinted with written matter (for example, "distal"), or contain a writing area on which the surgeon may create a custom label. Flag 304 may be made of any one of a number of biocompatible materials, including a fabric, plastic, elastomer, metal foil, coiled wire, and paper. Flag 304 may also be incorporated into the design of any of the other aspects of the tissue marker shown in FIG. 3-6 through FIG. 3-32.

FIG. 3-5B and FIG. 3-5C show a tissue marker 356 having an exemplary embodiment of a flag 359 that is formed from a flat coil of spirally wound, malleable material having an attached end 357 and a colored, free end 358. The surgeon may attach tissue marker 356 to tissue while it is in a compact configuration, using an applier as described for FIG. 3-5A. The surgeon then may grasp free end 358 with a conventional grasping instrument to extend flag 359, thus making tissue marker 356 more conspicuous.

FIG. 3-6 is a top view, FIG. 3-7 is a side view (before deployment), and FIG. 3-8 is a side sectional view (after deployment) of a second aspect of a tissue marker 305. Tissue marker 305 includes a disc 306 and a receiver 308. A pair of legs 307 extend from the bottom of disc 306, and insert into a pair of ramps 309 in the bottom of receiver 308, so that during deployment, pair of legs 307 come together tip-to-tip to entrap tissue. Receiver 308 retains disc 306 in a one-time assembly. Tissue marker 305 attaches to tissue securely during the surgical procedure, but may be pulled off of the tissue when no longer needed. Tissue marker 305 may be injection molded, for example, from any one of a number of biocompatible polymers.

FIG. 3-9 is a top view, FIG. 3-10 is a sectional side view (after deployment), and FIG. 3-11 is a side view (before deployment) of a third aspect of a tissue marker 310. Tissue marker 310 includes a plunger 311 inserted into a housing 312. A hook 314 is attached to plunger 311 and extends from the bottom of housing 311 when the surgeon squeezes plunger 311 and housing 312 together, much like the way a "fishing bobber" can be attached to a fishing line. A spring 313 biases retraction of hook 314 into housing 312. The surgeon may attach hook 314 into tissue and release plunger 311 to attach tissue marker 305 to the tissue. Plunger 311 and receiver 312 may be made of a biocompatible polymer, and hook 314 may be made of a stainless steel, for example.

FIG. 3-12 is a top view, FIG. 3-13 is a sectional side view (before deployment), and FIG. 3-14 is a side view (after deployment) of a fourth aspect of a tissue marker 315. Tissue marker 315 includes a plunger 316 inserted into a housing 317. A spring hook 318 is attached to plunger 316 and extends through the bottom of housing 317 and engages tissue (like a "cork screw") when a surgeon grips plunger 316, and pushes and rotates tissue marker 315 against the tissue of interest.

FIG. 3-15 is a side view, FIG. 3-16 is an end view, FIG. 3-17 is a front view (before deployment), and FIG. 3-18 is a front view (after deployment) of a fifth aspect of a tissue marker 319. Tissue marker 319 includes a crown 324 from which extend a pair of legs 321, spaced apart by a latch beam 323. A latch 322 extends from the bottom side of crown 324, so that when the surgeon deploys tissue marker 319 into the tissue of interest, latch 322 engages with a hole in beam 323 to hold legs 321 together, thus entrapping tissue and attaching tissue marker 319 to the tissue. A tab 320 extends from crown 320 to provide additional visibility and space for information. Tissue marker 319 may be injection molded from a biocompatible polymer. FIG. 3-19 is an end view, FIG. 3-20 is a front view (before deployment), and FIG. 3-21 is a front view (after deployment) of a sixth aspect of a tissue marker 325. Tissue marker 325 includes a Tissue marker 325 employs an "overcenter" method of holding legs 327 together after deployment. When deployed, the bending of spring beam 328 provides a locking force to hold hinge crown 326 in the deployed configuration as shown in FIG. 3-21. Tissue marker 325 may be made of a biocompatible polymer.

FIG. 3-22 is a top view, FIG. 3-23 is a side view (before deployment), and FIG. 3-24 is a side view (after deployment) of a seventh aspect of a tissue marker 329. Tissue marker 329 includes a clip 332 having a pair of legs 331 and molded from a biocompatible plastic. Clip 332 retains a thin washer 330 in a first position (before deployment) and a second position (after deployment). Washer 330 may be formed from a metal, a rigid polymer, or an absorbable material. Washer 330 holds legs 331 together after deployment, thus entrapping tissue therebetween.

FIG. 3-25 is a top view, and FIG. 3-26 is a side view, of an eighth aspect of a tissue marker 333. Tissue marker 333 includes a button 334 attached to one end of a flexible (but stiff) cord 335. An T-fastener 336 is attached to the other end of cord 335. During deployment, T-fastener 336 is momentarily bent approximately parallel to cord 335 and penetrated into tissue. When released, T-fastener 336 resumes the original T-shaped configuration with cord 335, thus attaching tissue marker 333 to the tissue. Tissue marker 333 may be made of a biocompatible polymer.

FIG. 3-27 is a top view, FIG. 3-28 is a sectional side view (before deployment), and FIG. 3-29 is a side view (after deployment) of a ninth aspect of a tissue marker 337. Tissue marker 337 includes a metal disc 339 from which extends a pair of hooks 338 integrally formed from disc 339 in a stamping process. Before deployment, hooks 338 extend from the top side of disc 339. After deployment, hooks 338 extend from the bottom side of disc 339, thus entrapping tissue and attaching tissue marker 337 to the tissue.

FIG. 3-30 is a top view, FIG. 3-31 is a side view before deployment, and FIG. 3-32 is a side view after deployment, of a tenth aspect of a tissue marker 340. Tissue marker 340 includes a metallic clip 341, to which is attached a loop 342. A surgeon may attach tissue marker 340 to tissue using any one of a number of conventional, surgical grasping and clamping instruments. FIG. 3-38 is an illustration of tissue marker 340 being attached to tissue 399 using an endoscopic grasping instrument 372. Loop 342 may be color coded to designate key anatomical landmarks, and also provides a convenient handle for manipulating tissue during the procedure, or for attaching additional labels.

Surgeons have used marking pens routinely for marking incision lines on the skin of patients, but before now, specialized instruments and methods for marking lines on the surfaces of soft tissue inside the body have not been available. In addition to using tissue markers to identify key anatomical structures, the surgeon may also use marking fluids, for example, to indicate internal cutting lines during the planning of a surgical procedure.

FIG. 3-33 is a side view of a first embodiment of a marking tissue applier 343, which includes a syringe 348, a connector 347, a tube 346, a stylus 345, and a dispensing tip 344. The surgeon may insert stylus 345 into the body cavity via a laparoscopic port. For hand-assisted surgery, stylus 345 may be approximately 5-10 centimeters long and handheld (like a pencil) by the surgeon inside the body cavity. For laparoscopic surgery, stylus 345 may be much longer (over 20 centimeters) for access into the abdomen via a trocar cannula. Syringe 348 may be filled with any one of a number of marking fluids, including a biocompatible dye, stain, or colored adhesive. The surgeon may hold the dispensing tip 344 near the tissue to be marked (see FIG. 3-39) and inject drops of marking fluid onto the tissue along the desired cutting line.

FIG. 3-34 is a top view, and FIG. 3-35 is a side view of the distal portion of a second embodiment of a marking fluid applier 349. Marking fluid applier 349 includes a pair of opposable arms 351 extending from the distal end of a closing tube 350 and normally biased in an open configuration. An end effector 352 is attached to each of arms 351 and configured for grasping tissue (a closed configuration is shown with phantom lines) when closing tube 350 is moved distally by an actuator on a handle (not shown). FIG. 3-36 is an enlarged, side view of a tissue interfacing surface 354 on one of end effectors 352. Surface 354 contains a multiplicity of holes 353 for dispensing the marking fluid from a reservoir inside of end effector 352 (hidden) to the interfacing tissue. A tube 355 supplies marking fluid to end effector 352 from a syringe or other type of dispensing device on the proximal portion of the instrument (not shown). The diameter of holes 353 is dictated primarily by the viscosity of the marking fluid. Alternately, an absorbent material such as a foam rubber may be used in combination or instead of holes 353, so that marking fluid may be properly transferred from the reservoir to the tissue without excessive dripping, etc.

The surgeon may use the tissue markers and marking fluids described for FIG. 3-1 through FIG. 3-39 to help plan and execute a surgical procedure by identifying key, anatomical structures in the body cavity. A method for performing a sigmoidectomy (removal of the sigmoid colon) is briefly described in conjunction with FIG. 3-37, and a method for performing a left colonectomy (removal of the left colon) is briefly described in conjunction with FIG. 3-40 through FIG. 3-42. The broad method that includes the step of marking key anatomical structures, however, is equally applicable to numerous other surgical procedures, including any type of colonectomy, nephrectomy, adrenalectomy, hepatic resection, distal gastrectomy, and exploratory surgery such as for trauma (knife and gunshot wounds, etc.) and peritonitis.

FIG. 3-37 is an illustration of the colon 360 of a surgical patient. A distal end point 366 is marked by tissue marker 301, and a proximal end point 368 is marked by another tissue marker 301 to identify the portion (with adequate margin of healthy tissue) of the diseased sigmoid colon 362 to be resected. The mesenteric artery 370, which supplies arterial blood to the sigmoid colon 362, is marked by another tissue marker 301. A cutting line 364 is marked by a marking fluid 372. A method for resecting tissue from the body of a patient may include the following steps, although not necessarily in the order described. The surgeon accesses the body cavity, such as through a laparoscopic port or disc. The surgeon identifies and attaches a first tissue marker to the distal end point of the tissue to be resected. The surgeon identifies and attaches a second tissue marker to the proximal end point of the tissue to be resected. The surgeon identifies a cutting line and marks the cutting line with a marking fluid. The surgeon identifies and attaches a third tissue marker to the vessel that supplies arterial blood to the tissue to be resected. The surgeon ligates the arterial blood supply where the third tissue marker is attached. The surgeon resects the tissue between the first and second tissue markers, and along the cutting line. The surgeon removes the tissue from the body cavity of the patient.

FIG. 3-40 illustrates a portion of the colon 360 of a surgical patient, showing tissue marker 340 attached at a proximal end point 368, and a cut line identified by marking fluid 372. (The distal end point 366 is not visible.) A retraction device 374, attached to the body wall at first attachment 375 and second attachment 376, assist the surgeon in visualizing and accessing the surgical site. FIG. 3-41 illustrates the next stage of the procedure, in which the mesenteric artery 370, has been ligated with a surgical clip to block the blood supply to the tissue to be resected. Also, a portion of cutting line 364 has been cut (with a electrosurgical cutting instrument, for example) to create a window in the mesentery for insertion of a stapling instrument. FIG. 3-42 illustrates the next stage of the procedure, in which the surgeon has stapled and cut across the colon 360 to isolate the proximal portion of the tissue to be resected from the surrounding healthy tissue. The surgeon may do a similar stapling and cutting of the distal portion of the colon 360.

Intra-abdominal Storage Device

FIG. 4-1, FIG. 4-2, FIG. 4-3, and FIG. 4-4 are perspective views of a first, a second, a third, and a fourth aspect, respectively, of an intra-abdominal storage device, also referred to as a storage device. A surgeon may use the storage device for temporarily storing surgical instruments intra-abdominally (inside the abdominal cavity) during hand-assisted laparoscopic (HAL) surgery. The surgeon may also use the storage device to store and/or retrieve other objects associated with the surgery, such as tissue specimens, sutures, and sponges, and in other types of surgery, including open or thoracic procedures. During the HAL procedure and other minimally invasive procedures, the surgeon uses endoscopic visualization and has available a wide assortment of endoscopic instruments to aid in the placement, use, and removal of the storage device.

FIG. 4-1 is a perspective view of the first aspect of a storage device 402A, which includes a pouch 404 having an opening 408 and a compartment 403, a closing element 406, and an attaching element 410A. Pouch 404 may be made of a thin, flexible, biocompatible material that is resistant to tearing and puncture. For example, pouch 404 may be made of any one of numerous polymers including polyvinylchloride, polyethylene, polyester, polyurethane, and silicone films, and may alternately be made of a paper material, a mesh, or a fabric woven from a natural or synthetic fiber. Storage device 402A and its packaging, as provided to the surgeon, may be sterilized using conventional methods such as gamma radiation, and in general, is made of cost-effective, disposable materials.

The surgeon may removably attach storage device 402A to the inside of the body wall of the patient using attaching element 410A, so that the surgeon may easily access storage device 402A during the surgical procedure to insert or remove surgical instruments. In this first aspect, attaching element 410A may be made of a braided or monofilament suture material, or any one of a number of materials having appropriate tensile strength, including stainless steel wire, natural fibers, and polymers.

In the first, second, third and fourth aspects of the storage device (402A, 402B, 402C, and 402D, respectively) closing element 406 is a purse string disposed around the perimeter of opening 408. Numerous other possible variations of closing element 406 include, but are not limited to, a clip, wire twist, snap, button, spring wire device such as used for some coin purses, and an interlocking seal, such as "ZIPLOC" (trademark, S.C. Johnson and Co.) that is well known for the application of food storage bags.

Attaching element 410A is joined to a retaining element 412, which provides a flat and robust attachment to pouch 404 to secure storage device 402A to a structure in the body cavity. Retaining element 412 may be secured to the inside of pouch 404 by any one of a number of methods, including adhering, sewing, or capturing in a fold of pouch 404. Retaining element 412 is a thin, flat, and relatively rigid, compared to the material of pouch 404, and may be made, for example, of a biocompatible plastic or paper. Retaining element 412 may alternately be secured to the outside of pouch 404.

During the surgical procedure, the surgeon may introduce storage device 402A into the body cavity of the patient via the main surgical opening that provides access to the surgical site. The surgeon may fold or roll up storage device 402A to facilitate insertion into the body cavity, either via the primary surgical incision (that may contain a hand port or laparoscopic disc) or via a trocar cannula. As illustrated in FIG. 4-9, attaching element 410A may be provided with a surgical needle 411 attached to the free end so that the surgeon may pass the needle through the body wall from inside of body cavity 494 to outside of the body, thus minimizing the size of the wound and eliminating the step of first making an body incision in body wall 494 for passing attaching element 410A. Under laparoscopic visualization on the operating room monitor, the surgeon may insert and remove surgical instruments into opening 408. Alternately, the surgeon may pass the free end of attaching element 410A (without needle 411) through a small incision in the body wall, pulling attaching element 410A outwardly to position storage device 402A against the inside of the body wall. The surgeon may secure the free end of attaching element 410A to the patient's skin using, for example, tape, suture, or staples. The surgeon may change storage device 402A from an open configuration to a closed configuration by holding slip knot 407, while pulling on the free end of closing element 406. Conversely, the surgeon may change storage device 402A from the closed to the open configuration by loosening closing element 406, in order to retrieve a surgical instrument. At the end of the surgical procedure, the surgeon may easily detach the free end of attaching element 410A from the patient, and remove storage device 402A from within the body cavity. Although not shown in the drawings, a suture needle may also be provided on the free end of closing element 406, so that the free end of closing element 406 may be externalized, thus allowing the surgeon to close storage device 402 from outside the body.

Storage device 402A and the other aspects of the storage device, may be manufactured in a number of different sizes to accommodate various surgical procedures. For HAL procedures in which the surgeon may desire to temporarily store very small, fingertip instruments inside of the patient's body, for example, the diameter of opening 408 may be approximately in the range of 3-5 cm, and the length of pouch 404 may be approximately in the range of 5-10 cm.

FIG. 4-2 is a perspective view of the second aspect of a storage device 402B including pouch 404 having an opening 408. A partition 422 separates a first compartment 418 from a second compartment 420. The surgeon may temporarily store a surgical instrument inside of each of first compartment 418 and second compartment 420, keeping them separated by partition 422, and thus allowing easy retrieval of one or the other instruments. The surgeon may use closing element 406, as described for the first aspect, for closing and opening storage device 402B.

FIG. 4-3 is a perspective view of the third aspect of a storage device 402C, including pouch 404 having opening 408. A partition 435 separates a first compartment 424, a second compartment 426, and a third compartment 428. The surgeon may separately store three surgical instruments in the third aspect of storage device 402C.

FIG. 4-4 is a perspective view of the fourth aspect of a storage device 402D, including pouch 404 having an opening 408. A partition 446 separates a first compartment 438, a second compartment 440, a third compartment 442, and a fourth compartment 444. The surgeon may separately store four surgical instruments in the fourth aspect of storage device 402D.

Those skilled in the art will also recognize that storage devices 402B, 402C, and 402D may be constructed using any one of numerous techniques. For example, separate plastic or cloth bags may be joined together to form a pouch with multiple compartments. Alternately, a single sheet of polymeric material may be folded and joined at seams by welding, gluing, or sewing, for example, to form a multi-compartment pouch. The plurality of compartments may also be arranged in a row or in other arrangements.

FIG. 4-5, FIG. 4-6, FIG. 4-7, and FIG. 4-8 show embodiments of the attaching element, as adapted for the third aspect of storage device 402C, although all embodiments are equally adaptable to the other aspects of the storage device. Each embodiment allows the surgeon to removably secure storage device 402C within a body cavity of a patient during a surgical procedure.

FIG. 4-5 is a perspective view of storage device 402C, including a second embodiment of attaching element 410B that includes an attaching rod 456 and a button 460. Attaching rod 456 may be made of a biocompatible plastic or metal and attached to retaining element 412, or attaching rod 456 and retaining element 412 may be injection molded from plastic as one piece. Attaching rod 456 may also be made of a flexible material, such as high density polyethylene, and passed through an incision already made in the body wall by the surgeon. Button 460 may be made of a plastic such as polyethylene. The surgeon introduces storage device 402C into the body cavity of the patient, and pushes a piercing tip 459 of attaching rod 456 through the body wall, externalizing piercing tip 459 and a portion of attaching rod 456. The surgeon holds storage device 402C firmly against the inside of the body wall and (perhaps with assistance) positions button 460 onto attaching rod 456 so that a slot 462 of button 460 engages one of a plurality of teeth 458 on attaching rod 456, thus holding storage device 402C securely against the inside of the body wall. The surgeon may cover, bend over, or cut-off tip 459 to avoid accidental injury during the rest of the surgical procedure. The surgeon may remove button 460 from attachment rod 456 in order to relocate storage device 402C or to remove storage device 402C from the body cavity. The surgeon may also bend over the externalized portion of attaching rod 456 and tape it to the skin of the patient, rather than use button 460.

FIG. 4-6 is a perspective view of a third embodiment of an attaching element 410C, including an attaching rod 464 having a plurality of holes 466, and a pin 468. Attaching rod 464 may be made of a rigid, biocompatible plastic or metal. Attaching rod 464 is attached to or molded as one piece with retaining element 412. Attaching rod 464 includes a piercing tip 469 so that attaching element 410 may be positioned in the body wall as described for the first embodiment shown in FIG. 4-5. Once a portion of attaching rod 464 is externalized from within the body cavity, the surgeon may insert a pin 468 into one of the plurality of holes 466 in attaching rod 464, to secure storage device 402 inside of the body cavity. The piercing tip may be covered, bent over, or cut-off to prevent accidental injury during the procedure. Upon completion of the surgical procedure, the surgeon may easily remove pin 468 and withdraw storage device 402C from the body cavity.

FIG. 4-7 is a perspective view of a fourth embodiment of an attaching element 410D, including an elastic loop 470 attached to retaining element 412. The surgeon may externalize a portion of elastic loop 470 through a small incision in the body wall, and hold storage device 402 against the inside of the body wall, for example, by pulling up on elastic loop 470 and clamping surgical clamps onto elastic loop 470 against the skin of the patient. Alternately, elastic loop 470 may be stretched around the portion of the trocar cannula extending into the body cavity, or around a portion of any one of a number of surgical instruments used during the surgical procedure and having at least a portion extending inside of the body cavity. Elastic loop 470 may be made of a biocompatible elastomer, for example, such as silicone rubber or polyurethane rubber.

FIG. 4-8 is a perspective view of a fifth embodiment of an attaching element 410E, including a clip 472 attached to retaining element 412 with a fastener 474. The surgeon may removably attach clip 472 to the internal portion of the cannula of a surgical trocar port as shown in FIG. 4-10. Fastener 474 may be a post that is molded integrally with retaining element 412, and loosely heat-staked to clip 472, so that clip 472 may pivot. Clip 472 is made of a biocompatible, spring-like plastic or metal so that clip 472 may grip onto the trocar cannula. FIG. 4-11 illustrates storage device 402C in the closed configuration and with the fifth embodiment of attaching element 410D (not shown in FIG. 4-11; see FIG. 4-10) removably attached to the cannula 498 of a surgical trocar 496 penetrating body wall 490. Closing element 406 has been drawn through slip knot 407 to securely contain a surgical instrument 499 within storage device 402C.

FIG. 4-12 is a sectional view of a sixth embodiment of an attaching element 410F, shown on storage device 402A in the open configuration and within the body of a patient. Sixth embodiment of attaching element 410F includes a tubular attaching rod 484 and a cap 486. Attaching rod 486 has a flange 480, which is analogous to retaining element 412, and is made of a biocompatible metal or plastic. The surgeon may initially penetrate attaching rod 484 into body wall 490 as described for the embodiments of the attaching element shown in FIG. 4-5 and FIG. 4-6. The sixth embodiment shown in FIG. 4-12 includes the free ends of closing element 406 (which is again a purse string disposed about opening 408)) extending through a channel 477 of attaching rod 484 so that the surgeon may close or open storage device 402C from outside of the patient. The surgeon may removably press cap 486 over attaching rod 484, as shown in FIG. 4-13, to hold storage device 402C in the closed configuration and to protect a piercing tip 479. A cap flange 482 presses against the outside of body wall 490 to retain storage device 402C against the inside of body wall 494. Cap 486 is made of a biocompatible plastic or elastomer and has a tight sliding fit over attaching rod 484.

Other embodiments for the attaching element are possible. For example, attaching element may incorporate a ferrous material attached to the pouch and held against the inside of the body wall using an external magnet.

Surgical Retraction Device for Creating a Visceral Barrier

The viscera inside the abdominal cavity is highly mobile and slippery. During a hand-assisted laparoscopic procedure, for example, the surgeon may need to "compartmentalize" the abdominal cavity in order to view and operate on particular organs. During some laparoscopic procedures, the surgeon tips the operating table to cause the patient's abdominal viscera to shift away from an area of interest in the body cavity. The surgeon may refrain from tipping certain patients (gunshot wounded patients, elderly patients, etc.) to minimize stress on the heart. In those and other cases, the surgeon may use any one of the numerous aspects of a retraction device illustrated in FIG. 5-1 through FIG. 5-52 to "corral" viscera (such as the colon) out of the way, or to "put away" tissues already examined. The retraction device helps the surgeon to create a wall-like structure, or visceral barrier, at a transverse abdominal line somewhere between the rib cage and the pelvis. The retraction device has a tissue interface with a large, projected area for holding the viscera away from the surgical site. The surgeon may use the retraction device to lift or to suspend tissue, such as when examining the vasculature the intestinal mesentery. The retraction device generally is easy to manipulate and position in the body cavity, easy to hold in position for the duration of the procedure, and easy to remove from the body cavity.

Turning now to the drawings, FIG. 5-1 illustrates a first aspect of a surgical retraction device 501 retracting a colon 500 of a surgical patient. Retraction device 501 includes an elongated column 502 removeably attached to an attachment handle 504 centrally located on a rectangular, barrier element 503. Column 502 includes a conventional, laparoscopic, surgical clamping instrument that the surgeon may pass through a laparoscopic port (not shown) before attaching to attachment handle 504. The surgeon may introduce barrier element 503 into the body cavity, for example, via the laparoscopic disc. Barrier element 503 is formed from a malleable material, such as a metallic wire reinforced, biocompatible elastomer. Barrier element 503 has a length of approximately 20 centimeters and a width of approximately 5 centimeters. The surgeon may use retraction device 501 in combination with a number of ancillary, surgical instruments 599, to manipulate and support visceral tissues in the body cavity. Once the surgeon is satisfied with the placement of the visceral barrier, the external portion of column 502 may be held by a surgical assistant, weighted, or temporarily attached to an immobile structure outside the body cavity.

The surgeon may use each of the remaining aspects of the retracting device in a similar fashion as the first aspect of FIG. 1, with some variations as will be described. FIG. 5-2 is a perspective view of a second aspect of a retraction device 505, which includes a bifurcated column 506 having a pair of arms 509. The end of each of arms 509 pivotally attach to the opposing sides of a book-like, foldable barrier element 507. A remotely operable, actuating rod 508 of column 506 attaches to barrier element 507 so that the surgeon may change retracting device 505 between a closed configuration and an opened configuration. The surgeon may introduce the distal portion of retracting device 505 into the body cavity via a laparoscopic disc.

FIG. 5-3 is a perspective view of a third aspect of a retraction device 510 including a column 511 removeably attached to a barrier element 512. Barrier element 512 has a plurality of vacuum apertures 513, which fluidly communicate via a channel through column 511 with a vacuum source (not shown). Barrier element 512 is covered with a cover material 514, which may comprise a cotton gauze or fabric, to improve the surgeon's ability to manipulate tissue atraumatically. The surgeon may introduce barrier element 512 through a laparoscopic disc or port before attaching it to the distal end of column 511.

FIG. 5-4 is a perspective view of a fourth aspect of a retraction device 515, while in a closed configuration, and FIG. 5-4 shows retraction device 515 in an opened configuration. Retraction device 515 includes three arms 517 extendable from the open, distal end of a column 516. A barrier element 518, including a flexible material such as a fabric or plastic film, is attached to arms 517, so that when arms 517 are remotely actuated by the surgeon to extend from the end of column 516, arms 517 spread apart and tension barrier element 518.

FIG. 5-6 is a perspective view of a fifth aspect of a retraction device 519, while in a closed configuration, and FIG. 5-7 shows retraction device 519 in an opened configuration.

Retraction device 519 includes a pair of parallel bars 521 that are extendable from the distal end of a column 520 so that bars 521 are perpendicular to column 520 in the opened configuration. Bars 521 are pivotally attached to column 520 so that bars 521 are parallel to column 520 in the closed configuration, and so that the surgeon may pass the distal portion of retraction device 519 through a laparoscopic port. A barrier element 523 is formed by a webbing material.

FIG. 5-8 is a perspective view of a sixth aspect of a retraction device including a pair of L-shaped, bar elements 526 that are covered with a cover material 527, and each of which are attached at a common pivot 593 to the distal end of a column 525. The surgeon may actuate bar elements 526 to be approximately flush with the outside diameter of column 525 while in a closed configuration, and to swing out to be perpendicular to column 525 while in an opened configuration.

FIG. 5-9 is a perspective view of an seventh aspect of a retraction device 528 including a barrier element 530 that is extendable from the open end of a column 529. Barrier element 530 may be formed from a flat stock of spring steel that forms a ninety degree bend when unconstrained. Barrier element 530 is covered with a cover material 531.

FIG. 5-10 illustrates an eighth aspect of a retraction device 532, while in an opened configuration and retracting the colon 500 of a surgical patient. Retraction device 532 includes a pair of arms 534 attached to an attachment handle 535, which a surgeon may hold with a conventional laparoscopic clamp 533. Arms 534 may be opened as shown to form a V-shape, tensioning a pair of cords 537 attached to arms 534. A webbing type, barrier element 536 is attached to cords 537 and arms 534, forming a large, see-through, tissue interface surface while in an opened configuration.

FIG. 5-11 illustrates a ninth aspect of a retraction device 538, while in an opened configuration and retracting the colon 500 of a surgical patient. Retraction device 538 includes a webbing type, barrier element 542 attached to a collapsible, elliptical ring 594, which may be made of a spring steel wire or a shape-memory metal (Nitinol). The ends of a beam element 541 are attached to ring 594. A handle 542 centrally located on beam element 541 provides a convenient grasping point for a laparoscopic clamping instrument 539.

FIG. 5-12 is a perspective view a tenth aspect of a retraction device 543 in a closed configuration. FIG. -13A shows retraction device 543 while in a partially open configuration. FIG. 5-13B shows retraction device 543 while in an opened configuration. Retraction device 543 includes a barrier element 545 that passes through a hollow column 544. Barrier element 545 is formed by a band composed of a flexible but stiff material such as high density polyethylene. The distal end of barrier element 545 extends out of the open, distal end of column 544, and is attached to an attachment canopy 547 on the outside of column 544. As shown in the drawings, the surgeon may remotely push barrier element 545 out of the open end of column 544 to form a T-shape, supported in the center of the extended barrier element 545 by a remotely operable rod 546.

FIG. 5-14 is a perspective view of an eleventh aspect of a retraction device 548 including a pair of arms 550 that may be retracted into the open end of a column 549 by a retraction rod 595.

FIG. 5-15 is a perspective view of a twelfth aspect of a retraction device 551, shown retracting the colon 500. Retraction device 551 includes a pair of arms 553 formed from a flat, spring material and extendable from a column 552.

FIG. 5-16 is a side view of a thirteenth aspect of a retraction device 554 while in an opened configuration. FIG. 5-17 shows a partially opened configuration, and FIG. 5-18 shows a closed configuration. Retraction device 554 includes a barrier element 558 formed by a collapsible frame 556 and a webbing 557. Barrier element 558 is retractable into the open end of a column 555, to facilitate introduction into and removal from the body cavity via a laparoscopic port.

FIG. 5-19 illustrates a fourteenth aspect of a retraction device 559 retracting the colon 500 of a surgical patient. Retraction device 559 includes a pair of arms 561 that spring apart when not constrained inside the open end of a column 560. On the end of each arm is a pad 562 having an atraumatic cover 563 (see FIG. 5-20).

Each of the following aspects of the retraction device (shown in FIG. 5-21 through FIG. 5-52) comprise a wall-like, barrier element that optionally may be positioned and held in the body cavity by a laparoscopic clamping instrument. For clarity, the clamping instrument is not shown in some of FIG. 5-21 through FIG. 5-52. Each of the following aspects of the retraction device may be "self-supporting" inside of the body cavity. That is, the perimeter of the barrier element is positionable against the body wall and organs within the body cavity to remain in place without being held by a clamping instrument. In most aspects to be described, however, handles are provided on the barrier elements to facilitate manipulation and holding by a clamping instrument. Each of the aspects of the retracting device shown in FIG. 5-21 through FIG. 5-52 may be sized, while in the opened configuration, to substantially span either or both the transverse width and the vertical height of the patient's body cavity.

FIG. 5-21 is a sectional view of a fifteenth aspect of a retraction device 564, while in a closed configuration and being passed through a laparoscopic port. FIG. 5-22 is an end view of retraction device 564, while in the extended configuration. FIG. 5-23 is a front view of retraction device 564, while in the closed configuration. Retraction device 564 includes a plurality of panel barrier elements 565 attached together, edge-to-edge, in a row by a plurality of hinges 567. Retraction device 564 includes a plurality of handle cutouts 566 to facilitate grasping by a clamping instrument. In one version of this aspect, each of hinges 567 may flex in either direction so that panels 565 may be rolled up from either side. In another version of this aspect, hinges 567 may flex in only one direction so that panels 565 may be rolled up from only one side. When unrolled to the opened configuration, retraction device 564 resists bending from one direction.

FIG. 5-24 is a front view of a sixteenth aspect of a retraction device 568 including a first barrier element 569 and a second barrier element 570 that interlock at a central, interlocking joint 571 once introduced into the body cavity. A cover material 572, such as a gauze of fabric, covers each of first and second barrier elements, 569 and 570. The surgeon may hold retraction device 568 with a clamping instrument clamped onto one of handles 573.

FIG. 5-25 illustrates an seventeenth aspect of a retraction device 574 retracting the colon 500 of a surgical patient. FIG. 5-26A is a front view of retraction device 574, while in an opened configuration. FIG. 5-26B is a front view of retraction device 574, while in a partially closed configuration. Retraction device 547 includes four panel barrier elements joined together at folds 577, and includes a plurality of handle cutouts 576. Retraction device 547 may be die-cut from a polyethylene sheet, for example, with folds 577 including thermally-formed creases. As shown in FIG. 5-26B, retraction device 574 is foldable in a concertina manner, and may be easily deployed into the opened configuration while inside the body cavity.

FIG. 5-27 illustrates an eighteenth aspect of a retraction device 578 retracting the colon 500 of a surgical patient. Retraction device 578 includes a barrier element 579 formed by a plurality of frames 581 flexibly joined in a row, side-to-side. Each of frames 581 is covered with a mesh or webbing material.

FIG. 5-28 illustrates a nineteenth aspect of a retraction device 582 retracting the colon 500 of a surgical patient. Retraction device 582 includes a barrier element 583 formed from a sheet of flexible, biocompatible material, such as polyethylene, and including a plurality of handle cut-outs 584.

FIG. 5-29 is a perspective view of a twentieth aspect of a retraction device 585 including a barrier element 586 injection molded from a biocompatible polymer such as polypropylene. Retraction device 585 includes a plurality of handle projections 587 extending from one side of barrier element 586, and a plurality of handle cutouts 588.

FIG. 5-30 is a front view of a twenty-first aspect of a retraction device 589, while in a first, partially closed configuration. FIG. 5-31 shows retraction device 589, while in a second, partially closed configuration. FIG. 5-32 shows retraction device 589, while in an opened configuration. Retraction device 589 includes four panel barrier elements joined by a plurality of hinges 591, and including a plurality of handle cutouts 592. Retraction device 589 may be formed, for example, by either a die-cutting or an injection molding process from a biocompatible polymer.

FIG. 5-33 is a top view and FIG. 5-34 is a front view of a twenty-second aspect of a retraction device 5000, which includes four panel barrier elements 5001 joined edge-to-edge in a row by three pinned hinges 5002 that swing in either direction. Panels 5001 may be formed from a metal or injection molded from a biocompatible polymer. Each of hinges 5002 may contain a detent or locking feature that holds panels 5001 in the instant configuration until a sufficient external force is applied. Retraction device 5000 includes a plurality of handle cutouts 5003.

FIG. 5-35 is a top view and FIG. 5-36 is a front view of a twenty-third aspect of a retraction device 5005. Retraction device 5005 includes four panel barrier elements 5006 joined together in a row by a plurality of flexible bands 5007 woven alternately on the front and the back sides of each of barrier elements 5006, forming three hinges 5008 that may swing in either direction. A surgeon may extend and position retraction device 5005 in the body cavity and allow the abdominal wall to rest on the top edge of retraction device 5005, perhaps by reducing insufflation pressure in the body cavity, so that retraction device 5005 may remain extended while resisting the force of tissue bearing against it.

FIG. 5-37A is a top view and FIG. 5-38 is a front view of a twenty-fourth aspect of a retraction device 5010, while in an extended configuration. FIG. 5-37B is a detailed, top view of retraction device 5010, while being folded into a rolled-up or closed configuration. Retraction device 5010 includes a plurality of panel barrier elements 5011 joined together edge-to-edge in a row by a plurality of hinges 5013. A plurality of wires 5012 embedded in barrier elements 5011 form hinges 5013. A plurality of stop elements 5009 attached to or integrally formed on the tissue-bearing side of each of panel barrier elements 5011 are arranged so that retraction device 5010 may fold in only one direction. This allows the surgeon to introduce retraction device 5010 while in the rolled-up or closed configuration into the body cavity. When in the extended configuration, retraction device 5010 resists the force of tissue bearing against it, so that it remains extended.

FIG. 5-39 is a top view, FIG. 5-40 is a front view, and FIG. 5-41 is an end view of a twenty-fifth aspect of a retraction device 5015. Retraction device 5015 includes a malleable barrier element 5016 formed from a metallic mesh 5018 embedded in a biocompatible, elastomeric material 5019. Metallic mesh 5018 may be formed from a screen-like material, a plurality of wires or rods, and the like. Barrier element 5016 includes a plurality of fingers 5017 that may be bent over to a desired shape to fit inside the body cavity and properly retract tissue. The surgeon may easily form barrier element 5016 into the desired shape after placement into the body cavity, but barrier element 5019 is stiff enough to provide a visceral barrier.

FIG. 5-42 is a front view of a twenty-sixth aspect of a retraction device 5021. FIG. 5-43 shows retraction device 5021, while in a twisted configuration. Retraction device 5021 includes a barrier element 5024 formed from a metallic mesh 5022 covered with an polymeric, biocompatible coating. The surgeon may easily form barrier element 5024 into the desired shape after placement into the body cavity, but barrier element 5024 is stiff enough to provide a visceral barrier.

FIG. 5-44 is a top view and FIG. 5-45 is a front view of a twenty-seventh aspect of a retraction device 5027, including a plurality of panel barrier elements 5028 joined together edge-to-edge in a row by a pair of flexible bands 5030. Because barrier elements 5028 are assembled with substantially no gap between adjoining barrier elements, and because bands 5030 are affixed to only one side of barrier elements 5028, retraction device 5027 may flex in only one direction. The surgeon may position retraction device 5027 against the viscera so that retraction device 5027 is flexible in the distal direction (towards the viscera) to create the visceral barrier. A flexible, plastic cover 5029 is provided to cover potential pinch-points between adjoining barrier elements 5028.

FIG. 5-46 is a top view and FIG. 5-47 is a front view of a twenty-eighth aspect of a retraction device 5031, including a barrier element 5032 formed by a plurality of nested segments 5033 that may telescope in one direction between an opened and a closed configuration. A second retraction device 5031 may be joined by numerous methods (barb and hook latches, for example) to a first so that the two nested segments 5033 of the two retraction devices 5031 telescope in opposing, lateral directions. Sliding-fit frictional force, detents, or interlocking features may be incorporated into nested segments 5033 to hold retraction device 5031 in the desired configuration to provide an effective visceral barrier, yet be adjustable by the surgeon within the body cavity.

FIG. 5-48 is a top view and FIG. 5-49 is a front view of a twenty-ninth aspect of a retraction device 5035, including a plurality of panel barrier elements 5036 joined together, edge to edge in a row, by a plurality of hinges 5037. Barrier elements 5036 may be unitarily formed, such as by die-cutting from a sheet of polyethylene. Hinges 5037 may be thermally formed creases in the sheet material. A plurality of extendable fingers 5039, which may be made from the same material as barrier elements 5036, are pivotally attached to barrier elements 5036. The surgeon may swing each of fingers 5039 independently between a down and an up position as required, to increase the effective height of the visceral barrier. Retraction device 5035 also includes a plurality of windows 5038 for viewing through the device or for grasping with a clamping instrument.

FIG. 5-50 is a top view of a thirtieth aspect of a retraction device 5042. FIG. 5-51 is a front view of retraction device 5042, while in a closed configuration. FIG. 5-52 is a front view of retraction device 5042, while in an opened configuration. Retraction device 5042 includes a hollow, barrier element 5043 that houses a curtain 5047 in the closed configuration. The ends of a flexible dowel 5045 are inserted into the opposing ends of barrier element 5043. An external loop portion 5040 of dowel 5045 wraps around approximately one half of the perimeter of barrier element 5043. The ends of dowel 5045 are operably connected to an extension mechanism 5046 inside of barrier element 5043. The top of curtain 5047 is attached to loop portion 5040, and the bottom of curtain 5047 is retained inside of barrier element 5043. The surgeon may grasp a handle 5044 with a clamping instrument and rotate handle 5044 in the counter clockwise direction to deploy curtain 5047 to extend the height of barrier element 5043. Curtain 5047 may be formed from any one of a number of fabrics, mesh materials, films, and the like.

FIG. 5-53, FIG. 5-54, and FIG. 5-55 show a thirty-first aspect of a retraction device 5050 including at least one central panel 5052 of uniform thickness, and a pair of end panels, 5054 and 5056, each attached to central panel 5052 by at least one flexible hinge element 5058, and each having a non-uniform thickness that tapers in a direction away from hinge element 5058. As shown in FIG. 5-55, end panels 5054 and 5056 may fold onto central panel 5052 so that the overall thickness of retraction device 5050 is relatively small as compared to a similar device in which all panels have a uniform thickness.

FIG. 5-56 is a front view and FIG. 5-57 is an end view of a thirty-second aspect of a retraction device 5060 while in an extended configuration. Retraction device 5060 includes a plurality of panels 5062 joined by a plurality of hinges 5064. Each of panels 5062 may be formed from a spring-like material, such as for example, shape memory metal (Nitinol) so that each panel 5062 may be flattened for rolling up into a closed configuration for introduction into the body cavity. When retraction device 5060 is in the extended configuration, each of panels 5062 may curl as shown in FIG. 5-57 so that retraction device 5060 may resist the force of tissue bearing against one side and form an effective partition.

Surgical Instrument System Having Removably Attachable End Effectors

During some surgical procedures, the surgeon must grasp, clamp, retract, suspend, and/or manipulate soft, fluidic tissues within the insufflated body cavity, being careful not to injure the tissues. In open surgical procedures, the surgeon has a large array of surgical instruments with large end effectors specifically designed for various steps of the procedure. Also in open surgical procedures, the surgeon often places a folded-over, gauze sponge within the end effectors of an open surgery instrument to broaden and soften the tissue interface surface. During traditional, laparoscopic procedures, it is not always possible to pass such large instruments or a folded sponge through a laparoscopic port. During hand-assisted, laparoscopic procedures, however, the lap disc provides a relatively large port for introducing devices into the body cavity, with only momentary loss of insufflation pressure. Consequently, it is possible to provide a surgical system that allows a surgeon to introduce a surgical instrument with extra large end effectors into a body cavity.

FIG. 6-1 through FIG. 6-11 show numerous aspects of surgical instruments, each having removably attachable end effectors that are too large to pass through a conventionally sized trocar cannula. FIG. 6-1 is a front view of the distal portion of a first embodiment of a surgical instrument 601, shown with a first end effector 614 and a second end effector 616. A first arm 604 and an opposable second arm 606 extend from the distal end of an elongated shaft 602, which may pass through a conventional trocar cannula when end effectors 614 and 616 are not attached. Surgical instrument 601 includes a handle with an actuator (not shown) for opening and closing arms 604 and 606. As shown for arm 604 in FIG. 6-2 and FIG. 6-3, each of arms 604 and 606 has an attachment slot 608 and a detent recess 610. Each of first and second end effectors 614 and 616 also has an attachment element 620 for insertion into attachment slot 608, and a detent 612 for engagement with detent recess 610. Each of first and second end effectors 614 and 616 has an atraumatic grasping element 618 made of a soft, elastic, biocompatible material such as a foam rubber. When end effectors 614 and 616 are attached to arms 604 and 606, the distal portion of surgical instrument 601 may be too large to pass through some conventional, laparoscopic ports.

Atraumatic grasping elements 618 may also be formed or coated from any one of a number of medical grade hydrophilic polymers. These polymers have high water permeability, are waterproof, have low water absorption, have high flexibility and impact strength at low temperatures, have good mechanical and elastic properties, have good heat stability, have good resistance to chemicals, and are easy to process. Very common commercial hydrophilic materials are copolymers made of polyethylene oxide, crystallizable polyamide, polyurethane, and polyester.

FIG. 6-4 is a front sectional view of a second embodiment of an arm 626 having an attachment aperture 626 and a female thread 628. An alternate version of an end effector 621 has an attachment element 622 with a male thread 624 for removable attachment to arm 630. Attachment elements 620 and 622 are only examples of the many types of features for removably attaching an end effector to an arm of a surgical instrument, as is apparent to those skilled in the art.

FIG. 6-5 is an end view and FIG. 6-6 is a front view of a second aspect of an end effector 632, including a pair of parallel side walls 634 and 636 connected by three, transverse columns 638 arranged to hold a replenishable, tissue interface element 640. Interface element 640 may be formed, for example, from a conventional, surgical sponge or gauze material. End effector 632 also includes attachment element 620 and detent 612, as shown for end effector 614 in FIG. 6-1, for removable attachment to surgical instrument 601.

FIG. 6-7 is an end view and FIG. 608 is a front view of a third aspect of an end effector, which is the same as end effector 632 shown in FIG. 6-6, but having a replenishable, tissue interface element 644 formed from a roll of biocompatible material such as cotton gauze or a silicone foam tape, for example. Interface element 644 includes a free end 646 that may be pulled by the surgeon to present a fresh surface of interface element 644 to the tissue. Free end 646 may be externalized through the body wall via the laparoscopic port so that the surgeon may remotely replenish interface element 644.

FIG. 6-9 is a front view and FIG. 6-10 is a top view of the distal portion of a surgical instrument 646, shown with a first end effector 650 and a second end effector 652, each of which represent a fourth aspect of an end effector. Surgical instrument 646 includes a pair of opposing, wire-formed arms 654 and 656. The surgeon remotely operates closing tube 648 to translate longitudinally in the distal direction to close arms 654 and 656, and in the proximal direction to open arms 654 and 656. Each of first and second end effectors 650 and 652 has a slot 658 (see FIG. 6-11) for removable attachment onto arms 654 and 656. End effectors 650 and 652 may be formed by any one or a composite of a number of biocompatible materials, including a foam rubber or a low durometer silicone rubber. Slot 658 may be sized to stretch slightly during attachment to one of arms 654 and 656 to insure retention during use.

FIG. 6-12 illustrates part of a first method for performing a hand-assisted, laparoscopic procedure. The method includes providing a surgical instrument system 670 that includes a lap disc 662 and a surgical instrument 601 with a first and a second, detachable end effector, 614 and 616. The method further includes placing lap disc 662 in the body wall 666 of the patient, placing the distal portion of surgical instrument 601 into body cavity 668 when end effectors 614, 616 are not attached to surgical instrument 601, introducing end effectors 614, 616 into body cavity 668 via lap disc 662, and assembling end effectors 614, 616 to surgical instrument 601. For removal of surgical instrument 601, the method further includes removing end effectors 614, 616 from the surgical instrument 601, removing surgical instrument 601 from body wall 666, and removing end effectors 614, 615 from body cavity 668 via lap disc 662. The first method may also include the step of storing the end effectors in an intra-abdominal storage device (see FIGS. 4-1 through 4-15) inside of the body cavity.

FIG. 6-13 illustrates part of a second method of performing a hand-assisted, laparoscopic procedure. The second method includes providing a surgical instrument system 672 that includes a lap disc 662, a lap disc insert 680 having at least one port 682, and a surgical instrument 601 with a first and a second, detachable end effector, 614 and 616. The method further includes placing lap disc 662 in the body wall 666 of the patient, placing the distal portion of surgical instrument 601 through lap disc port 682 of lap disc insert 680, attaching end effectors 614, 616 to surgical instrument 601, and attaching lap disc insert 680 to lap disc 662 so that end effectors 614, 616 are inside body cavity 668. For removal of surgical instrument 601 from body cavity 668, the method further includes removing lap disc insert 680 from lap disc 662 so that end effectors 614, 616 are removed from body cavity 668 via lap disc 662.

The first and second methods for performing a hand-assisted, laparoscopic procedure may also be used with other surgical instruments having removably attachable end effectors. The first and second methods may also include insufflating the body cavity while the end effectors are inside the body cavity.

Tissue Suspension Device

FIG. 7-1 through FIG. 7-13 disclose a tissue suspension device for suspending tissues within the body cavity of a patient. A surgeon may use the tissue suspension device in combination with insufflation, orientation of the patient, and other well-known laparoscopic surgery techniques, to improve visualization of and access to tissues of interest within the abdominal cavity during a hand-assisted, laparoscopic procedure. The surgeon may also use the tissue suspension device for open, abdominal, surgical procedures, to eliminate the need for other retraction devices currently used that partially obstruct the surgical opening, to provide the surgeon with improved access and visualization into the abdominal cavity.

FIG. 7-1 is a side view of surgical patient 799 while abdomen 798 is insufflated with carbon dioxide. For clarity, the associated instruments, systems, and personnel required for laparoscopic surgery are not shown. FIG. 7-2 is a cross-sectional view of patient 799, taken at line 2-2 of FIG. 7-1. A first aspect of a tissue suspension device 702 suspends an organ 796 (in this example, the transverse colon). Tissue suspension device 702 includes an elongated spanning element 704 having a first end 712 removably attached to body wall 794 by a first supporting element 708, and a second end 714 removably attached to body wall 794 with a second supporting element 709. The patient's body wall, therefore, supports the weight of the suspended tissue, as opposed to "wall lift" or "gasless surgery" devices that attach to a structure mounted on the surgical table and are sometimes used in place of insufflation to enlarge the body cavity. Suspension system 702 further includes at least one, hook-like suspending element 706 removably attached to spanning element 704. FIG. 7-1 shows a pair of suspending elements 706 suspending organ 796 within body cavity 792, thereby providing improved access to and visualization of the mesenteric vasculature 790, which supplies blood to organ 796.

FIG. 7-3 through FIG. 7-6 show additional views of suspension system 702. FIG. 7-4 shows spanning element 704 with a plurality of holes 716 arranged to provide multiple positions for inserting a pair of ends 707 of suspending element 706. Each of first end 712 and second end 714 of spanning element 704 includes an offset 728. Offset 728 allows the surgeon to attach spanning element 704 to the body wall while maintaining an assured vertical clearance between the top of the body cavity and spanning element 704. FIG. 7-6A shows first end 712 having a retention portion 726 for the removable attachment of a first elastomeric tube 710 of supporting element 708. FIG. 7-5 shows second end 714 having a retention portion 726 for the removable attachment of a second, elastomeric tube 710 of supporting element 709. In a manner to be described, the surgeon places spanning element 704 across the body cavity so that first end 712 extends through the body wall on one side of the patient and second end 714 extends through the body wall on the opposite side of the patient. Then the surgeon may attach one of tubes 710 on each of first and second ends, 712 and 714. The surgeon next may place one of a pair of cuffs 711 onto each of first and second ends, 712 and 714, to atraumatically support spanning element 704 against the external surface of body wall 794. Each cuff 711 has a pair of parallel slits 713 for "weaving" onto first and second ends, 712 and 714. FIG. 7-6B shows first end 712 assembled to supporting element 708. Cuffs 711 also provide torsional resistance to spanning element 704, which may tend to twist within the body wall when supporting tissue.

The surgeon may position spanning element 704 into the body cavity using a number of methods. For example, the surgeon may first incise body wall 794 with a scalpel, or penetrate the body wall with a sharp tip 722 of second end 714, and then guide second end 714 across the body cavity to avoid accidental injury to internal organs, using his/her hand inserted into the body cavity via the laparoscopic disc. The surgeon may then penetrate the body wall on the opposite side of the patient, or create an incision with a scalpel, to externalize second end 714. In another example, the surgeon may attach a cap 718 (FIG. 7-5) onto retention portion 724 of second end 714. The surgeon may then insert the free end of a filament 720, which may be a metal wire or a suture attached to cap 718, into an entry incision on one side of the patient, and out of an exit incision on the other side of the patient. Then the surgeon may use filament 720 to pull spanning element 704 into the body cavity. Alternately, a needle (not shown) may be attached to the free end of filament 720 for penetration through the body wall.

Once the surgeon has placed spanning element 704 into the body cavity and attached first and second ends, 712 and 714, to the body wall, the surgeon may next hook at least one suspending element into a pair of adjacent holes 716 of spanning element 704, again using his/her hand inserted into the body cavity via the laparoscopic disc. The surgeon may then lift the tissue/organ into suspending element 706. When the surgeon no longer needs suspension system 702, the surgeon may remove suspending element 706, detach either first end 712 or second end 714 from one side of the patient, and pull spanning element 704 out of the opposite side of the patient. Alternately, the surgeon may merely hook suspending element 706 over spanning element 704, rather than using holes 716. Although not shown in the figures, it is possible also to provide spaced-apart, annular grooves along the length of spanning element 704. The surgeon may hook suspending element 706 into the grooves so that suspending element 706 may not slide along the length of spanning element 704, but is permitted to rotate about the axis of spanning element 704.

Each of supporting element 706, spanning element 704, tube 710, and cap 718 may be formed from any one of a number of rigid, biocompatible materials, including a metal such as stainless steel. Supporting element 706 may also be formed from a semi-rigid material, such as a malleable metal coated with an elastomer or hydrophilic material, so that the surgeon can reshape supporting element 706 during the surgical procedure. Supporting element 706 may also be formed from a memory metal (Nitinol) so that it may be folded to facilitate placement into (perhaps through a trocar cannula) or removal out of the body cavity.

FIG. 7-7 through FIG. 7-10 show views of a second aspect of a tissue suspension device 732, including a spanning element 740, a pair of supporting elements 736, and at least one, hook-like suspending element 738. Spanning element 740 is a straight bar having a plurality of holes 740 spaced apart along its length. Each hole is sized and oriented to receive an end 737 of supporting element 736. Suspending element 738 includes a tray 739 onto which the surgeon may hang a tissue/organ. FIG. 7-9 is an enlarged view of supporting element 736, which includes a cord 741 attached to spanning element 734, and a plurality of spaced-apart, bead-like markers 742 attached to cord 741. Supporting element 736 further includes a retaining element 744 having a slot 746 for receiving cord 741 (see FIG. 7-10). Once the surgeon has placed spanning element 734 into the body cavity via the laparoscopic disc or a small incision in the body wall, the surgeon may externalized each cord 741 through an appropriately placed incision in the body wall, and lift up on cord 741 to raise spanning element 734. Alternately, a needle (not shown) may be attached to the free end of each of cords 741, so that the surgeon may penetrate the needle through the body wall from inside the body cavity. The surgeon may use markers 742 to estimate the position of spanning element 734 in the body cavity, and then position retaining element 744 onto cord 741 to hold spanning element 734 at the desired vertical height inside of the body cavity. Spanning element 734 is thereby suspended from the body wall like a trapeze so that the suspended tissue/organ has additional mobility. To remove suspension system 732, the surgeon uses the reverse of the preceding procedure.

Spanning element 734 and suspending element 738 may be formed from any one of a number of rigid, biocompatible materials, including stainless steel. Supporting element 736 and retaining element 744 may be formed, for example, from a polymer. Spanning element 734 may be coated with an anti-bacterial agent and/or a lubricious coating to facilitate insertion through the body wall. At least a portion of supporting element 738 may be coated or covered with a soft material, such as a medical grade hydrophilic material, a foam rubber, or a cotton gauze, to provide an atraumatic support for the tissue/organ. Tray 738 may be formed from a malleable material, such as an annealed stainless steel, so that the surgeon may reshape it while it is inside of the body cavity. Tray 738 may be curved to help retain the slippery tissue within it, and the depth of the curvature may be approximately in the range of, but not limited to, 2-6 centimeters.

FIG. 7-11 shows a partial view of a third aspect of a tissue suspension device 748, including a hollow, spanning element 750 formed from a rigid material such as stainless steel tubing. Spanning element 750 includes a plurality of spaced-apart holes 752 for the removable attachment of suspending element 738 shown in FIG. 7-8. The surgeon places spanning element 750 into the patient using a guide wire 754. The surgeon creates a first incision in the body wall on one side of the patient and inserts an end of guide wire 754. The surgeon then pulls guide wire 754 across the body cavity, using his/her hand inserted into the body cavity via the laparoscopic disc. The surgeon then passes the end of guide wire 754 out a second incision in the body wall on the opposite side of the patient. The surgeon next threads the external portion of guide wire 754 through spanning element 750, and pushes spanning element 750 into the first incision along guide wire 754, across the body cavity, and out the second incision. The surgeon may then remove guide wire 754 from spanning element 750, and secure the externalized ends of spanning element 750 to the skin of the patient using a medical adhesive tape, for example.

FIG. 7-12 shows a fourth aspect of a tissue suspension device 758, including an articulating spanning element 759 made from a titanium alloy or a stainless steel bar or tube, for example, and having a plurality of holes 760 for the removable attachment of suspending element 738 shown in FIG. 7-8. The surgeon may use supporting element 708 shown in FIG. 7-6A to removably attach spanning element 759 to the body wall. At least one end of spanning element 759 has an articulating element 762 that may swing about a pivot 764. The surgeon may adjust articulating element 762 to a shortened configuration while introducing spanning element 759 into the body cavity via the laparoscopic disc. The surgeon may then use a scalpel to create two incisions in the body wall to externalize the ends of articulating element 762 at the locations best suited for supporting spanning element 759.

FIG. 7-13 shows a fifth aspect of a tissue suspension device 768, including a flexible spanning element 770 and a pair of adjustable tension, supporting elements 771. Each of supporting elements 771 include a threaded rod 772 attached with a connector to flexible spanning element 770, and a tensioning knob 774. While knobs 774 are detached from threaded rods 772, the surgeon may position spanning element 770 into the patient using any of the methods described for the previous aspects, so that each of threaded rods 772 extends through the body wall. The surgeon may then screw one tensioning knob 774 on each of threaded rods 772, and tension spanning element 770 by rotating one or both of the tensioning knobs in the appropriate direction. The surgeon may then hook at least one suspending element such as shown in FIG. 7-4 onto spanning element 770. Spanning element 770 may be formed from, but is not limited to, any one or a combination of the following materials: a plastic cord or bar, a braided metal wire, a natural or a synthetic fiber rope, an extruded rubber or plastic tube, a malleable metal bar, a wire-reinforced elastomer, a hydrophilic material, and a "gooseneck" conduit such as used for certain desk lamps.

While the present invention has been illustrated by description of several embodiments, it is not the intention of the applicant to restrict or limit the spirit and scope of the appended claims to such detail. Numerous variations, changes, and substitutions will occur to those skilled in the art without departing from the scope of the invention. Moreover, the structure of each element associated with the present invention can be alternatively described as a means for providing the function performed by the element. Accordingly, it is intended that the invention be limited only by the spirit and scope of the appended claims.

What is claimed is:

1. A surgical access device for providing surgical access through an incision in the body wall to the inside of a body cavity of a patient, the surgical access device having a center axis and comprising:
    an assembly having a proximal end and a distal end and having an opening around the center axis, the assembly comprising a ring, and a sleeve coupled to and extending generally axially from the ring and positionable in the incision, the sleeve defining a passageway through the body wall between the opening in the assembly and the body cavity;
    a subassembly releasably positionable at the proximal end of the assembly and defining at least two apertures sized for accepting surgical instruments; and
    a member disposed radially outwardly and distally with respect to the at least two apertures, the member positioned with respect to the sleeve to protect the sleeve from instruments inserted through the apertures.

2. The surgical access device of claim 1, wherein the apertures are sized from between about five and twelve millimeters.

3. The surgical access device of claim 1, wherein at least one aperture comprises a seal assembly.

4. The surgical access device of claim 3, wherein the seal assembly is an iris seal.

5. The surgical access device of claim 3, wherein the seal assembly is a duck bill valve.

6. The surgical access device of claim 1, wherein the assembly comprises at least one instrument support.

7. The access device of claim 1 comprising a latch mechanism for releasably attaching the subassembly to the proximal end of the assembly.

8. A surgical access device for providing surgical access through an incision in the body wall to the inside of a body cavity of a patient, the surgical access device having a center axis and comprising:
    an assembly having a proximal end and a distal end and having an opening around the center axis, the assembly comprising an upper ring, a lower ring, and a sleeve extending generally axially from the upper ring to the lower ring, the sleeve and the lower ring positionable in the incision, the sleeve defining a passageway through the body wall between the opening in the assembly and the body cavity;
    a subassembly releasably positionable on the assembly and defining at least three apertures sized for accepting surgical instruments; and
    a member extending at least partially into the passageway defined by the sleeve, the member disposed radially outwardly and distally with respect to the at least three apertures and positioned with respect to the sleeve to protect the sleeve from instruments inserted through the apertures.

9. The device of claim 8 wherein the member comprises a distal end, and wherein the distal end of the member is disposed distally of the upper ring.

10. The device of claim 8 wherein the member positioned with respect to the sleeve is generally circumferentially continuous.

11. The device of claim 8 wherein the member comprises a collar.

12. The device of claim 8 further comprising a seal assembly associated with at least two of the apertures.

13. The device of claim 12 wherein the member positioned with respect to the sleeve extends distally below the seal assembly of at least one aperture.

14. The device of claim 8 comprising a plurality of seal assemblies operatively associated with the subassembly, and wherein at least a portion of the seal assemblies are positioned within the passageway defined by the sleeve.

15. A surgical access device comprising:
    a flexible sleeve adapted for insertion in an incision, the sleeve extending from a sleeve proximal end to a sleeve distal end, the sleeve providing a passageway intermediate the proximal and distal sleeve ends, the passageway having a minimum width at a position spaced from the proximal and distal sleeve ends;
    a plurality of instrument openings supported with respect to the proximal end of the sleeve;
    at least one valve associated with at least one instrument opening;
    a generally circumferentially continuous member disposed radially outwardly and distally relative to of the plurality of instrument openings: and
    wherein at least one valve is disposed distal of the proximal end of the sleeve.

16. The device of claim 15 further comprising a member disposed distally of at least one of the instrument openings, the member positioned with respect to the sleeve to protect the sleeve from instruments inserted through at least one instrument opening.

17. The device of claim 16 wherein the member comprises a generally circumferentially extending collar.

* * * * *